US008883438B2

(12) United States Patent
Cantley et al.

(10) Patent No.: US 8,883,438 B2
(45) Date of Patent: Nov. 11, 2014

(54) METHOD FOR DIAGNOSING CELL PROLIFERATION DISORDERS HAVING A NEOACTIVE MUTATION AT RESIDUE 97 OF ISOCITRATE DEHYDROGENASE 1

(75) Inventors: Lewis C. Cantley, Cambridge, MA (US); Leonard Luan C Dang, Boston, MA (US); Stefan Gross, Brookline, MA (US); Hyun Gyung Jang, Arlington, MA (US); Shengfang Jin, Newton, MA (US); Shin-San Michael Su, Newton, MA (US); Craig Thompson, New York, NY (US)

(73) Assignee: Agios Pharmaceuticals, Inc., Cambridge, MA (US)

( * ) Notice: Subject to any disclaimer, the term of this patent is extended or adjusted under 35 U.S.C. 154(b) by 0 days.

(21) Appl. No.: 13/619,387

(22) Filed: Sep. 14, 2012

(65) Prior Publication Data

US 2013/0316385 A1 Nov. 28, 2013

Related U.S. Application Data

(63) Continuation of application No. PCT/US2010/053624, filed on Oct. 21, 2010.

(60) Provisional application No. 61/253,818, filed on Oct. 21, 2009.

(51) Int. Cl.
*C12Q 1/32* (2006.01)

(52) U.S. Cl.
USPC .......................................................... 435/26

(58) Field of Classification Search
USPC .......................................................... 435/26
See application file for complete search history.

(56) References Cited

U.S. PATENT DOCUMENTS

| | | | |
|---|---|---|---|
| 5,984,882 A | 11/1999 | Rosenschein et al. | |
| 6,399,358 B1 | 6/2002 | Williams et al. | |
| 6,723,730 B2 | 4/2004 | Bakthavatchalam et al. | |
| 6,979,675 B2 | 12/2005 | Tidmarsh | |
| 7,173,025 B1 | 2/2007 | Stocker et al. | |
| 2003/0109527 A1 | 6/2003 | Jin et al. | |
| 2003/0207882 A1 | 11/2003 | Stocker et al. | |
| 2004/0067234 A1* | 4/2004 | Einat et al. | 424/155.1 |
| 2004/0248221 A1 | 12/2004 | Stockwell | |
| 2006/0281122 A1 | 12/2006 | Bryant et al. | |
| 2008/0300208 A1 | 12/2008 | Einat et al. | |
| 2009/0093526 A1 | 4/2009 | Miller et al. | |
| 2010/0331307 A1 | 12/2010 | Salituro et al. | |
| 2012/0121515 A1* | 5/2012 | Dang et al. | 424/9.3 |
| 2012/0164143 A1 | 6/2012 | Teeling et al. | |
| 2013/0035329 A1* | 2/2013 | Saunders et al. | 514/218 |
| 2013/0183281 A1 | 7/2013 | Su et al. | |

FOREIGN PATENT DOCUMENTS

| | | |
|---|---|---|
| EP | 0384228 A1 | 8/1990 |
| EP | 0385237 A2 | 9/1990 |
| FR | 2735127 A1 | 12/1996 |
| JP | 4099768 | 3/1992 |
| JP | 9291034 A | 11/1997 |
| JP | 11158073 | 6/1999 |
| WO | 0116097 A1 | 3/2001 |
| WO | 2004/073619 A2 | 9/2004 |
| WO | 2004/074438 A2 | 9/2004 |
| WO | 2006070198 A1 | 7/2006 |
| WO | 2007023186 A1 | 3/2007 |
| WO | 2008131547 A1 | 11/2008 |
| WO | 2009013126 A1 | 1/2009 |
| WO | 2009150248 A1 | 12/2009 |
| WO | 2010007756 A1 | 1/2010 |
| WO | 2010/028099 A1 | 3/2010 |
| WO | 2010105243 A1 | 9/2010 |
| WO | 2010144338 A1 | 12/2010 |
| WO | 2011002817 A1 | 1/2011 |
| WO | 2011005210 A1 | 1/2011 |
| WO | 2011/072174 A1 | 6/2011 |
| WO | 2012/009678 A1 | 1/2012 |
| WO | 2013102431 A1 | 7/2013 |

OTHER PUBLICATIONS

Bleeker F. et al. IDH1 Mutations at Residue pR132 Occur Frequently in High Grade Gliomas But Not in Other Solid Tumors. Human Mutation 30(1)7-11, Dec. 31, 2008.*
Kim T. et al. Ser95, Asn97, and Thr78 are Important for the Catalytic Function of Porcine NADP Dependent Isocitrate Dehydrogenase. Protein Science 14:140-147, 2005.*
Struys et al. "Mutations in the D-2-hydroxyglutarate dehydrogenase gene cause D-2-hydroxyglutaric aciduria" American Journal of Human Genetics (2005) vol. 76, pp. 358-360.
Supplementary European Search Report for EP 10751525 Mailed Dec. 14, 2012.
Supplementary European Search Report for EP Application No. 10825707.2 dated Jun. 28, 2013.
Thompson, "Metabolic Enzymes as Oncogenes or Tumor Suppressors." The New England Journal of Medicine (2009) vol. 360, No. 8, pp. 813-815.
Wang et al. "A novel ligand N,N'-di(2-pyridyl)-2,4-diamino-6-phenyl-1,3,5-triazine (dpdapt) and its complexes: [Cu (dpdapt)Cl2] and [Cu(dpdapt)(NO3)(H2O)] · NO3 · H2O" Polyhedron (2006) vol. 25, No. 1, pp. 195-202.
Ward et al. "The Common Feature of Leukemia-Associated IDH1 and IDH2 Mutations Is a Neomorphic Enzyme Activity Converting [alpha]-Ketoglutarate to 2-Hydroxyglutarate" Cancer Cell (2010) vol. 17, No. 3 pp. 225-234.
Watanabe et al., "IDH1 Mutations Are Early Events in the Development of Astrocytomas and Oligodendrogliomas". American Journal of Pathology (2009) vol. 174, No. 4, pp. 1149-1153.
Written Opinion for PCT/US2010/027253 mailed Aug. 19, 2010.
Written Opinion of International Search Authority for PCT/CN2013/000009 dated Apr. 18, 2013.

(Continued)

*Primary Examiner* — Ralph Gitomer
(74) *Attorney, Agent, or Firm* — Lando & Anastasi LLP

(57) ABSTRACT

Methods and compositions for treating and evaluating subjects having a neoactive mutation at residue 97 of IDH1 or 137 of IDH2.

12 Claims, 10 Drawing Sheets

(56) References Cited

OTHER PUBLICATIONS

Written Opinion of Search Authority for PCT/US2010/53623 dated Jan. 18, 2011.
Written Opinion of the International Searching Authority for PCT/US2011/067752 dated Mar. 5, 2012.
Yan et al., "IDH1 and IDH2 Mutations in Gliomas." The New England Journal of Medicine, (2009) vol. 360, No. 8, pp. 765-773.
Zhao et al. "Glioma-derived mutations in IDH1 dominantly inhibit IDH1 catalytic activity and induce HIF-1alpha", Science (2009) vol. 324, No. 5924, pp. 261-265.
Aghili et al. "Hydroxyglutaric aciduria and malignant brain tumor: a case report and literature review", Journal of Neuroncology (2008) 91 pp. 233-236.
Balss, "Analysis of the IDH1 codon 132 mutation in brain tumors", Acta Neuropathol (2008) vol. 116, pp. 597-602.
Benner et al, "Evolution, language and analogy in functional genomics", Trends in Genetics (2001) vol. 17, pp. 414-418.
Bleeker et al., "IDH1 mutations at residue p.R132 (IDH1 (R132)) occur frequently in high-grade 18-22 gliomas but not in other solid tumors." Hum Mutal., (2009) vol. 30, No. 1, pp. 7-11.
Cocco et al. "Synthesis of Triflouromethylated Pyridinecarbonitriles" Journal of Heterocyclic Chemistry (1995) vol. 32, pp. 543-545.
International Search Report and Written Opinion for International Application No. PCT/CN2013/081170 dated Apr. 30, 2014.
Dang et al. "Cancer-associated IDH1 mutations produce 2-hydroxyglutarate" Nature (2009)vol. 462, No. 7274, pp. 739-744.
Dang et al. "IDH Mutations in Glioma and Acute Myeloid Leukemia" Trends in Molecular Medicine (2010) vol. 16, No. 9, pp. 387-397.
Dohner et al. "Impact of Genetic Features on Treatment Decisions in AML" American Society of Hematology (2011) pp. 36-42.
EP Search Report & Written Opinion for EP 10825706 Dated Mar. 20, 2013.
European Search Report for Application No. 10751525.6 dated Dec. 14, 2012.
Eurpoean Search Report for EP Application No. 11763425.3 dated Sep. 23, 2013.
Hartmann et al. "Type and Frequency of IDH1 and IDH2 mutations are related to astrocytic and oligodendroglial differentiation and age: a study of 1010 diffuse gliomas" Acta Neuropathologica (2009) vol. 118, pp. 469-474.
Holmes et al. "750 MHz 1H NMR spectroscopy characterisation of the complex metabolic pattern of urine from patients with inborn errors of metabolism: 2-hydroxyglutaric aciduria and maple syrup urine disease" Journal of Pharmaceutical and Biomedical Analysis (1997) vol. 15, pp. 1647-1659.
International Preliminary Report for related application No. PCT/US2010/059778 dated Jun. 12, 2012.
International Preliminary Report on Patentability for PCT/CN2012/000841 dated Dec. 17, 2013.
International Preliminary Report on Patentability for PCT/CN2012/077096 dated Dec. 17, 2013.
International Preliminary Report on Patentability for PCT/US2010/027253 mailed Sep. 13, 2011.
International Preliminary Report on Patentability for PCT/US2010/053623 dated Apr. 24, 2012.
International Preliminary Report on Patentability for PCT/US2010/053624 dated Apr. 7, 2011.
International Preliminary Report on Patentability for PCT/US2011/030692 dated Oct. 2, 2012.
International Search Report & Written Opinion for PCT/CN2013/070755 dated Apr. 25, 2013.
International Search Report for PCT/2011/030692 dated Jul. 27, 2011.
International Search Report for PCT/CN2012/000841 dated Sep. 27, 2012.
International Search Report for PCT/CN2012/077096 dated Oct. 4, 2012.
International Search Report for PCT/CN2013/000009 dated Apr. 18, 2013.
International Search Report for PCT/CN2013/000068 dated Apr. 25, 2013.
International Search Report for PCT/US2010/027253 mailed Aug. 19, 2010.
International Search Report for PCT/US2010/059778 dated Mar. 17, 2011.
International Search Report for PCT/US2010/53623 dated Jan. 18, 2011.
International Search Report for PCT/US2010053624 dated Apr. 7, 2011.
International Search Report for PCT/US2011044254 dated May 10, 2011.
International Search Report for PCT/US2013/064601 dated Feb. 24, 2014.
Jennings et al. "Expression and mutagenesis of mammalian cytosolic NADP+-specific isocitrate dehydrogenase" Biochemistry (1997) vol. 36, pp. 13743-13747.
Kim et al. "Identification and Functional Characterization of a Novel, Tissue-specific NAD+-dependent Isocitrate Dehydrogenase b Subunit Isoform" JBC (1999) vol. 274, No. 52, pp. 36866-36875.
Kim et al. "Ser95, Asn97, and Thr78 are important for the catalytic function of porcine NADP-dependent isocitrate dehydrogenase" Protein Science (2005) vol. 14, pp. 140-147.
Kranendijk et al. "IDH2 Mutations in Patients with D-2-Hydroxyglutaric Aciduria" Science (2010) vol. 330, p. 336.
May et al. "How many species are there on earth" Science (1988) vol. 241, p. 1441.
Parsons et al. "An Integrated Genomic Analysis of Human Glioblastoma Multiforme" Science (2008) vol. 321, pp. 1807-1812 and Supplemental Data.
Pollard et al, "Cancer. Puzzling patterns of predisposition." Science (2009) vol. 324, pp. 192-194.
Popovici-Muller et al. "Discovery of the First Potent Inhibitors of Mutant IDH1 That Lower Tumor2-HG in Vivo" ACS Medicinal Chemistry Letters (2012) vol. 3, No. 10, pp. 850-855.
Pubchem CID 4078245 [online]; Sep. 13, 2005 [retrieved on Feb. 4, 2012]; retrieved from http://pubchem.ncbi.nim.nih.gov/; 2d-structure.
Pubchem CID 4854170 [online]; Sep. 17, 2005 [retrieved on Feb. 4, 2012]; retrieved from http://pubchem.ncbi.nim.nih.gov/; 2d-structure.
Raynaud et al. "Absence of R140Q Mutation of Isocitrate Dehydrogenase 2 in Gliomas and Breast Cancers" Oncology Letters (2010) vol. 1, No. 5, pp. 883-884.
Reitman et al. "Isocitrate Dehydrogenase 1 and 2 Mutations in Cancer: Alterations at a Crossroads of Cellular Metabolism" Journal of the National Cancer Institute (2010) vol. 102, No. 13, pp. 932-941.
Rohle et al. "An Inhibitor of Mutant IDH1 Delays Growth and Promotes Differentiation of Glioma Cells" Science (2013) vol. 340, No. 6132, pp. 626-630.
Shih et al. "The Role of Mutations in Epigenetic Regulators in Myeloid Malignancies" Nature Reviews Cancer (2012) vol. 12, No. 9, pp. 599-612.
Sirkanyan et al "Synthesis of new derivatives of piperazine-substituted pyrano[3,4-c]pyridines" Hayastani Kimiakan Handes (2009) vol. 62, No. 3-4 pp. 378-385. English Abstract Only.
Sonoda et al. "Analysis of IDH1 and IDH2 mutations in Japanese glioma patients" Cancer Science, vol. 100, No. 10, pp. 1996-1998.
Struys et al. "Investigations by mass isotopomer analysis of the formation of D-2-hydroxyglutarate by cultured lymphoblasts from two patients with D-2-hydroxyglutaric aciduria" FEBS Letters (2004) vol. 557, pp. 115-120.

* cited by examiner

```
  1 mskkisggsv vemqgdemtr iiwelikekl ifpyveldlh sydlglenrd atndqvtkda
 61 aeaikkhnvg vkcatitpde krveefklkq mwkspngtir nilggtvfre aiickniprl
121 vsgwvkpiii grhaygdqyr atdfvvpgpg kveitytpsd gtqkvtylvh nfeegggvam
181 gmynqdksie dfahssfqma lskgwplyls tkntilkkyd grfkdifqei ydkqyksqfe
241 aqkiwyehrl iddmvaqamk seggfiwack nydgdvqsds vaqgygslgm mtsvlvcpdg
301 ktveaeaahg tvtrhyrmyq kgqetstnpi asifawtrgl ahrakldnnk elaffanale
361 evsietieag fmtkdlaaci kglpnvqrsd ylntfefmdk lgenlkikla qakl
```

Fig. 2

```
   1 atgtccaaaa aaatcagtgg cggttctgtg gtagagatgc aaggagatga aatgacacga
  61 atcatttggg aattgattaa agagaaactc attttTccct acgtggaatt ggatctacat
 121 agctatgatt taggcataga gaatcgtgat gccaccaacg accaagtcac caaggatgct
 181 gcagaagcta taagaagca taatgttggc gtcaaatgtg ccactatcac tcctgatgag
 241 aagagggttg aggagttcaa gttgaaacaa atgtggaaat caccaaatgg caccatacga
 301 aatattctgg gtggcacggt cttcagagaa gccattatct gcaaaaatat ccccoggctt
 361 gtgagtggat gggtaaaacc tatcatcata ggtcgtcatg cttatgggga tcaatacaga
 421 gcaactgatt ttgttgttcc tgggcctgga aaagtagaga taacctacac accaagtgac
 481 ggaacccaaa aggtgacata cctggtacat aactttgaag aaggtggtgg tgttgccatg
 541 gggatgtata atcaagataa gtcaattgaa gattttgcac acagttcctt ccaaatggct
 601 ctgtctaagg gttggccttt gtatctgagc accaaaaaca ctattctgaa gaaatatgat
 661 gggcgtttta aagacatctt tcaggagata tatgacaagc agtacaagtc ccagtttgaa
 721 gctcaaaaga tctggtatga gcataggctc atcgacgaca tggtggccca agctatgaaa
 781 tcagagggag gcttcatctg ggcctgtaaa aactatgatg gtgacgtgca gtcggactct
 841 gtggcccaag ggtatggctc tctcggcatg atgaccagcg tgctggtttg tccagatggc
 901 aagacagtag aagcagaggc tgcccacggg actgtaaccc gtcactaccg catgtaccag
 961 aaggacagg agacgtccac caatcccatt gcttccattt ttgcctggac cagagggtta
1021 gcccacagag caaagcttga taacaataaa gagcttgcct tctttgcaaa tgctttggaa
1081 gaagtctcta ttgagacaat tgaggctggc ttcatgacca aggacttggc tgcttgcatt
1141 aaaggtttac ccaatgtgca acgttctgac tacttgaata catttgagtt catggataaa
1201 cttggagaaa acttgaagat caaactagct caggccaaac tttaa
```

Fig. 2A

```
   1 cctgtggtcc cgggtttctg cagagtctac ttcagaagcg gaggcactgg gagtccggtt
  61 tgggattgcc aggctgtggt tgtgagtctg agcttgtgag cggctgtggc gccccaactc
 121 ttcgccagca tatcatcccg gcaggcgata aactacattc agttgagtct gcaagactgg
 181 gaggaactgg ggtgataaga aatctattca ctgtcaaggt ttattgaagt caaaatgtcc
 241 aaaaaaatca gtggcggttc tgtggtagag atgcaaggag atgaaatgac acgaatcatt
 301 tgggaattga ttaaagagaa actcattttt ccctacgtgg aattggatct acatagctat
 361 gatttaggca tagagaatcg tgatgccacc aacgaccaag tcaccaagga tgctgcagaa
 421 gctataaaga agcataatgt tggcgtcaaa tgtgccacta tcactcctga tgagaagagg
 481 gttgaggagt tcaagttgaa acaaatgtgg aaatcaccaa atggcaccat acgaaatatt
 541 ctgggtgcca cggtcttcag agaagccatt atctgcaaaa atatccccg gcttgtgagt
 601 ggatgggtaa aacctatcat catggtcgt catgcttatg gggatcaata cagagcaact
 661 gattttgttg ttcctgggcc tggaaaagta gagataacct acacaccaag tgacggaacc
 721 caaaaggtga catacctggt acataacttt gaagaaggtg gtggtgttgc catggggatg
 781 tataatcaag ataagtcaat tgaagatttt gcacacagtt ccttccaaat ggctctgtct
 841 aagggttggc ctttgtatct gagcaccaaa aacactattc tgaagaaata tgatgggcgt
 901 tttaaagaca tctttcagga gatatatgac aagcagtaca agtccagtt tgaagctcaa
 961 aagatctggt atgagcatag gctcatcgac gacatggtgg cccaagctat gaaatcagag
1021 ggaggcttca tctgggcctg taaaaactat gatggtgacg tgcagtcgga ctctgtggcc
1081 caagggtatg gctctctcgg catgatgacc agctgctgg tttgtccaga tggcaagaca
1141 gtagaagcag aggctgccca cggactgta acccgtcact accgcatgta ccagaaagga
1201 caggagacgt ccaccaatcc cattgcttcc attttgcct ggaccagagg gttagcccac
1261 agcaaagc ttgataacaa taaagagctt gcttctttg caaatgcttt ggaagaagtc
1321 tctattgaga caattgaggc tggcttcatg accaaggact tggctgcttg cattaaaggt
1381 ttacccaatg tgcaacgttc tgactacttg aatacatttg agttcatgga taaacttgga
1441 gaaaacttga agatcaaact agctcaggcc aaactttaag ttcatacctg agctaagaag
1501 gataattgtc ttttggtaac taggtctaca ggtttacatt tttctgtgtt acactcaagg
1561 ataaaggcaa aatcaatttt gtaattgtt tagaagccag agtttatctt ttctataagt
1621 ttacagcctt tttcttatat atacagttat tgccacctttt gtgaacatgg caagggactt
1681 ttttacaatt tttattttat tttctagtac cagcctagga attcggttag tactcatttg
1741 tattcactgt cacttttct catgttctaa ttataaatga ccaaaatcaa gattgctcaa
1801 aagggtaaat gatagccaca gtattgctcc ctaaaatatg cataaagtag aaattcactg
1861 ccttcccctc ctgtccatga ccttgggcac agggaagttc tggtgtcata gatatcccgt
1921 tttgtgaggt agagctgtgc attaaacttg cacatgactg gaacgaagta tgagtgcaac
1981 tcaaatgtgt tgaagatact gcagtcattt tgtaaagac cttgctgaat gtttccaata
2041 gactaaatac tgtttaggcc gcaggagagt ttggaatccg gaataaatac tacctggagg
2101 tttgtcctct ccattttct cttctcctc ctggctggc ctgaatatta tactactcta
2161 aatagcatat ttcatccaag tgcaataatg taagctgaat cttttttgga cttctgctgg
2221 cctgttttat ttcttttata taaatgtgat ttctcagaaa ttgatattaa acactatctt
2281 atcttctcct gaactgttga ttttaattaa aattaagtgc taattaccaa aaaaaaaaaa
```

METHOD FOR DIAGNOSING CELL PROLIFERATION DISORDERS HAVING A NEOACTIVE MUTATION AT RESIDUE 97 OF ISOCITRATE DEHYDROGENASE 1

CLAIM OF PRIORITY

This application is a continuation of International Application No. PCT/US2010/053624 filed Oct. 21, 2010, which claims priority to U.S. Ser. No. 61/253,818, filed Oct. 21, 2009, the contents of which are incorporated herein by reference in their entirety.

FIELD OF INVENTION

The invention relates to methods and compositions for evaluating and treating cell proliferation-related disorders having a neoactive mutation at residue 97 of IDH1, e.g., proliferative disorders such as cancer.

BACKGROUND

Isocitrate dehydrogenase, also known as IDH, is an enzyme which participates in the citric acid cycle. It catalyzes the third step of the cycle: the oxidative decarboxylation of isocitrate, producing alpha-ketoglutarate (α-ketoglutarate or α-KG) and $CO_2$ while converting NAD+ to NADH. This is a two-step process, which involves oxidation of isocitrate (a secondary alcohol) to oxalosuccinate (a ketone), followed by the decarboxylation of the carboxyl group beta to the ketone, forming alpha-ketoglutarate. Another isoform of the enzyme catalyzes the same reaction; however this reaction is unrelated to the citric acid cycle, is carried out in the cytosol as well as the mitochondrion and peroxisome, and uses NADP+ as a cofactor instead of NAD+.

SUMMARY OF THE INVENTION

Methods and compositions disclosed herein relate to the role played in disease by neoactive products produced by an IDH1 gene having a mutation at residue 97 or an IDH2 gene having a neoactive mutation at residue 137. The inventors have discovered a neoactivity associated with a mutation at residue 97 of IDH1 and that the product of the neoactivity can be significantly elevated in cancer cells. Disclosed herein are methods and compositions for treating, and methods of evaluating, a subject having or at risk for a disorder, e.g., a cell proliferation-related disorder, characterized by a neoactive somatic mutation at residue 97 of IDH1, e.g., a mutation to other than G at residue 97, e.g., IDH1-G97D, that confers alpha hydroxy neoactivity, e.g., 2HG neoactivity, on the mutant IDH1 protein (such mutations are sometimes referred to herein as IDH1-97$^{neo}$ mutations and the corresponding mutants are sometimes referred to herein as IDH1-97$^{neo}$ mutants). The invention also concerns neoactive somatic mutation at residue 137 of IDH2, e.g., a mutation to other than G at residue 137, that confers alpha hydroxy neoactivity, e.g., 2HG neoactivity, on the mutant IDH2 protein (such mutations are sometimes referred to herein as IDH2-137$^{neo}$ mutations and the corresponding mutants are sometimes referred to herein as IDH2-137$^{neo}$ mutants). Exemplary disorders include, e.g., proliferative disorders such as cancer. The inventors have discovered and disclosed herein novel therapeutic agents for the treatment of disorders, e.g., cancers, characterized by a neoactivity resulting from a mutation at residue G97 of IDH1 or at G137 of IDH2. In embodiments a therapeutic agent reduces levels of neoactivity or neoactive product. Methods described herein also allow the identification of a subject or identification of a treatment for the subject, on the basis of neoactivity genotype or phenotype of an IDH1-97$^{neo}$ or IDH2-137$^{neo}$ mutation. This evaluation can allow for optimal matching of subject with treatment, e.g., where the selection of subject or treatment (or both) is responsive to an analysis of neoactivity genotype or phenotype of an IDH1-97$^{neo}$ or IDH2-137$^{neo}$ mutation. E.g., methods describe herein can allow selection of a treatment regimen comprising administration of a novel compound, e.g., a novel compound disclosed herein, or a known compound, e.g., a known compound not previously recommended for a selected disorder. In embodiments the known compound reduces levels of neoactivity or neoactive product of an IDH1-97$^{neo}$ or IDH2-137$^{neo}$ mutation. This approach can guide and provide a basis for selection and administration of a novel compound or a known compound, or combination of compounds, not previously recommended for subjects having a disorder characterized by an IDH1-97$^{neo}$ or IDH2-137$^{neo}$ mutation. In embodiments the neoactive genotype or phenotype of an IDH1-97$^{neo}$ or IDH2-137$^{neo}$ mutation can act as a biomarker the presence of which indicates that a compound, either novel, or previously known, should be administered to treat a disorder characterized by an IDH1-97$^{neo}$ or IDH2-137$^{neo}$ mutation.

In one aspect, the invention features, a method of treating a subject having a cell proliferation-related disorder characterized by an IDH1-97$^{neo}$ mutation, e.g., IDH1-G97D, or IDH2-137$^{neo}$ mutation, e.g., a precancerous disorder, or cancer.

As used herein, neoactivity is alpha hydroxy neoactivity, and refers to the ability of an IDH1 mutant enzyme encoded by an IDH1-97$^{neo}$, e.g., IDH1-G97D, or IDH2-137$^{neo}$, mutant gene to convert an alpha ketone to an alpha hydroxy. In embodiments alpha hydroxy neoactivity proceeds with a reductive cofactor, e.g., NADPH or NADH. In embodiments the alpha hydroxy neoactivity is 2HG neoactivity. 2HG neoactivity, as used herein, refers to the ability to convert alpha ketoglutarate to 2-hydroxyglutarate (sometimes referred to herein as 2HG), e.g., R-2-hydroxyglutarate (sometimes referred to herein as R-2HG). In embodiments 2HG neoactivity proceeds with a reductive cofactor, e.g., NADPH or NADH. In an embodiment the enzyme encoded by a IDH1-97$^{neo}$ mutant, e.g., IDH1-G97D, or IDH2-137$^{neo}$ mutant, can act on more than one substrate, e.g., more than one alpha hydroxy substrate.

The method comprises administering to the subject an effective amount of a nucleic acid based inhibitor described herein or other therapeutic agent of a type described herein, to thereby treat the subject.

In an embodiment the cell proliferation-related disorder is characterized by an IDH1-97$^{neo}$ mutation, e.g., IDH1-G97D.

In an embodiment the cell proliferation-related disorder is characterized by an IDH2-137$^{neo}$ mutation.

In an embodiment the therapeutic agent results in lowering the level of a neoactivity product, e.g., an alpha hydroxy neoactivity product, e.g., 2HG, e.g., R-2HG.

In an embodiment the method comprises administering a therapeutic agent that lowers neoactivity, e.g., 2HG neoactivity.

In an embodiment the method comprises administering an inhibitor of an enzyme encoded by an IDH1-97$^{neo}$ mutation, e.g., IDH1-G97D, or IDH2-137$^{neo}$ mutation.

In an embodiment the therapeutic agent comprises a nucleic acid-based therapeutic agent, e.g., a dsRNA, e.g., a dsRNA described herein.

In an embodiment the therapeutic agent is an inhibitor, e.g., a polypeptide, peptide, or small molecule (e.g., a molecule of less than 1,000 daltons), or aptamer, that binds to an IDH1-$97^{neo}$ mutation, e.g., IDH1-G97D, or IDH2-$137^{neo}$ mutation, or wildtype subunit and inhibits neoactivity, e.g., by inhibiting formation of a dimer, e.g., a homodimer of mutant IDH1 subunits or a heterodimer of a mutant and a wildype subunit.

In an embodiment the inhibitor is a polypeptide. In an embodiment the polypeptide acts as a dominant negative with respect to the neoactivity of the mutant enzyme. The polypeptide can correspond to full length IDH1 or a fragment thereof. The polypeptide need not be identical with the corresponding residues of wildtype IDH1, but in embodiments has at least 60, 70, 80, 90 or 95% homology with wildtype IDH1.

In an embodiment the therapeutic agent decreases the affinity of an IDH1-$97^{neo}$ mutant, or IDH2-$137^{neo}$ mutant, protein for NADH, NADPH or a divalent metal ion, e.g., $Mg^{2+}$ or $Mn^{2+}$, or decreases the levels or availability of NADH, NADPH or divalent metal ion, e.g., $Mg^{2+}$ or $Mn^{2+}$, e.g., by competing for binding to the mutant enzyme. In an embodiment the enzyme is inhibited by replacing $Mg^{2+}$ or $Mn^{2+}$ with $Ca^{2+}$.

In an embodiment the therapeutic agent is an inhibitor that reduces the level a neoactivity of an IDH1-$97^{neo}$ mutant, e.g., IDH1-G97D, 2HG neoactivity.

In an embodiment the therapeutic agent is an inhibitor that reduces the level of the product of a IDH1-$97^{neo}$ mutant, e.g., IDH1-G97D, e.g., it reduces the level of 2HG, e.g., R-2HG.

In an embodiment the therapeutic agent is an inhibitor that:
  inhibits, e.g., specifically, a neoactivity of an IDH1-$97^{neo}$ mutant, e.g., IDH1-G97D, neoactivity described herein, e.g., 2HG neoactivity; or
  inhibits both the wildtype activity and a neoactivity of IDH1-$97^{neo}$ mutant, e.g., IDH1-G97D, e.g., 2HG neoactivity.

In an embodiment the therapeutic agent is an inhibitor that is selected on the basis that it:
  inhibits, e.g., specifically, a neoactivity of an IDH1-$97^{neo}$ mutant, e.g., IDH1-G97D, neoactivity described herein e.g., 2HG neoactivity; or
  inhibits both the wildtype activity and a neoactivity of an IDH1-$97^{neo}$ mutant, e.g., IDH1-G97D, neoactivity described herein, e.g., 2HG neoactivity.

In an embodiment the therapeutic agent is an inhibitor that reduces the amount of IDH1-$97^{neo}$ mutant, e.g., IDH1-G97D, mutant, protein or mRNA.

In an embodiment the therapeutic agent is an inhibitor that interacts directly with, e.g., it binds to, IDH1-$97^{neo}$ mutant, e.g., IDH1-G97D, mutant, mRNA.

In an embodiment the therapeutic agent is an inhibitor that interacts directly with, e.g., it binds to, IDH1-$97^{neo}$ mutant, e.g., IDH1-G97D, mutant protein.

In an embodiment the therapeutic agent is an inhibitor that reduces the amount of neoactive enzyme activity, e.g., by interacting with, e.g., binding to, IDH1-$97^{neo}$ mutant, e.g., IDH1-G97D, mutant, protein. In an embodiment the inhibitor is other than an antibody.

In an embodiment the therapeutic agent is an inhibitor that is a small molecule and interacts with, e.g., binds, IDH1-$97^{neo}$ mutant, e.g., IDH1-G97D, mutant, mRNA.

In an embodiment the therapeutic agent is an inhibitor that interacts directly with, e.g., binds, either the mutant IDH1-$97^{neo}$, e.g., IDH1-G97D, mutant protein or interacts directly with, e.g., binds, the IDH1-$97^{neo}$ mutant, e.g., IDH1-G97D, mutant, mRNA.

In an embodiment the therapeutic agent is an inhibitor that reduces the level a neoactivity of an IDH2-$137^{neo}$ mutant, 2HG neoactivity.

In an embodiment the therapeutic agent is an inhibitor that reduces the level of the product of an IDH2-$137^{neo}$ mutant, e.g., it reduces the level of 2HG, e.g., R-2HG.

In an embodiment the therapeutic agent is an inhibitor that:
  inhibits, e.g., specifically, a neoactivity of an IDH2-$137^{neo}$ mutant, neoactivity described herein, e.g., 2HG neoactivity; or
  inhibits both the wildtype activity and a neoactivity of an IDH2-$137^{neo}$ mutant, e,g, 2HG neoactivity.

In an embodiment the therapeutic agent is an inhibitor that is selected on the basis that it:
  inhibits, e.g., specifically, a neoactivity of an IDH2-$137^{neo}$ mutant, neoactivity described herein e.g., 2HG neoactivity; or
  inhibits both the wildtype activity and a neoactivity of an IDH2-$137^{neo}$ mutant, neoactivity described herein, e.g., 2HG neoactivity.

In an embodiment the therapeutic agent is an inhibitor that reduces the amount of IDH2-$137^{neo}$ mutant protein or mRNA.

In an embodiment the therapeutic agent is an inhibitor that interacts directly with, e.g., it binds to, IDH2-$137^{neo}$ mutant mRNA.

In an embodiment the therapeutic agent is an inhibitor that interacts directly with, e.g., it binds to, IDH2-$137^{neo}$ mutant protein.

In an embodiment the therapeutic agent is an inhibitor that reduces the amount of neoactive enzyme activity, e.g., by interacting with, e.g., binding to, IDH2-$137^{neo}$ mutant protein. In an embodiment the inhibitor is other than an antibody.

In an embodiment the therapeutic agent is an inhibitor that is a small molecule and interacts with, e.g., binds, IDH2-$137^{neo}$ mutant, mRNA.

In an embodiment the therapeutic agent is an inhibitor that interacts directly with, e.g., binds, either the mutant IDH2-$137^{neo}$ mutant protein or interacts directly with, e.g., binds, the IDH2-$137^{neo}$ mutant, mRNA.

In an embodiment the therapeutic agent is a cellular structural analog of a neoactivity product, or a prodrug thereof, e.g., as described in the section entitled "Cellular structural analogs of neoactivity products, and prodrugs thereof" elsewhere herein.

In an embodiment the therapeutic agent is an antiglycolytic agent, e.g., an anti-glycolytic agent described in the section entitled "Anti-glycolytic compounds" herein.

In an embodiment the therapeutic agent is an antioxidant, e.g., an antioxidant agent described in the section entitled "Antioxidants" herein.

In an embodiment the therapeutic agent is a hypomethylating agent, e.g., an hypomethylating agent described in the section entitled "Hypomethylating Agents" herein.

In an embodiment the therapeutic agent that makes the 2HG, e.g., R-2HG, more toxic to cells, e.g., by modulating an enzyme that results in converting 2HG, e.g., R-2HG, inot a more toxic substance, e.g., where the 2 HG, e.g., R-2HG, acts as a prodrug or an inhibitor that targets 2HG dehydrogenase, or a modulator that leads to the conversion of 2HG to another metabolite that is toxic to the cancer cell.

Treatment methods described herein can comprise evaluating the genotype or phenotype an IDH1-$97^{neo}$ mutant, e.g., IDH1-G97D or IDH2-$137^{neo}$ mutant. Methods of obtaining and analyzing samples, and the in vivo analysis in subjects, described elsewhere herein, e.g., in the section entitled, "Methods of evaluating samples and/or subjects," can be combined with this method.

In an embodiment, prior to or after treatment, the method includes evaluating the growth, size, weight, invasiveness, stage or other phenotype of the cell proliferation-related disorder.

In an embodiment, prior to or after treatment, the method includes evaluating the alpha hydroxy neoactivity genotype or phenotype, e.g., 2HG neoactivity genotype or phenotype of an IDH1-97$^{neo}$ mutant, e.g., IDH1-G97D, or IDH2-137$^{neo}$ mutant. Evaluating the alpha hydroxy, e.g., 2HG, genotype can comprise determining if an IDH1-97$^{neo}$, or IDH2-137$^{neo}$, mutation, e.g., having 2HG neoactivity, is present. Alpha hydroxy neoactivity phenotype, e.g., 2HG, e.g., R-2HG, phenotype, as used herein, refers to the level of alpha hydroxy neoactivity product, e.g., 2HG, e.g., R-2HG, level of alpha hydroxy neoactivity, e.g., 2HG neoactivity, or level of an IDH1-97$^{neo}$, e.g., IDH1-G97D, or IDH2-137$^{neo}$, mutation-encoded mutant enzyme (or corresponding mRNA). The evaluation can be by a method described herein. Alpha hydroxy, e.g., 2HG, genotype refers to the sequence at residue 97 of IDH1 or residue 137 at IDH2 (which can be determined, e.g., by direct interrogation of a nucleotide encoding residue 97 or 137 or by SNP analysis).

In an embodiment the subject can be evaluated, before or after treatment, to determine if the cell proliferation-related disorder is characterized by an alpha hydroxy neoactivity product, e.g., 2HG, e.g., R-2HG.

In an embodiment a cancer characterized by an IDH1-97$^{neo}$, e.g., IDH1-G97D, or IDH2-137$^{neo}$, mutation, e.g., a glioma or brain tumor in a subject, can be analyzed, e.g., by imaging and/or spectroscopic analysis, e.g., magnetic resonance-based analysis, e.g., MRI and/or MRS, e.g., before or after treatment, to determine if it is characterized by presence of an alpha hydroxy neoactivity product, e.g., 2HG, e.g., R-2HG.

In an embodiment the method comprises evaluating, e.g., by direct examination or evaluation of the subject, or a sample from the subject, or receiving such information about the subject, the IDH1-97$^{neo}$ mutant, e.g., IDH1-G97D, or IDH2-137$^{neo}$ mutant, genotype, or phenotype of, the subject, e.g., of a cell, e.g., a cancer cell, characterized by the cell proliferation-related disorder. (As described in more detail elsewhere herein the evaluation can be, e.g., by DNA sequencing of residue 97 of IDH1, immuno analysis, evaluation of the presence, distribution or level of an alpha hydroxy neoactivity product, e.g., 2HG, e.g., R-2HG, e.g., from spectroscopic analysis, e.g., magnetic resonance-based analysis, e.g., MRI and/or MRS measurement, spinal cord fluid analysis, analysis of urine, analysis of fecal matter (e.g., in the case of colorectal cancer) or by analysis of surgical material, e.g., by mass-spectroscopy). In embodiments this information is used to determine or confirm that a proliferation-related disorder, e.g., a cancer, is characterized by an alpha hydroxy neoactivity product, e.g., 2HG, e.g., R-2HG. In embodiments this information is used to determine or confirm that a cell proliferation-related disorder, e.g., a cancer, is characterized by an enzyme encoded by an IDH1-97$^{neo}$, e.g., IDH1-G97D, or IDH2-137$^{neo}$, mutant gene.

In an embodiment, before and/or after treatment has begun, the subject is evaluated or monitored by a method described herein, e.g., the analysis of the presence, distribution, or level of an alpha hydroxy neoactivity product, e.g., 2HG, e.g., R-2HG, e.g., to select, diagnose or prognose the subject, to select an inhibitor, or to evaluate response to the treatment or progression of disease characterized by an IDH1-97$^{neo}$, e.g., IDH1-G97D or IDH2-137$^{neo}$, mutation.

In an embodiment the cell proliferation-related disorder is a tumor of the CNS, e.g., a glioma, a leukemia, e.g., AML or ALL, e.g., B-ALL or T-ALL, prostate cancer, colorectal cancer, or myelodysplasia or myelodysplastic syndrome, characterized by an IDH1-97$^{neo}$, e.g., IDH1-G97D, or IDH2-137$^{neo}$, mutation, and the evaluation is: evaluation of the presence, distribution, or level of an alpha hydroxy neoactivity product, e.g., 2HG, e.g., R-2HG; or evaluation of the presence, distribution, or level of a neoactivity, e.g., an alpha hydroxy neoactivity, e.g., 2HG neoactivity, of an IDH1-97$^{neo}$, e.g., IDH1-G97D, or IDH2-137$^{neo}$, mutant protein.

In an embodiment the presence of an IDH1-97$^{neo}$ mutation, e.g., IDH1-G97D, or IDH2-137$^{neo}$ mutation, is determined, e.g, by sequencing genomic DNA or cDNA, from an affected cell.

In an embodiment the disorder is other than a solid tumor. In an embodiment the disorder is a tumor that, at the time of diagnosis or treatment, does not have a necrotic portion. In an embodiment the disorder is a tumor in which at least 30, 40, 50, 60, 70, 80 or 90% of the tumor cells are characterized by an IDH1-97$^{neo}$ mutation, e.g., IDH1-G97D, or IDH2-137$^{neo}$ mutation, at the time of diagnosis or treatment.

In an embodiment the cell proliferation-related disorder is a cancer characterized by an IDH1-97$^{neo}$ mutation, e.g., IDH1-G97D, or IDH2-137$^{neo}$ mutation, e.g., a cancer described herein. In an embodiment the cancer is characterized by increased levels of an alpha hydroxy neoactivity product, 2HG, e.g., R-2HG, as compared to non-diseased cells of the same type.

In an embodiment the method comprises selecting a subject having cancer, on the basis of the cancer being characterized by an IDH1-97$^{neo}$ mutation, e.g., IDH1-G97D (the sequence of IDH1 is provided in (SEQ ID NO:8)) or IDH2-137$^{neo}$ mutation.

In an embodiment the method comprises selecting a subject having a glioma, characterized by an IDH1-97$^{neo}$ mutation, e.g., IDH1-G97D, or IDH2-137$^{neo}$ mutation, on the basis of the cancer being characterized by unwanted levels of an alpha hydroxy neoactivity, product, e.g., 2HG, e.g., R-2HG.

In an embodiment the cell proliferation-related disorder is a tumor of the CNS, e.g., a glioma, e.g., wherein the tumor is characterized by an IDH1-97$^{neo}$ mutation, e.g., IDH1-G97D, or IDH2-137$^{neo}$ mutation. Gliomas include astrocytic tumors, oligodendroglial tumors, oligoastrocytic tumors, anaplastic astrocytomas, and glioblastomas. In an embodiment the tumor is characterized by increased levels of an alpha hydroxy neoactivity product, e.g., 2HG, e.g., R-2HG, as compared to non-diseased cells of the same type.

In an embodiment the method comprises selecting a subject having a glioma, on the basis of the cancer being characterized by an IDH1-97$^{neo}$ mutation, e.g., IDH1-G97D, or IDH2-137$^{neo}$ mutation.

In an embodiment the method comprises selecting a subject having a glioma characterized by an IDH1-97$^{neo}$ mutation, e.g., IDH1-G97D, or IDH2-137$^{neo}$ mutation on the basis of the cancer being characterized by unwanted levels of an alpha hydroxy neoactivity, product, e.g., 2HG, e.g., R-2HG.

In an embodiment the cell proliferation-related disorder is localized or metastatic prostate cancer, e.g., prostate adenocarcinoma, e.g., wherein the cancer is characterized by an IDH1-97$^{neo}$ mutation, e.g., IDH1-G97D, or IDH2-137$^{neo}$ mutation. In an embodiment the cancer is characterized by increased levels of an alpha hydroxy neoactivity product, e.g., 2HG, e.g., R-2HG, as compared to non-diseased cells of the same type.

In an embodiment the method comprises selecting a subject having prostate cancer, e.g., prostate adenocarcinoma, wherein the cancer is characterized by an IDH1-97$^{neo}$ mutation, e.g., IDH1-G97D, or IDH2-137$^{neo}$ mutation.

In an embodiment the method comprises selecting a subject having prostate cancer, e.g., prostate adenocarcinoma, on the basis of the cancer being characterized by an IDH1-97$^{neo}$ mutation, e.g., IDH1-G97D, or IDH2-137$^{neo}$ mutation.

In an embodiment the method comprises selecting a subject having prostate cancer characterized by an IDH1-97$^{neo}$ mutation, e.g., IDH1-G97D, or IDH2-137$^{neo}$ mutation on the basis of the cancer being characterized by unwanted levels of an alpha hydroxy neoactivity product, e.g., 2HG, e.g., R-2HG.

In an embodiment the cell proliferation-related disorder is a hematological cancer, e.g., a leukemia, e.g., AML, or ALL, wherein the hematological cancer is characterized by an IDH1-97$^{neo}$ mutation, e.g., IDH1-G97D, or IDH2-137$^{neo}$ mutation. In an embodiment the cancer is characterized by increased levels of an alpha hydroxy neoactivity product, e.g., 2HG, e.g., R-2HG, as compared to non-diseased cells of the same type.

In an embodiment the cell proliferation-related disorder is acute lymphoblastic leukemia (e.g., an adult or pediatric form), e.g., wherein the acute lymphoblastic leukemia (sometimes referred to herein as ALL) is characterized by an IDH1-97$^{neo}$ mutation, e.g., IDH1-G97D, or IDH2-137$^{neo}$ mutation. The ALL can be, e.g., B-ALL or T-ALL. In an embodiment the cancer is characterized by increased levels of a 2 alpha hydroxy neoactivity product, e.g., HG, e.g., R-2HG, as compared to non-diseased cells of the same type.

In an embodiment the method comprises selecting a subject having ALL, e.g., B-ALL or T-ALL, characterized by an IDH1-97$^{neo}$ mutation, e.g., IDH1-G97D, SEQ ID NO:8, or IDH2-137$^{neo}$ mutation.

In an embodiment the method comprises selecting a subject ALL, e.g., B-ALL or T-ALL, on the basis of cancer being characterized by an IDH1-97$^{neo}$ mutation, e.g., IDH1-G97D, or IDH2-137$^{neo}$ mutation.

In an embodiment the method comprises selecting a subject having ALL, e.g., B-ALL or T-ALL, characterized by an IDH1-97$^{neo}$ mutation, e.g., IDH1-G97D, or IDH2-137$^{neo}$ mutation, on the basis of the cancer being characterized by unwanted levels of an alpha hydroxy neoactivity product, e.g., 2HG, e.g., R-2HG.

In an embodiment the cell proliferation-related disorder is acute myelogenous leukemia (e.g., an adult or pediatric form), e.g., wherein the acute myelogenous leukemia (sometimes referred to herein as AML) is characterized by an IDH1-97$^{neo}$ mutation, e.g., IDH1-G97D, or IDH2-137$^{neo}$ mutation. In an embodiment the cancer is characterized by increased levels of an alpha hydroxy neoactivity product, e.g., 2HG, e.g., R-2HG, as compared to non-diseased cells of the same type.

In an embodiment the method comprises selecting a subject having acute myelogenous lymphoplastic leukemia (AML) characterized by an IDH1-97$^{neo}$ mutation, e.g., IDH1-G97D SEQ ID NO:8, or IDH2-137$^{neo}$ mutation.

In an embodiment the method comprises selecting a subject having acute myelogenous lymphoplastic leukemia (AML) on the basis of cancer being characterized by an IDH1-97$^{neo}$ mutation, e.g., IDH1-G97D, or IDH2-137$^{neo}$ mutation.

In an embodiment the method comprises selecting a subject having acute myelogenous lymphoplastic leukemia (AML) characterized by an IDH1-97$^{neo}$ mutation, e.g., IDH1-G97D, or IDH2-137$^{neo}$ mutation on the basis of cancer being characterized by unwanted levels of an alpha hydroxy neoactivity product, e.g., 2HG, e.g., R-2HG.

In an embodiment the method further comprises evaluating the subject for the presence of a mutation in the NRAS or NPMc gene.

In an embodiment the cell proliferation-related disorder is myelodysplasia or myelodysplastic syndrome, e.g., wherein the myelodysplasia or myelodysplastic syndrome is characterized by an IDH1-97$^{neo}$ mutation, e.g., IDH1-G97D, or IDH2-137$^{neo}$ mutation. In an embodiment the disorder is characterized by increased levels of an alpha hydroxy neoactivity product, e.g., 2HG, e.g., R-2HG, as compared to non-diseased cells of the same type.

In an embodiment the method comprises selecting a subject having myelodysplasia or myelodysplastic syndrome, wherein the disorder is characterized by an IDH1-97$^{neo}$ mutation, e.g., IDH1-G97D, or IDH2-137$^{neo}$ mutation.

In an embodiment the method comprises selecting a subject having myelodysplasia or myelodysplastic syndrome, on the basis of the disorder being characterized by an IDH1-97$^{neo}$ mutation, e.g., IDH1-G97D, or IDH2-137$^{neo}$ mutation.

In an embodiment the method comprises selecting a subject having myelodysplasia or myelodysplastic syndrome characterized by an IDH1-97$^{neo}$ mutation, e.g., IDH1-G97D, or IDH2-137$^{neo}$ mutation, on the basis of the cancer being characterized by unwanted levels of an alpha hydroxy neoactivity product, e.g., 2HG, e.g., R-2HG.

In an embodiment the cell proliferation-related disorder is colorectal cancer, e.g., wherein the cancer is characterized by an IDH1-97$^{neo}$ mutation, e.g., IDH1-G97D, or IDH2-137$^{neo}$ mutation. In an embodiment the cancer is characterized by increased levels of an alpha hydroxy neoactivity product, e.g., 2HG, e.g., R-2HG, as compared to non-diseased cells of the same type.

In an embodiment the method comprises selecting a subject having colorectal cancer, wherein the cancer is characterized by an IDH1-97$^{neo}$ mutation, e.g., IDH1-G97D, or IDH2-137$^{neo}$ mutation.

In an embodiment the method comprises selecting a subject having colorectal cancer, on the basis of the cancer being characterized by an IDH1-97$^{neo}$ mutation, e.g., IDH1-G97D, or IDH2-137$^{neo}$ mutation.

In an embodiment the method comprises selecting a subject having colorectal cancer characterized by an IDH1-97$^{neo}$ mutation, e.g., IDH1-G97D, or IDH2-137$^{neo}$ mutation, on the basis of the cancer being characterized by unwanted levels of an alpha hydroxy neoactivity product, e.g., 2HG, e.g., R-2HG.

In an embodiment a product of the neoactivity is 2HG (e.g., R-2HG) which acts as a metabolite. In another embodiment a product of the neoactivity is 2HG (e.g., R-2HG) which acts as a toxin, e.g., a carcinogen.

In an embodiment the subject does not have, or has not been diagnosed as having, 2-hydroxyglutaric aciduria.

In some embodiments, the methods described herein can result in reduced side effects relative to other known methods of treating cancer.

Therapeutic agents and methods of subject evaluation described herein can be combined with other therapeutic mocalities, e.g., with art-known treatments.

In an embodiment the method comprises providing a second treatment, to the subject, e.g., surgical removal, irradiation or administration of a chemotherapeutitc agent, e.g., an administration of an alkylating agent. Administration (or the establishment of therapeutic levels) of the second treatment can: begin prior to the beginning or treatment with (or prior to the establishment of therapeutic levels of) the inhibitor; begin after the beginning or treatment with (or after the establishment of therapeutic levels of) the inhibitor, or can be administered concurrently with the inhibitor, e.g., to achieve therapeutic levels of both concurrently.

In an embodiment the cell proliferation-related disorder is a CNS tumor, e.g., a glioma, and the second therapy comprises administration of one or more of: radiation; an alkylating agent, e.g., temozolomide, e.g., Temoader®, or BCNU; or an inhibitor of HER1/EGFR tyrosine kinase, e.g., erlotinib, e.g., Tarceva®.

The second therapy, e.g., in the case of glioma, can comprise implantation of BCNU or carmustine in the brain, e.g., implantation of a Gliadel® wafer.

The second therapy, e.g., in the case of glioma, can comprise administration of imatinib, e.g., Gleevec®.

In an embodiment the cell proliferation-related disorder is prostate cancer and the second therapy comprises one or more of: androgen ablation; administration of a microtubule stabilizer, e.g., docetaxol, e.g., Taxotere®; or administration of a topoisomerase II inhibitor, e.g., mitoxantrone.

In an embodiment the cell proliferation-related disorder is ALL, e.g., B-ALL or T-ALL, and the second therapy comprises one or more of:
induction phase treatment comprising the administration of one or more of: a steroid; an inhibitor of microtubule assembly, e.g., vincristine; an agent that reduces the availability of asparagine, e.g., asparaginase; an anthracycline; or an antimetabolite, e.g., methotrexate, e.g., intrathecal methotrexate, or 6-mercaptopurine;
consolidation phase treatment comprising the administration of one or more of: a drug listed above for the induction phase; an antimetabolite, e.g., a guanine analog, e.g., 6-thioguanine; an alkylating agent, e.g., cyclophosphamide; an anti-metabolite, e.g., AraC or cytarabine; or an inhibitor of topoisomerase I, e.g., etoposide; or
maintenance phase treatment comprising the administration of one or more of the drugs listed above for induction or consolidation phase treatment.

In an embodiment the cell proliferation-related disorder is AML and the second therapy comprises administration of one or more of: an inhibitor of topoisomerase II, e.g., daunorubicin, idarubicin, topotecan or mitoxantrone; an inhibitor of topoisomerase I, e.g., etoposide; an anti-metabolite, e.g., AraC or cytarabine; or a hypomethylating agent, e.g., decitabine (5-aza-deoxycytidine) or azacitidine (5-azacytidine).

In an embodiment the cell proliferation-related disorder is myelodysplasia or myelodysplastic syndrome and the second therapy comprises administration of one or more of: an inhibitor of topoisomerase II, e.g., daunorubicin, idarubicin, topotecan or mitoxantrone; an inhibitor of topoisomerase I, e.g., etoposide; an anti-metabolite, e.g., AraC or cytarabine; or a hypomethylating agent, e.g., decitabine (5-aza-deoxycytidine) or azacitidine (5-azacytidine).

As discussed above, the inventors have discovered that IDH1-97$^{neo}$ mutants, e.g., IDH1-G97D, or IDH2-137$^{neo}$ mutant, having, e.g., 2HG neoactivity, can result in significant increases in the level of cellular alpha hydroxy neoactivity product, e.g., 2HG, e.g., R-2HG. In embodiments the method includes providing a treatment to the subject having a disorder characterized by an IDH1-97$^{neo}$ mutant, e.g., IDH1-G97D, or IDH2-137$^{neo}$ mutant, wherein the treatment comprises:
i) providing a treatment that decreases the ability of an alpha hydroxy neoactivity product, e.g., 2HG, e.g., R-2HG, to compete with a cellular structural analog of the alpha hydroxy neoactivity product, e.g., 2HG, e.g., R-2HG, for interaction with, e.g., binding to cellular component;

ii) administering to the subject, a cellular structural analog of the alpha hydroxy neoactivity product, e.g., 2HG, e.g., R-2HG, or prodrug thereof; or
iii) administering a compound that reduces the cellular levels of the alpha hydroxy neoactivity product, e.g., 2HG, e.g., R-2HG, e.g., by degrading or metabolizing the alpha hydroxy neoactivity product, e.g., 2HG, e.g., R-2HG, thereby treating said subject.

In an embodiment decreasing the ability of an alpha hydroxy neoactivity product to compete with a cellular structural analog of the alpha hydroxy neoactivity product means increasing the cellular concentration of the structural analog of the alpha hydroxy neoactivity product relative to the concentration of the alpha hydroxy neoactivity product.

In an embodiment a structural analog of the alpha hydroxy neoactivity product, e.g., 2HG, e.g., R-2HG, is a substance can compete, under physiological conditions, with the alpha hydroxy neoactivity product, e.g., 2HG, e.g., R-2HG, for binding to a cellular component, e.g., an enzyme, e.g., prolyl hydroxylase, a dioxygenase, a histone demethylase such as a member of the JHDM family (The JHDM proteins use alpha ketoglutarate and iron (Fe) as cofactors to hydroxylate the methylated substrate). The affinity of the alpha hydroxy neoactivity product, e.g., 2HG, e.g., R-2HG, for the substrate is at least as great as the affinity of the structural analog of the alpha hydroxy neoactivity product, e.g., 2HG, e.g., R-2HG, for one or more of the named enzymes.

In an embodiment, the cellular structural analog of the alpha hydroxy neoactivity product is a compound of the following formula:

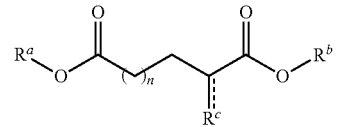

wherein;
each $R^a$ and $R^b$ are independently H, a metal ion, or a negative charge;
$R^c$ is a hydrogen bond donor or acceptor, and can be bound to the carbon chain by way of a single or double bond, as indicated by the dashed line; and
n is 0, 1, or 2.

Exemplary hydrogen bond donors include hydroxy and amino groups. An exemplary hydrogen bond acceptor is a carbonyl.

In an embodiment the cellular structural analog of the alpha hydroxy neoactivity product, e.g., 2HG, e.g., R-2HG, is a metabolite, e.g., glutamate or alpha ketoglutarate.

In an embodiment the competition comprises competition between the alpha hydroxy neoactivity product, e.g., 2HG, e.g., R-2HG, and a cellular structural analog of the alpha hydroxy neoactivity product, e.g., alpha ketoglutarate, for interaction with a cellular component, e.g., a cellular protein, e.g., an enzyme. In an embodiment the interaction can comprise binding to the cellular component. In an embodiment the interaction can comprise modification, e.g., covalent modification, of one or more of: the alpha hydroxy neoactivity product, e.g., 2HG, e.g., R-2HG; a cellular structural analog of the alpha hydroxy neoactivity product, e.g., alpha ketoglutarate; or the cellular component, e.g., a cellular protein, e.g., an enzyme. In an embodiment the modification is catalyzed or mediated by the cellular component. E.g., 2HG, e.g., R-2HG, can compete with alpha ketoglutarate, for modification of the alpha ketoglutarate, by the cellular component, e.g., an enzyme.

In embodiments, the increased level of the alpha hydroxy neoactivity product, e.g., 2HG, e.g., R-2HG, alters cellular function, e.g., cellular metabolism or mitochondrial function, by competing with cellular components that are structurally similar to the alpha hydroxy neoactivity product, e.g., 2HG, e.g., R-2HG, e.g., for access to substrates.

In an embodiment the treatment comprises administering a compound, e.g., a compound described herein, that is a naturally occurring cellular structural analog of 2HG, e.g., R-2HG, or prodrug of the naturally occurring cellular structural analog.

Suitable compounds comprise, e.g., a metabolite, e.g., glutamate or alpha ketoglutarate, or a prodrug thereof. In an embodiment the compound competes with 2HG, e.g., R-2HG, for binding to an enzyme. Exemplary enzymes comprise cellular prolyl hydroxylase, a dioxygenase, or a histone demethylase such as a member of the JHDM family.

In an embodiment the cellular structural analog of a neoactive product, or prodrug thereof, is a compound of the formula below:

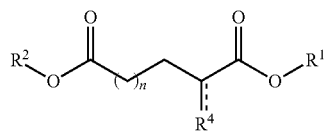

wherein R1, R2, R4 and n are as described herein. Exemplary structures include those structures of Formula (I), (II), (III), (IV) or (V):

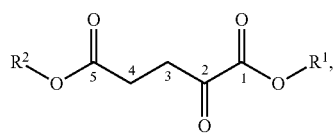
(I)

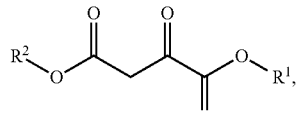
(II)

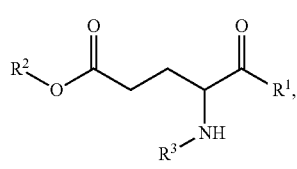
(III)

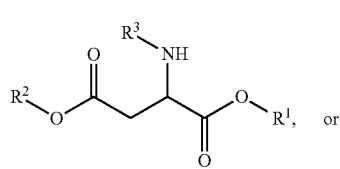
(IV) or

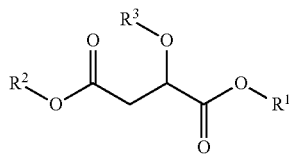
(V)

wherein R1, R2, and R3 are as defined herein.

In an embodiment the treatment comprises administering a compound that reduces the cellular levels of the alpha hydroxy neoactivity product, e.g., 2HG, e.g., R-2HG, e.g., by degrading or metabolizing the alpha hydroxy neoactivity product, e.g., 2HG, e.g., R-2HG. E.g., the treatment can comprise administering a cofactor for an enzyme that metabolizes the alpha hydroxy neoactivity product, e.g., 2HG, e.g., R-2HG, e.g., administering FAD (flavin adenine dinucleotide) or a precursor thereof, e.g., riboflavin, or an analog of FAD, the cofactor for 2HG dehydrogenase.

In an embodiment, the therapeutic agent sequesters an alpha hydroxy neoactivity product, e.g., 2HG, e.g., R-2HG, inactivates an alpha hydroxy neoactivity product, e.g., 2HG, e.g., R-2HG, or increases the metabolic conversion of an alpha hydroxy neoactivity product, e.g., 2HG, e.g., R-2HG, to another product. E.g., such treatment can include the administration of an antibody, apt.mer or small molecule that binds to and inactivates an alpha hydroxy neoactivity product, e.g., 2HG, e.g., R-2HG, or the administration of an enzyme, or a nucleic acid encoding an enzyme, that converts an alpha hydroxy neoactivity product, e.g., 2HG, e.g., R-2HG to another compound. E.g, a dehydrogenase, e.g., 2-HG dehydrogenase, or a gene encoding it, or a treatment that increases its activity, can be administered to the subject.

In another aspect, the invention features, a method of evaluating, e.g. diagnosing, a subject having a proliferation-related disorder characterized by an IDH1-97$^{neo}$ mutation, e.g., IDH1-G97D, or IDH2-137$^{neo}$ mutation. The method comprises analyzing a parameter related to the IDH1-97$^{neo}$ mutation, e.g., IDH1-G97D, or IDH2-137$^{neo}$, genotype or phenotype of the subject, e.g., analyzing one or more of:

a) the presence, distribution, or level of a neoactive product, e.g., 2HG, e.g., R-2HG, in a cell or tissue having an IDH1-97$^{neo}$ mutation, e.g., IDH1-G97D, or IDH2-137$^{neo}$ mutation;

b) the presence, distribution, or level of a neoactivity, e.g., 2HG neoactivity, of an IDH1 mutant protein encoded by an IDH1-97$^{neo}$ mutant, e.g., IDH1-G97D, or IDH2-137$^{neo}$ mutant;

c) the presence, distribution, or level of a neoactive mutant protein encoded by an IDH1-97$^{neo}$ mutant, e.g., IDH1-G97D, or IDH2-137$^{neo}$ mutant or a corresponding RNA; or d) the presence of an IDH1-97$^{neo}$ mutation, e.g., IDH1-G97D, or IDH2-137$^{neo}$ mutation, in cells characterized by a cell proliferation-related disorder from the subject, thereby evaluating the subject.

In an embodiment the cell proliferation-related disorder is characterized by an IDH1-97$^{neo}$ mutation, e.g., IDH1-G97D.

In an embodiment the cell proliferation-related disorder is characterized by an IDH2-137$^{neo}$ mutation.

In an embodiment analyzing comprises performing a procedure, e.g., a test, to provide data or information on one or more of a-d, e.g., performing a method which results in a physical change in a sample, in the subject, or in a device or reagent used in the analysis, or which results in the formation of an image representative of the data. Methods of obtaining and analyzing samples, and the in vivo analysis in subjects, described elsewhere herein, e.g., in the section entitled, "Methods of evaluating samples and/or subjects," can be combined with this method. In another embodiment analyzing comprises receiving data or information from such test from another party. In an embodiment the analyzing comprises receiving data or information from such test from another party and, the method comprises, responsive to that data or information, administering a treatment to the subject.

As described herein, the evaluation can be used in a number of applications, e.g., for diagnosis, prognosis, staging, determination of treatment efficacy, patent selection, or drug selection.

Thus, in an embodiment method further comprises, e.g., responsive to the analysis of one or more of a-d:

diagnosing the subject, e.g., diagnosing the subject as having a cell proliferation-related disorder, e.g., a disorder characterized by unwanted cell proliferation, e.g., cancer, or a precancerous disorder;

staging the subject, e.g., determining the stage of a cell proliferation-related disorder, e.g., a disorder characterized by unwanted cell proliferation, e.g., cancer, or a precancerous disorder;

providing a prognosis for the subject, e.g., providing a prognosis for a cell proliferation-related disorder, e.g., a disorder characterized by unwanted cell proliferation, e.g., cancer, or a precancerous disorder;

determining the efficacy of a treatment, e.g., the efficacy of a chemotherapeutic agent, irradiation or surgery;

determining the efficacy of a treatment with a therapeutic agent, e.g., an inhibitor, described herein;

selecting the subject for a treatment for a cell proliferation-related disorder, e.g., a disorder characterized by unwanted cell proliferation, e.g., cancer, or a precancerous disorder. The selection can be based on the need for a reduction in neoactivity or on the need for amelioration of a condition associated with or resulting from neoactivity. For example, if it is determined that the subject has a cell proliferation-related disorder, e.g., e.g., cancer, or a precancerous disorder characterized by unwanted levels of an alpha hydroxy neoactivity product, e.g., 2HG, e.g., R-2HG, or by an IDH1-97$^{neo}$ mutation, or IDH2-137$^{neo}$ mutation selecting the subject for treatment with a therapeutic agent described herein, e.g., an inhibitor (e.g., a small molecule or a nucleic acid-based inhibitor) of the neoactivity of that mutant (e.g., conversion of alpha-ketoglutarate to 2HG, e.g., R-2HG;

correlating the analysis with an outcome or a prognosis;

providing a value for an analysis on which the evaluation is based, e.g., the value for a parameter correlated to the presence, distribution, or level of an alpha hydroxy neoactivity product, e.g., 2HG, e.g., R-2HG;

providing a recommendation for treatment of the subject; or memorializing a result of, or output from, the method, e.g., a measurement made in the course of performing the method, and optionally transmitting the memorialization to a party, e.g., the subject, a healthcare provider, or an entity that pays for the subject's treatment, e.g., a government, insurance company, or other third party payer.

As described herein, the evaluation can provide information on which a number of decisions or treatments can be based.

Thus, in an embodiment the result of the evaluation, e.g., an unwanted level of an alpha hydroxy neoactivity product, e.g., 2HG, e.g., R-2HG, in a cell or tissue having an IDH1-97$^{neo}$, or IDH2-137$^{neo}$, mutation; the presence of an IDH1-97$^{neo}$, or IDH2-137$^{neo}$, neoactivity, e.g., 2HG neoactivity; the presence of an IDH1-97$^{neo}$, or IDH2-137$^{neo}$, mutant protein (or corresponding RNA) which has, e.g., 2HG neoactivity; the presence of an IDH1-97$^{neo}$ or IDH2-137$^{neo}$, mutation, having, 2HG neoactivity, e.g., an allele disclosed herein, is indicative of:

a cell proliferation-related disorder characterized by an IDH1-97$^{neo}$ or IDH2-137$^{neo}$, mutation, e.g., cancer, e.g., it is indicative of a primary or metastatic lesion;

the stage of a cell proliferation-related disorder characterized by an IDH1-97$^{neo}$ or IDH2-137$^{neo}$, mutation;

a prognosis or outcome for a cell proliferation-related disorder characterized by an IDH1-97$^{neo}$ or IDH2-137$^{neo}$, mutation, e.g., it is indicative of a less aggressive form of the disorder, e.g., cancer. E.g., in the case of glioma disorder characterized by an IDH1-97$^{neo}$ or IDH2-137$^{neo}$, mutation, presence of an alpha hydroxy neoactivity product, e.g., 2HG, e.g., R-2HG, can indicate a less aggressive form of the cancer;

the efficacy of a treatment, e.g., the efficacy of a chemotherapeutic agent, irradiation or surgery;

the need of a therapy disclosed herein, e.g., inhibition a neoactivity of an IDH1-97$^{neo}$ or IDH2-137$^{neo}$, mutant. In an embodiment relatively higher levels (or the presence of the IDH1-97$^{neo}$ or IDH2-137$^{neo}$, mutant) is correlated with need of inhibition a neoactivity of an IDH1-97$^{neo}$ or IDH2-137$^{neo}$; mutant; or responsiveness to a treatment. The result can be used as a noninvasive biomarker for clinical response. E.g., elevated levels can be predictive on better outcome in glioma patients (e.g., longer life expectancy).

As described herein, the evaluation can provide for the selection of a subject having a cell proliferation-related disorder characterized by an IDH1-97$^{neo}$ mutation, e.g., IDH1-G97D, or IDH2-137$^{neo}$ mutation.

Thus, in an embodiment the method comprises, e.g., responsive to the analysis of one or more of a-d, selecting a subject, e.g., for a treatment. The subject can be selected on a basis described herein, e.g., on the basis of:

said subject being at risk for, or having, higher than normal levels of an alpha hydroxy neoactivity product, e.g., 2-hydroxyglutarate (e.g., R-2HG) in cell having a cell proliferation-related disorder, e.g., a leukemia such as AML or ALL, e.g., B-ALL or T-ALL, or a tumor lesion, e.g., colorectal cancer, a glioma or a prostate tumor;

said subject having a proliferation-related disorder characterized by an IDH1-97$^{neo}$, mutation, e.g., IDH1-G97D, or IDH2-137$^{neo}$ mutation, having 2HG neoactivity;

said subject having an IDH1-97$^{neo}$ mutation, e.g., IDH1-G97D, or IDH2-137$^{neo}$ mutation;

said subject having a proliferation-related disorder;

said subject being in need of, or being able to benefit from, a therapeutic agent of a type described herein;

said subject being in need of, or being able to benefit from, a compound that inhibits alpha hydroxy neoactivity, e.g., 2HG neoactivity;

said subject being in need of, or being able to benefit from, a compound that lowers the level of an alpha hydroxy neoactivity product, e.g., 2HG, e.g., R-2HG;

said subject being in need of, or being able to benefit from, an antiglycolytic agent or an anti-oxidant, e.g., to ameliorate the effects of an unwanted alpha hydroxy neoactivity product, e.g., 2HG. e.g., R-2HG.

said subject being in need of, or being able to benefit from, an treatment that ameliorates an effect of the competition of an alpha hydroxy neoactivity product, e.g., 2HG, e.g., R-2HG, with a cellular component, e.g., alpha ketoglutarate, for interaction with a cellular component.

said subject being in need of, or being able to benefit from, a therapeutic agent that makes the 2HG, e.g., R-2HG, more toxic to cells, e.g., by modulating an enzyme that results in converting 2HG, e.g., R-2HG, inot a more toxic substance, e.g., where the 2 HG, e.g., R-2HG, acts as a prodrug.

In an embodiment evaluation comprises selecting the subject having a cell proliferation-related disorder characterized by an IDH1-97$^{neo}$ mutation, e.g., IDH1-G97D, or IDH2-137$^{neo}$ mutation, e.g., for treatment with an anti-neoplastic agent, on the establishment of, or determination that, the subject has unwanted alpha hydroxy neoactivity product, e.g., 2HG, e.g., R-2HG, or unwanted alpha hydroxy neoactivity, e.g., 2HG neoactivity, or that the subject is in need of inhibition of a neoactivity of an an IDH1-97$^{neo}$, e.g., IDH1-G97D, or IDH2-137$^{neo}$, mutant described herein.

The evaluations provided for by methods described herein allow the selection of optimal treatment regimens for subjects having a cell proliferation-related disorder characterized by an IDH1-97$^{neo}$ mutation, e.g., IDH1-G97D, or IDH2-137$^{neo}$ mutation.

Thus, in an embodiment the method comprises, e.g., responsive to the analysis of one or more of a-d, selecting a treatment for the subject having a cell proliferation-related disorder characterized by an IDH1-97$^{neo}$ mutation, e.g., IDH1-G97D, or IDH2-137$^{neo}$ mutation, e.g., selecting a treatment on a basis disclosed herein. The treatment can be the administration of a therapeutic agent disclosed herein. The treatment can be selected on the basis that:

it us useful in treating a disorder characterized by one or more of alpha hydroxy neoactivity, e.g., 2HG neoactivity, an IDH1-97$^{neo}$, e.g., IDH1-G97D, or IDH2-137$^{neo}$, mutant protein having alpha hydroxy neoactivity, e.g., 2HG neoactivity (or a corresponding RNA);

it is useful in treating a disorder characterized by an IDH1-97$^{neo}$ mutant, or IDH2-137$^{neo}$, which encodes a protein with 2HG neoactivity, e.g., an allele disclosed herein, in cells characterized by a cell proliferation-related disorder from the subject;

it reduces the level of an alpha hydroxy neoactivity product, e.g., 2HG, e.g., R-2HG;

it reduces the level of alpha hydroxy neoactivity, e.g., 2HG neoactivity;

it is useful in treating a cancer having mitochondrial damage associated with increased levels of an unwanted alpha hydroxy neoactivity product, e.g., 2HG, e.g., R-2HG, and is e.g., an antiglycolytic agent or an anti-oxidant; or it is useful in treating a cancer having levels of an alpha hydroxy neoactivity product, e.g., 2HG, e.g., R-2HG, that compete with a cellular component, e.g., alpha ketoglutarate, for interaction with a cellular component.

In an embodiment evaluation comprises selecting the subject, e.g., for treatment.

In embodiments the treatment is the administration of a therapeutic agent described herein.

The methods can also include treating a subject having a cell proliferation-related disorder characterized by an IDH1-97$^{neo}$ mutation, e.g., IDH1-G97D or IDH2-137$^{neo}$ mutation, e.g, with a treatment selected in response to, or on the basis of, an evaluation made in the method.

Thus, in an embodiment the method comprises, e.g., responsive to the analysis of one or more of a-d, administering a treatment to the subject, e.g., the administration of a therapeutic agent of a type described herein.

In an embodiment the therapeutic agent comprises nucleic acid, e.g., dsRNA, e.g., a dsRNA described herein.

In an embodiment the therapeutic agent results in lowering the level of a neoactivity product, e.g., an alpha hydroxy neoactivity product, e.g., 2HG, e.g., R-2HG, In an embodiment the method comprises administering a therapeutic agent that lowers neoactivity, e.g., 2HG neoactivity.

In an embodiment the method comprises administering an inhibitor of an enzyme encoded by an IDH1-97$^{neo}$ mutation, e.g., IDH1-G97D, or IDH2-137$^{neo}$ mutation.

In an embodiment the therapeutic agent comprises a nucleic acid-based therapeutic agent, e.g., a dsRNA, e.g., a dsRNA described herein.

In an embodiment the therapeutic agent is an inhibitor, e.g., a polypeptide, peptide, or small molecule (e.g., a molecule of less than 1,000 daltons), or aptamer, that binds to an IDH1-97$^{neo}$ mutation, e.g., IDH1-G97D, or IDH2-137$^{neo}$ mutation, or wildtype subunit and inhibits neoactivity, e.g., by inhibiting formation of a dimer, e.g., a homodimer of mutant IDH1 subunits or a heterodimer of a mutant and a wildype subunit. In an embodiment the inhibitor is a polypeptide. In an embodiment the polypeptide acts as a dominant negative with respect to the neoactivity of the mutant enzyme. The polypeptide can correspond to full length IDH1 or a fragment thereof. The polypeptide need not be identical with the corresponding residues of wildtype IDH1, but in embodiments has at least 60, 70, 80, 90 or 95% homology with wildtype IDH1.

In an embodiment the therapeutic agent decreases the affinity of an IDH1-97$^{neo}$ mutant, or IDH2-137$^{neo}$ mutant, protein for NADH, NADPH or a divalent metal ion, e.g., $Mg^{2+}$ or $Mn^{2+}$, or decreases the levels or availability of NADH, NADPH or divalent metal ion, e.g., $Mg^{2+}$ or $Mn^{2+}$, e.g., by competing for binding to the mutant enzyme. In an embodiment the enzyme is inhibited by replacing $Mg^{2+}$ or $Mn^{2+}$ with $Ca^{2+}$.

In an embodiment the therapeutic agent is an inhibitor that reduces the level a neoactivity of an IDH1-97$^{neo}$ mutant, e.g., IDH1-G97D, 2HG neoactivity.

In an embodiment the therapeutic agent is an inhibitor that reduces the level of the product of a IDH1-97$^{neo}$ mutant, e.g., IDH1-G97D, e.g., it reduces the level of 2HG, e.g., R-2HG.

In an embodiment the therapeutic agent is an inhibitor that:

inhibits, e.g., specifically, a neoactivity of an IDH1-97$^{neo}$ mutant, e.g., IDH1-G97D, neoactivity described herein, e.g., 2HG neoactivity; or inhibits both the wildtype activity and a neoactivity of IDH1-97$^{neo}$ mutant, e.g., IDH1-G97D, e.g., 2HG neoactivity.

In an embodiment the therapeutic agent is an inhibitor that is selected on the basis that it:

inhibits, e.g., specifically, a neoactivity of an IDH1-97$^{neo}$ mutant, e.g., IDH1-G97D, neoactivity described herein e.g., 2HG neoactivity; or inhibits both the wildtype activity and a neoactivity of an IDH1-97$^{neo}$ mutant, e.g., IDH1-G97D, neoactivity described herein, e.g., 2HG neoactivity.

In an embodiment the therapeutic agent is an inhibitor that reduces the amount of IDH1-97$^{neo}$ mutant, e.g., IDH1-G97D, mutant, protein or mRNA.

In an embodiment the therapeutic agent is an inhibitor that interacts directly with, e.g., it binds to, IDH1-97$^{neo}$ mutant, e.g., IDH1-G97D, mutant, mRNA.

In an embodiment the therapeutic agent is an inhibitor that interacts directly with, e.g., it binds to, IDH1-97$^{neo}$ mutant, e.g., IDH1-G97D, mutant protein.

In an embodiment the therapeutic agent is an inhibitor that reduces the amount of neoactive enzyme activity, e.g., by interacting with, e.g., binding to, IDH1-97$^{neo}$ mutant, e.g., IDH1-G97D, mutant, protein. In an embodiment the inhibitor is other than an antibody.

In an embodiment the therapeutic agent is an inhibitor that is a small molecule and interacts with, e.g., binds, IDH1-97$^{neo}$ mutant, e.g., IDH1-G97D, mutant, mRNA.

In an embodiment the therapeutic agent is an inhibitor that interacts directly with, e.g., binds, either the mutant IDH1-97$^{neo}$, e.g., IDH1-G97D, mutant protein or interacts directly with, e.g., binds, the IDH1-97$^{neo}$ mutant, e.g., IDH1-G97D, mutant, mRNA.

In an embodiment the therapeutic agent is an inhibitor that reduces the level a neoactivity of an IDH2-137$^{neo}$ mutant, 2HG neoactivity.

In an embodiment the therapeutic agent is an inhibitor that reduces the level of the product of a IDH2-137$^{neo}$ mutant, e.g., it reduces the level of 2HG, e.g., R-2HG.

In an embodiment the therapeutic agent is an inhibitor that:
 inhibits, e.g., specifically, a neoactivity of an IDH2-137$^{neo}$ mutant, neoactivity described herein, e.g., 2HG neoactivity; or
 inhibits both the wildtype activity and a neoactivity of an IDH2-137$^{neo}$ mutant, e.g, 2HG neoactivity.

In an embodiment the therapeutic agent is an inhibitor that is selected on the basis that it:
 inhibits, e.g., specifically, a neoactivity of an IDH2-137$^{neo}$ mutant, neoactivity described herein e.g., 2HG neoactivity; or
 inhibits both the wildtype activity and a neoactivity of an IDH2-137$^{neo}$ mutant, neoactivity described herein, e.g., 2HG neoactivity.

In an embodiment the therapeutic agent is an inhibitor that reduces the amount of IDH2-137$^{neo}$ mutant protein or mRNA.

In an embodiment the therapeutic agent is an inhibitor that interacts directly with, e.g., it binds to, IDH2-137$^{neo}$ mutant mRNA.

In an embodiment the therapeutic agent is an inhibitor that interacts directly with, e.g., it binds to, IDH2-137$^{neo}$ mutant protein.

In an embodiment the therapeutic agent is an inhibitor that reduces the amount of neoactive enzyme activity, e.g., by interacting with, e.g., binding to, IDH2-137$^{neo}$ mutant protein. In an embodiment the inhibitor is other than an antibody In an embodiment the therapeutic agent is an inhibitor that is a small molecule and interacts with, e.g., binds, IDH2-137$^{neo}$ mutant, mRNA.

In an embodiment the therapeutic agent is an inhibitor that interacts directly with, e.g., binds, either the mutant IDH2-137$^{neo}$ mutant protein or interacts directly with, e.g., binds, the IDH2-137$^{neo}$ mutant, mRNA.

In an embodiment the therapeutic agent is a cellular structural analog of a neoactivity product, or a prodrug thereof, e.g., as described in the section entitled "Cellular structural analogs of neoactivity products, and prodrugs thereof" elsewhere herein.

In an embodiment the therapeutic agent is an antiglycolytic agent, e.g., an anti-glycolytic agent described in the section entitled "Anti-glycolytic compounds" herein.

In an embodiment the therapeutic agent is an antioxidant, e.g., an antioxidant agent described in the section entitled "Antioxidants" herein.

In an embodiment the therapeutic agent is a hypomethylating agent, e.g., an hypomethylating agent described in the section entitled "Hypomethylating Agents" herein.

In an embodiment the therapeutic agent makes the 2HG, e.g., R-2HG, more toxic to cells, e.g., by modulating an enzyme that results in converting 2HG, e.g., R-2HG, inot a more toxic substance, e.g., where the 2 HG, e.g., R-2HG, acts as a prodrug.

In an embodiment the therapeutic agent is administered.

In an embodiment the treatment: inhibits, e.g., specifically, a neoactivity of an IDH1-97$^{neo}$ mutation, e.g., IDH1-G97D, or IDH2-137$^{neo}$ mutation; or inhibits both the wildtype and activity and a neoactivity of an IDH1-97$^{neo}$ mutation, e.g., IDH1-G97D. In an embodiment, the subject is subsequently evaluated or monitored by a method described herein, e.g., the analysis of the presence, distribution, or level of an alpha hydroxy neoactivity product, e.g., 2HG, e.g., R-2HG, e.g., to evaluate response to the treatment or progression of disease.

In an embodiment the treatment is selected on the basis that it: inhibits, e.g., specifically, a neoactivity of an IDH1-97$^{neo}$ mutation, e.g., IDH1-G97D, or IDH2-137$^{neo}$ mutation, e.g., 2HG neoactivity; or inhibits both the wildtype and activity and a neoactivity of an IDH1-97$^{neo}$ mutation, e.g., IDH1-G97D, or IDH2-137$^{neo}$ mutation.

In an embodiment, the method comprises determining the possibility of a mutation other than an IDH1-97$^{neo}$ mutation, e.g., IDH1-G97D, or IDH2-137$^{neo}$ mutation. In embodiments a relatively high level of 2HG, e.g., R-2HG is indicative of another mutation.

In an embodiment, which embodiment includes selecting or administering a treatment for the subject having a cell proliferation-related disorder characterized by an IDH1-97$^{neo}$ mutation, e.g., IDH1-G97D, or IDH2-137$^{neo}$ mutation, wherein the subject:
 has not yet been treated for the subject the cell proliferation-related disorder and the selected or administered treatment is the initial or first line treatment;
 has already been treated for the cell proliferation-related and the selected or administered treatment results in an alteration of the existing treatment;
 has already been treated for the cell proliferation-related, and the selected treatment results in continuation of the existing treatment; or
 has already been treated for the cell proliferation-related disorder and the selected or administered treatment is different, e.g., as compared to what was administered prior to the evaluation or to what would be administered in the absence of elevated levels of an alpha hydroxy neoactivity product, e.g., 2HG, e.g., R-2HG.

In an embodiment, which embodiment includes selecting or administering a treatment for the subject, the selected or administered treatment can comprise:
 a treatment which includes administration of a therapeutic agent at different, e.g., a greater (or lesser) dosage (e.g., different as compared to what was administered prior to the evaluation or to what would be administered in the absence of elevated levels of an alpha hydroxy neoactivity product, e.g., 2HG, e.g., R-2HG);
 a treatment which includes administration of a therapeutic agent at a different frequency, e.g., more or less frequently, or not at all (e.g., different as compared to what was administered prior to the evaluation or to what would be administered in the absence of elevated levels of an alpha hydroxy neoactivity product, e.g., 2HG, e.g., R-2HG); or
 a treatment which includes administration of a therapeutic agent in a different therapeutic setting (e.g., adding or deleting a second treatment from the treatment regimen) (e.g., different as compared to what was administered prior to the evaluation or to what would be administered in the absence of elevated levels of an alpha hydroxy neoactivity product, e.g., 2HG, e.g., R-2HG).

Methods of evaluating a subject described herein can comprise evaluating a neoactivity genotype or phenotype. Methods of obtaining and analyzing samples, and the in vivo analysis in subjects, described elsewhere herein, e.g., in the section entitled, "Methods of evaluating samples and/or subjects," can be combined with this method.

In an embodiment the method comprises:

subjecting the subject (e.g., a subject not having 2-hydroxyglutaric aciduria) to imaging and/or spectroscopic analysis, e.g., magnetic resonance-based analysis, e.g., MRI and/or MRS e.g., imaging analysis, to provide a determination of the presence, distribution, or level of an alpha hydroxy neoactivity product, e.g., 2HG, e.g., R-2HG, e.g., as associated with a tumor, e.g., a glioma, in the subject having a cell proliferation-related disorder characterized by an IDH1-97$^{neo}$ mutation, e.g., IDH1-G97D, or IDH2-137$^{neo}$ mutation;

optionally storing a parameter related to the determination, e.g., the image or a value related to the image from the imaging analysis, in a tangible medium; and responsive to the determination, performing one or more of: correlating the determination with outcome or with a prognosis; providing an indication of outcome or prognosis; providing a value for an analysis on which the evaluation is based, e.g., the presence, distribution, or level of an alpha hydroxy neoactivity product, e.g., 2HG, e.g., R-2HG; providing a recommendation for treatment of the subject; selecting a course of treatment for the subject, e.g., a course of treatment described herein, e.g., selecting a course of treatment that includes inhibiting a neoactivity of an IDH1-97$^{neo}$ mutation, e.g., IDH1-G97D, or IDH2-137$^{neo}$ mutation; administering a course of treatment to the subject, e.g., a course of treatment described herein, e.g., a course of treatment that includes inhibiting a neoactivity of an IDH1-97$^{neo}$ mutation, e.g., IDH1-G97D, or IDH2-137$^{neo}$ mutation; and memorializing a result of the method or a measurement made in the course of the method, e.g., one or more of the above and/or transmitting memorialization of one or more of the above to a party, e.g., the subject, a healthcare provider, or an entity that pays for the subject's treatment, e.g., a government, insurance company, or other third party payer.

In an embodiment the method comprises confirming or determining, e.g., by direct examination or evaluation of the subject, or sample e.g., tissue or bodily fluid (e.g., blood (e.g., blood plasma), urine, lymph, or cerebrospinal fluid) therefrom, (e.g., by DNA sequencing or immuno analysis or evaluation of the presence, distribution or level of an alpha hydroxy neoactivity product, e.g., 2HG, e.g., R-2HG), or receiving such information about the subject, that the subject has a cancer characterized by an IDH1-97$^{neo}$ mutation, e.g., IDH1-G97D, or IDH2-137$^{neo}$ mutation.

In an embodiment, prior to or after treatment, the method includes evaluating the growth, size, weight, invasiveness, stage or other phenotype of the cell proliferation-related disorder.

In an embodiment the cell proliferation-related disorder is a tumor of the CNS, e.g., a glioma, a leukemia, e.g., AML or ALL, e.g., B-ALL or T-ALL, colorectal cancer, prostate cancer, or myelodysplasia or myelodysplastic syndrome and the evaluation is a or b.

In an embodiment the cell proliferation-related disorder is colorectal cancer and the evaluation is a or b.

In an embodiment, a subject is subjected to MRS and the evaluation comprises evaluating the presence or elevated amount of a peak correlated to or corresponding to 2HG, e.g., R-2HG, as determined by magnetic resonance. For example, a subject can be analyzed for the presence and/or strength of a signal at about 2.5 ppm to determine the presence and/or amount of 2HG, e.g., R-2HG in the subject.

In an embodiment the method comprises obtaining a sample from the subject and analyzing the sample, or analyzing the subject, e.g., by imaging the subject and optionally forming a representation of the image on a computer.

In an embodiment the results of the analysis is compared to a reference.

In an embodiment a value for a parameter correlated to the presence, distribution, or level, e.g., of 2HG, e.g., R-2HG, is determined. It can be compared with a reference value, e.g., the value for a reference subject not having abnormal presence, level, or distribution, e.g., a reference subject cell not having an IDH1-97$^{neo}$ e.g., IDH1-G97D, mutation.

In an embodiment the method comprises determining if an IDH1-97$^{neo}$ mutation, e.g., IDH1-G97D, or IDH2-137$^{neo}$ mutation, is present. The determination can comprise sequencing a nucleic acid, e.g., genomic DNA or cDNA, from an affected cell, which encodes the relevant amino acid(s). The mutation can be a deletion, insertion, rearrangement, or substitution. The mutation can involve a single nucleotide, e.g., a single substitution, or more than one nucleotide, e.g., a deletion of more than one nucleotides.

In an embodiment the subject does not have, or has not been diagnosed as having, 2-hydroxyglutaric aciduria.

In an embodiment a product of the neoactivity is 2-HG, e.g., R-2HG, which acts as a metabolite. In another embodiment a product of the neoactivity is 2HG, e.g., R-2HG, which acts as a toxin, e.g., a carcinogen.

In an embodiment the disorder is other than a solid tumor. In an embodiment the disorder is a tumor that, at the time of diagnosis or treatment, does not have a necrotic portion. In an embodiment the disorder is a tumor in which at least 30, 40, 50, 60, 70, 80 or 90% of the tumor cells carry an IDH1-97$^{neo}$ mutation, e.g., IDH1-G97D, or IDH2-137$^{neo}$ mutation, having 2HG neoactivity, at the time of diagnosis or treatment.

In an embodiment the cell proliferation-related disorder is a cancer characterized by an IDH1-97$^{neo}$ mutation, e.g., IDH1-G97D, or IDH2-137$^{neo}$ mutation, e.g., a cancer described herein. In an embodiment the cancer is characterized by increased levels of an alpha hydroxy neoactivity product, 2HG, e.g., R-2HG, as compared to non-diseased cells of the same type.

In an embodiment the method comprises selecting a subject having cancer, on the basis of the cancer being characterized by an IDH1-97$^{neo}$ mutation, e.g., IDH1-G97D (the sequence of IDH1 is provided in (SEQ ID NO:8)) or IDH2-137$^{neo}$ mutation.

In an embodiment the method comprises selecting a subject having a glioma, characterized by an IDH1-97$^{neo}$ mutation, e.g., IDH1-G97D, or IDH2-137$^{neo}$ mutation, on the basis of the cancer being characterized by unwanted levels of an alpha hydroxy neoactivity, product, e.g., 2HG, e.g., R-2HG.

In an embodiment the cell proliferation-related disorder is a tumor of the CNS, e.g., a glioma, e.g., wherein the tumor is characterized by an IDH1-97$^{neo}$ mutation, e.g., IDH1-G97D, or IDH2-137$^{neo}$ mutation. Gliomas include astrocytic tumors, oligodendroglial tumors, oligoastrocytic tumors, anaplastic astrocytomas, and glioblastomas. In an embodiment the tumor is characterized by increased levels of an alpha hydroxy neoactivity product, e.g., 2HG, e.g., R-2HG, as compared to non-diseased cells of the same type.

In an embodiment the method comprises selecting a subject having a glioma, on the basis of the cancer being characterized by an IDH1-97$^{neo}$ mutation, e.g., IDH1-G97D, or IDH2-137$^{neo}$ mutation.

In an embodiment the method comprises selecting a subject having a glioma characterized by an IDH1-97$^{neo}$ mutation, e.g., IDH1-G97D, or IDH2-137$^{neo}$ mutation on the basis of the cancer being characterized by unwanted levels of an alpha hydroxy neoactivity, product, e.g., 2HG, e.g., R-2HG.

In an embodiment the cell proliferation-related disorder is localized or metastatic prostate cancer, e.g., prostate adenocarcinoma, e.g., wherein the cancer is characterized by an IDH1-97$^{neo}$ mutation, e.g., IDH1-G97D, or IDH2-137$^{neo}$ mutation. In an embodiment the cancer is characterized by increased levels of an alpha hydroxy neoactivity product, e.g., 2HG, e.g., R-2HG, as compared to non-diseased cells of the same type.

In an embodiment the method comprises selecting a subject having prostate cancer, e.g., prostate adenocarcinoma, wherein the cancer is characterized by an IDH1-97$^{neo}$ mutation, e.g., IDH1-G97D, or IDH2-137$^{neo}$ mutation.

In an embodiment the method comprises selecting a subject having prostate cancer, e.g., prostate adenocarcinoma, on the basis of the cancer being characterized by an IDH1-97$^{neo}$ mutation, e.g., IDH1-G97D, or IDH2-137$^{neo}$ mutation.

In an embodiment the method comprises selecting a subject having prostate cancer characterized by an IDH1-97$^{neo}$ mutation, e.g., IDH1-G97D, or IDH2-137$^{neo}$ mutation on the basis of the cancer being characterized by unwanted levels of an alpha hydroxy neoactivity product, e.g., 2HG, e.g., R-2HG.

In an embodiment the cell proliferation-related disorder is a hematological cancer, e.g., a leukemia, e.g., AML, or ALL, wherein the hematological cancer is characterized by an IDH1-97$^{neo}$ mutation, e.g., IDH1-G97D, or IDH2-137$^{neo}$ mutation. In an embodiment the cancer is characterized by increased levels of an alpha hydroxy neoactivity product, e.g., 2HG, e.g., R-2HG, as compared to non-diseased cells of the same type.

In an embodiment the cell proliferation-related disorder is acute lymphoblastic leukemia (e.g., an adult or pediatric form), e.g., wherein the acute lymphoblastic leukemia (sometimes referred to herein as ALL) is characterized by an IDH1-97$^{neo}$ mutation, e.g., IDH1-G97D, or IDH2-137$^{neo}$ mutation. The ALL can be, e.g., B-ALL or T-ALL. In an embodiment the cancer is characterized by increased levels of a 2 alpha hydroxy neoactivity product, e.g., HG, e.g., R-2HG, as compared to non-diseased cells of the same type.

In an embodiment the method comprises selecting a subject having ALL, e.g., B-ALL or T-ALL, characterized by an IDH1-97$^{neo}$ mutation, e.g., IDH1-G97D, SEQ ID NO:8, or IDH2-137$^{neo}$ mutation.

In an embodiment the method comprises selecting a subject ALL, e.g., B-ALL or T-ALL, on the basis of cancer being characterized by an IDH1-97$^{neo}$ mutation, e.g., IDH1-G97D, or IDH2-137$^{neo}$ mutation.

In an embodiment the method comprises selecting a subject having ALL, e.g., B-ALL or T-ALL, characterized by an IDH1-97$^{neo}$ mutation, e.g., IDH1-G97D, or IDH2-137$^{neo}$ mutation, on the basis of the cancer being characterized by unwanted levels of an alpha hydroxy neoactivity product, e.g., 2HG, e.g., R-2HG.

In an embodiment the cell proliferation-related disorder is acute myelogenous leukemia (e.g., an adult or pediatric form), e.g., wherein the acute myelogenous leukemia (sometimes referred to herein as AML) is characterized by an IDH1-97$^{neo}$ mutation, e.g., IDH1-G97D, or IDH2-137$^{neo}$ mutation. In an embodiment the cancer is characterized by increased levels of an alpha hydroxy neoactivity product, e.g., 2HG, e.g., R-2HG, as compared to non-diseased cells of the same type.

In an embodiment the method comprises selecting a subject having acute myelogenous lymphoplastic leukemia (AML) characterized by an IDH1-97$^{neo}$ mutation, e.g., IDH1-G97D SEQ ID NO:8, or IDH2-137$^{neo}$ mutation.

In an embodiment the method comprises selecting a subject having acute myelogenous lymphoplastic leukemia (AML) on the basis of cancer being characterized by an IDH1-97$^{neo}$ mutation, e.g., IDH1-G97D, or IDH2-137$^{neo}$ mutation.

In an embodiment the method comprises selecting a subject having acute myelogenous lymphoplastic leukemia (AML) characterized by an IDH1-97$^{neo}$ mutation, e.g., IDH1-G97D or IDH2-137$^{neo}$ mutation on the basis of the cancer being characterized by unwanted levels of an alpha hydroxy neoactivity product, e.g., 2HG, e.g., R-2HG.

In an embodiment the method further comprises evaluating the subject for the presence of a mutation in the NRAS or NPMc gene.

In an embodiment the cell proliferation-related disorder is myelodysplasia or myelodysplastic syndrome, e.g., wherein the myelodysplasia or myelodysplastic syndrome is characterized by an IDH1-97$^{neo}$ mutation, e.g., IDH1-G97D, or IDH2-137$^{neo}$ mutation. In an embodiment the disorder is characterized by increased levels of an alpha hydroxy neoactivity product, e.g., 2HG, e.g., R-2HG, as compared to non-diseased cells of the same type.

In an embodiment the method comprises selecting a subject having myelodysplasia or myelodysplastic syndrome, wherein the disorder is characterized by an IDH1-97$^{neo}$ mutation, e.g., IDH1-G97D, or IDH2-137$^{neo}$ mutation.

In an embodiment the method comprises selecting a subject having myelodysplasia or myelodysplastic syndrome, on the basis of the disorder being characterized by an IDH1-97$^{neo}$ mutation, e.g., IDH1-G97D, or IDH2-137$^{neo}$ mutation.

In an embodiment the method comprises selecting a subject having myelodysplasia or myelodysplastic syndrome characterized by an IDH1-97$^{neo}$ mutation, e.g., IDH1-G97D, or IDH2-137$^{neo}$ mutation, on the basis of the cancer being characterized by unwanted levels of an alpha hydroxy neoactivity product, e.g., 2HG, e.g., R-2HG.

In an embodiment the cell proliferation-related disorder is colorectal cancer, e.g., wherein the cancer is characterized by an IDH1-97$^{neo}$ mutation, e.g., IDH1-G97D, or IDH2-137$^{neo}$ mutation. In an embodiment the cancer is characterized by increased levels of an alpha hydroxy neoactivity product, e.g., 2HG, e.g., R-2HG, as compared to non-diseased cells of the same type.

In an embodiment the method comprises selecting a subject having colorectal cancer, wherein the cancer is characterized by an IDH1-97$^{neo}$ mutation, e.g., IDH1-G97D, or IDH2-137$^{neo}$ mutation.

In an embodiment the method comprises selecting a subject having colorectal cancer, on the basis of the cancer being characterized by an IDH1-97$^{neo}$ mutation, e.g., IDH1-G97D, or IDH2-137$^{neo}$ mutation.

In an embodiment the method comprises selecting a subject having colorectal cancer characterized by an IDH1-97$^{neo}$ mutation, e.g., IDH1-G97D, or IDH2-137$^{neo}$ mutation, on the basis of the cancer being characterized by unwanted levels of an alpha hydroxy neoactivity product, e.g., 2HG, e.g., R-2HG.

A method of treating an aciduria subject (e.g., a 2-hydroxyglutaric aciduria subject) comprising:
determining if the subject has a neoactive mutation at residue 97 of IDH1, e.g., an IDH1-G97D, or an IDH2-137$^{neo}$, mutation, e.g., a germline mutation, having 2HG neoactivity, or establishing the absence of a mutation of 2HG dehydrogenase together with elevated levels of 2HG; and responsive to said determination, e.g., responsive to the presence of said mutation, administering one or more of: an inhibitor of the, neoactivity; a treatment which decreases the competition between 2HG and a cellular structural analog of 2HG; an anti-glycolytic agent; an antioxidant; or a hypomethylating agent, thereby treating said subject.

In some preferred embodiments, the method includes determining if the subject has an IDH1-97$^{neo}$ mutation, e.g., IDH1-G97D, or IDH2-137$^{neo}$ mutation, e.g., a germline mutation, having 2HG neoactivity.

A subject can be determined to have an IDH1-97$^{neo}$ mutation, e.g., IDH1-G97D, or IDH2-137$^{neo}$ mutation using methods described herein.

In another aspect, the invention features a method of evaluating an aciduria subject (e.g., a 2-hydroxyglutaric aciduria subject), the method comprising, determining if the subject has an IDH, e.g., IDH1 or IDH2, mutation, (e.g., a germline mutation such as a mutation described herein), having 2HG neoactivity, or establishing the absence of a mutation of 2HG dehydrogenase together with elevated levels of 2HG. The determination can be made using methods described herein.

In some embodiments, the subject does not have or has not been diagnosed with a cancer, for example, a cancer of the CNS.

In some embodiments, responsive to said determination, e.g., responsive to the presence of said mutation, the method comprises administering one or more of: an inhibitor of IDH, e.g., IDH1 or IDH2, neoactivity; a treatment which decreases the competition between 2HG and a cellular structural analog of 2HG; an anti-glycolytic agent; an antioxidant; or a hypomethylating agent, thereby treating said subject.

In another aspect the invention features a pharmaceutical composition of a therapeutic agent, e.g., inhibitor (e.g., a small molecule or a nucleic acid-based inhibitor) described herein.

In another aspect, the invention features, a method of evaluating a candidate compound for the ability to inhibit a neoactivity of an IDH1-97$^{neo}$ mutation, e.g., IDH1-G97D or IDH2-137$^{neo}$ mutation, for use as an anti-proliferative or anti-cancer agent. In an embodiment the neoactivity is 2HG neoactivity. The method comprises:

optionally supplying the candidate compound;

contacting the candidate compound with an IDH1-97$^{neo}$ mutant enzyme, e.g., an IDH1-G97D enzyme, or IDH2-137$^{neo}$ mutant enzyme, (or with a cell or cell lysate comprising the same); and evaluating the ability of the candidate compound to modulate, e g, inhibit or promote, the neoactivity,
thereby evaluating the candidate compound.

In an embodiment the method includes evaluating the ability of the candidate compound to inhibit the neoactivity.

In an embodiment the method further comprises evaluating the ability of the candidate compound to inhibit the forward reaction of IDH1, the conversion of isocitrate to α-ketoglutarate (or an intermediate thereof, including the reduced hydroxy intermediate).

In an embodiment, the contacting step comprises contacting the candidate compound with a cell, or a cell lysate thereof, wherein the cell comprises a mutant enzyme encoded by an IDH1-97$^{neo}$ mutant, e.g., IDH1-G97D or IDH2-137$^{neo}$ mutant, gene.

In an embodiment, the cell comprises an IDH1-97$^{neo}$ mutation, e.g., IDH1-G97D, or IDH2-137$^{neo}$ mutation.

In an embodiment, the cell includes a heterologous copy of an IDH1-97$^{neo}$ mutation, e.g., IDH1-G97D, or IDH2-137$^{neo}$ mutation. (Heterologous copy refers to a copy introduced or formed by a genetic engineering manipulation.)

In an embodiment, the cell is transfected (e.g., transiently or stably transfected) or transduced (e.g., transiently or stably transduced) with a nucleic acid sequence encoding an IDH1-97$^{neo}$ mutation, e.g., IDH1-G97D, or IDH2-137$^{neo}$ mutation. In an embodiment, the IDH1-97$^{neo}$, e.g., IDH1-G97D or IDH2-137$^{neo}$, enzyme is epitope-tagged, e.g., myc-tagged.

In an embodiment, the cell is a cultured cell, e.g., a primary cell, a secondary cell, or a cell line. In an embodiment, the cell is a cancer cell, e.g., a glioma cell (e.g., a glioma, e.g., a glioblastoma cell), a prostate cancer cell, a colon cancer cell, a leukemia cell (e.g., an ALL, e.g., B-ALL or T-ALL, cell or AML cell), a cell characterized by myelodysplasia or myelodysplastic syndrome, a fibrosarcoma cancer cell, a paraganglioma cancer cell, a myeloma cancer cell, a thyroid cancer cell, a sarcoma or osteosarcoma cancer cell, or a cell characterized by myeloproliferative neoplasms (e.g., CML). In embodiment, the cell is a 293T cell, a U87MG cell, or an LN-18 cell (e.g., ATCC HTB-14 or CRL-2610).

In an embodiment, the cell is from a subject, e.g., a subject having cancer, e.g., a cancer characterized by an IDH1-97$^{neo}$ mutation, e.g., IDH1-G97D, or IDH2-137$^{neo}$ mutation.

In an embodiment, the evaluating step comprises evaluating the presence and/or amount of an alpha hydroxy neoactivity product, e.g., 2HG, e.g., R-2HG, e.g., in the cell lysate or culture medium, e.g., by LC-MS.

In an embodiment, the evaluating step comprises evaluating the presence and/or amount of an alpha hydroxy neoactivity, e.g., 2HG neoactivity, in the cell lysate or culture medium.

In an embodiment, the method further comprises evaluating the presence/amount one or more of TCA metabolite(s), e.g., citrate, α-KG, succinate, fumarate, and/or malate, e.g., by LC-MS, e.g., as a control.

In an embodiment, the method further comprises evaluating the oxidation state of NADPH, e.g., the absorbance at 340 nm, e.g., by spectrophotometer.

In an embodiment, the method further comprises evaluating the ability of the candidate compound to inhibit a second enzymatic activity, e.g., the forward reaction of non-mutant or wild type IDH1, the conversion of isocitrate to α-ketoglutarate (or an intermediate thereof, including the reduced hydroxy intermediate).

In an embodiment, the candidate compound is a small molecule, a polypeptide, peptide, a carbohydrate based molecule, or an aptamer (e.g., a nucleic acid aptamer, or a peptide aptamer). The method can be used broadly and can, e.g., be used as one or more of a primary screen, to confirm candidates produced by this or other methods or screens, or generally to guide drug discovery or drug candidate optimization.

In an embodiment, the method comprises evaluating, e.g., confirming, the ability of a candidate compound (e.g., a candidate compound which meets a predetermined level of inhibition in the evaluating step) to inhibit IDH1-97$^{neo}$ neoactivity in a second assay.

In an embodiment, the second assay comprises repeating one or more of the contacting and/or evaluating step(s) of the basic method.

In another embodiment, the second assay is different from the first. E.g., where the first assay can use a cell or cell lysate or other non-whole animal model the second assay can use an animal model, e.g., a tumor transplant model, e.g., a mouse having an IDH1-97$^{neo}$, e.g., IDH1-G97D or IDH2-137$^{neo}$, mutant cell or tumor transplanted in it. E.g., a U87 cell, or other glioma, e.g., blastoma cell, harboring a transfected IDH1-97$^{neo}$ mutation, e.g., IDH1-G97D, or IDH2-137$^{neo}$ mutation, can be implanted as a xenograft and used in an assay. Primary human glioma or AML tumor cells that expresses an IDH1-97$^{neo}$, e.g., IDH1-G97D, or IDH2-137$^{neo}$, mutant protein can be grafted into mice to allow propagation of the tumor and used in an assay. Other cell lines engineered to express IDH1-97$^{neo}$, e.g., IDH1-G97D, or IDH2-137$^{neo}$, mutant protein can also be used in such assays. A genetically engineered mouse model (GEMM) harboring an IDH1-97$^{neo}$ mutation, e.g., IDH1-G97D, or IDH2-137$^{neo}$ mutation, and optionally another mutation, can also be used in an assay.

In an embodiment the method comprises:
optionally supplying the candidate compound;
contacting the candidate compound with a cell comprising a nucleic acid sequence, e.g., a heterologous sequence, encoding an IDH1-97$^{neo}$ mutant, e.g., IDH1-G97D, or IDH2-137$^{neo}$ mutant; and
evaluating the presence and/or amount of an alpha hydroxy neoactivity product, e.g., 2HG, e.g., R-2HG, in the cell lysate or culture medium, by LC-MS, thereby evaluating the compound.

In an embodiment the result of the evaluation is compared with a reference, e.g., the level of product, e.g., an alpha hydroxy neoactivity product, e.g., 2HG. e.g., R-2HG, in a control cell, e.g., a cell having inserted therein a wild type or non-mutant copy of IDH1.

In another aspect, the invention features, a method of evaluating a candidate compound, e.g., for the ability to inhibit an RNA encoding an IDH1-97$^{neo}$ mutant, e.g., IDH1-G97D, or IDH2-137$^{neo}$ mutant, enzyme for use as an anti-proliferative or anti-cancer agent. In an embodiment the neoactivity is 2HG neoactivity. The method comprises:
optionally supplying the candidate compound, e.g., a nucleic acid based inhibitor (e.g., a dsRNA (e.g., siRNA or shRNA), an antisense, or a microRNA);
contacting the candidate compound with an RNA, e.g., an mRNA, which encodes an IDH1-97$^{neo}$ mutant, e.g., IDH1-G97D, or IDH2-137$^{neo}$ mutant, enzyme (or with a cell or cell lysate comprising the same); and
evaluating the ability of the candidate compound to inhibit the RNA, thereby evaluating the candidate compound. By inhibit the RNA means, e.g., to cleave or otherwise inactivate the RNA.

In an embodiment the RNA encodes a fusion of all or part of an IDH1-97$^{neo}$, e.g., IDH1-G97D, or IDH2-137$^{neo}$ mutant protein to a second protein, e.g., a reporter protein, e.g., a fluorescent protein, e.g., a green or red fluorescent protein.

In an embodiment, the contacting step comprises contacting the candidate compound with a cell, or a cell lysate thereof, wherein the cell comprises RNA encoding an IDH1-97$^{neo}$, e.g., IDH1-G97D, or IDH2-137$^{neo}$ mutant, mutant protein.

In an embodiment, the cell includes a heterologous copy of an IDH1-97$^{neo}$, e.g., IDH1-G97D, or IDH2-137$^{neo}$, mutant gene. (Heterologous copy refers to a copy introduced or formed by a genetic engineering manipulation.) In an embodiment the heterologous gene comprises a fusion to a reporter protein, e.g., a fluorescent protein, e.g., a green or red fluorescent protein.

In an embodiment, the cell is transfected (e.g., transiently or stably transfected) or transduced (e.g., transiently or stably transduced) with a nucleic acid sequence encoding an IDH1-97$^{neo}$, e.g., IDH1-G97D, or IDH2-137$^{neo}$, mutant protein. In an embodiment, the IDH1-97$^{neo}$, e.g., IDH1-G97D, or IDH2-137$^{neo}$, mutant protein, is epitope-tagged, e.g., myc-tagged.

In an embodiment, the cell is a cultured cell, e.g., a primary cell, a secondary cell, or a cell line, which expresses an IDH1-97$^{neo}$, e.g., IDH1-G97D, or IDH2-137$^{neo}$, mutant protein. In an embodiment the cell is a 293T cell which expresses an IDH1-97$^{neo}$, e.g., IDH1-G97D, or IDH2-137$^{neo}$, mutant protein. In an embodiment, the cell is a cancer cell, e.g., a glioma cell (e.g., a glioma, e.g, glioblastoma cell), a prostate cancer cell, a colon cancer cell, a leukemia cell (e.g., an ALL, e.g., B-ALL or T-ALL, cell or AML cell), a cell characterized by myelodysplasia or myelodysplastic syndrome, a fibrosarcoma cancer cell, a paraganglioma cancer cell, a myeloma cancer cell, a thyroid cancer cell, a sarcoma or osteosarcoma cancer cell, or a cell characterized by myeloproliferative neoplasms (e.g., CML), which expresses an IDH1-97$^{neo}$, e.g., IDH1-G97D, or IDH2-137$^{neo}$, mutant protein.

In an embodiment, the cell is from a subject having a cancer characterized by an IDH1-97$^{neo}$, e.g., IDH1-G97D, or IDH2-137$^{neo}$, mutation.

In an embodiment, the method comprises a second assay which comprises repeating one or more of the contacting and/or evaluating step(s) of the basic method.

In another embodiment, the second assay is different from the first. E.g., where the first assay can use a cell or cell lysate or other non-whole animal model the second assay can use an animal model.

In an embodiment the efficacy of the candidate is evaluated by its effect on reporter protein activity.

In another aspect, the invention features, a method of evaluating a candidate compound, e.g., for the ability to inhibit transcription of an RNA encoding an IDH1-97$^{neo}$, e.g., IDH1-G97D, or IDH2-137$^{neo}$, mutant enzyme, e.g., for use as an anti-proliferative or anti-cancer agent. In an embodiment the neoactivity is alpha hydroxy neoactivity, e.g., 2HG neoactivity. The method comprises:
optionally supplying the candidate compound, e.g., a small molecule, polypeptide, peptide, aptamer, a carbohydrate-based molecule or nucleic acid based molecule;
contacting the candidate compound with a system comprising a cell or cell lysate; and
evaluating the ability of the candidate compound to inhibit the translation of an RNA encoding an IDH1-97$^{neo}$, e.g., IDH1-G97D, or IDH2-137$^{neo}$, mutant enzyme, thereby evaluating the candidate compound.

In an embodiment the system comprises a fusion gene encoding of all or part of an IDH1-97$^{neo}$, e.g., IDH1-G97D, or IDH2-137$^{neo}$, mutant protein to a second protein, e.g., a reporter protein, e.g., a fluorescent protein, e.g., a green or red fluorescent protein.

In an embodiment, the cell is a cultured cell, e.g., a primary cell, a secondary cell, or a cell line, which expresses an IDH1-97$^{neo}$, e.g., IDH1-G97D, or IDH2-137$^{neo}$, mutant protein. In an embodiment the cell is a 293T cell which expresses an IDH1-97$^{neo}$, e.g., IDH1-G97D, or IDH2-137$^{neo}$, mutant protein. In an embodiment, the cell is a cancer cell, e.g., a glioma cell (e.g., a glioma, e.g., glioblastoma cell), a prostate cancer cell, a colon cancer cell, a leukemia cell (e.g., an ALL, e.g., B-ALL or T-ALL, cell or AML cell), a cell characterized by myelodysplasia or myelodysplastic syndrome, a fibrosarcoma cancer cell, a paraganglioma cancer cell, a myeloma cancer cell, a thyroid cancer cell, a sarcoma or osteosarcoma cancer cell, or a cell characterized by myeloproliferative neoplasms (e.g., CML), which expresses an IDH1-97$^{neo}$, e.g., IDH1-G97D, or IDH2-137$^{neo}$, mutant protein. In an embodiment, the cell is from a subject having a cancer characterized by an IDH1-97$^{neo}$, e.g., IDH1-G97D, or IDH2-137$^{neo}$, mutation.

In an embodiment, the method comprises a second assay and the second assay comprises repeating the method.

In another embodiment, the second assay is different from the first. E.g., where the first assay can use a cell or cell lysate or other non-whole animal model the second assay can use an animal model In an embodiment the efficacy of the candidate is evaluated by its effect on reporter protein activity.

In another aspect, the invention features a method of evaluating a candidate compound, e.g., a therapeutic agent, or inhibitor, for lowering the activity of an IDH1-97$^{neo}$, e.g., IDH1-G97D, or IDH2-137$^{neo}$, mutant protein in an animal model. The candidate compound can be, e.g., a small molecule, polypeptide, peptide, aptomer, a carbohydrate-based molecule or nucleic acid based molecule. The method comprises, contacting the candidate with the animal model and evaluating the animal model.

In an embodiment evaluating comprises;

determining an effect of the compound on the general health of the animal;

determining an effect of the compound on the weight of the animal;

determining an effect of the compound on liver function, e.g, on a liver enzyme;

determining an effect of the compound on the cardiovascular system of the animal;

determining an effect of the compound on neurofunction, e.g., on neuromuscular control or response;

determining an effect of the compound on eating or drinking;

determining the distribution of the compound in the animal;

determining the persistence of the compound in the animal or in a tissue or organ of the animal, e.g., determining plasma half-life; or determining an effect of the compound on a selected cell in the animal;

determining an effect of the compound on the growth, size, weight, invasiveness or other phenotype of a tumor, e.g., an endogenous tumor or a tumor arising from introduction of cells from the same or a different species.

In an embodiment the animal is a non-human primate, e.g., a cynomolgus monkey or chimpanzee.

In an embodiment the animal is a rodent, e.g., a rat or mouse.

In an embodiment the animal is a large animal, e.g., a dog or pig, other than a non-human primate.

In an embodiment the evaluation is memorialized and optionally transmitted to another party.

In one aspect, the invention provides, a method of evaluating or processing a therapeutic agent that results in a lowering of the level of a neoactive product of an IDH1-97$^{neo}$, e.g., IDH1-G97D, or IDH2-137$^{neo}$, mutant. In an embodiment the neoactivity is 2HG neoactivity and the level of an alpha hydroxy neoactivity product, e.g., 2HG, e.g., R-2HG, is lowered.

The method includes:

providing, e.g., by testing a sample of a therapeutic agent that results in a lowering of the level of a neoactive product of an IDH1-97$^{neo}$, e.g., IDH1-G97D, or IDH2-137$^{neo}$, mutant, a value (e.g., a test value) for a parameter related to a property of the therapeutic agent, e.g., the ability to inhibit the conversion of alpha ketoglutarate to 2 hydroxyglutarate, e.g., R-2 hydroxyglutarate, and, optionally, providing a determination of whether the value determined for the parameter meets a preselected criterion, e.g., is present, or is present within a preselected range, thereby evaluating or processing the therapeutic agent.

In an embodiment the therapeutic agent is approved for use in humans by a government agency, e.g., the FDA.

In an embodiment the parameter is correlated to the ability to inhibit 2HG neoactivity, and, e.g., the therapeutic agent is an inhibitor which binds to an IDH1-97$^{neo}$, e.g., IDH1-G97D, or IDH2-137$^{neo}$, mutant protein and reduces an alpha hydroxy neoactivity, e.g., 2HG neoactivity.

In an embodiment the parameter is correlated to the level of an IDH1-97$^{neo}$, e.g., IDH1-G97D, or IDH2-137$^{neo}$, mutant, and, e.g., the therapeutic agent is an inhibitor which reduces the level of mutant protein.

In an embodiment the parameter is correlated to the level of an RNA that encodes an IDH1-97$^{neo}$, e.g., IDH1-G97D, or IDH2-137$^{neo}$, mutant and, e.g., the therapeutic agent reduces the level of RNA, e.g., mRNA that encodes the mutant protein.

In an embodiment the method includes contacting the therapeutic agent with an IDH1-97$^{neo}$, e.g., IDH1-G97D, or IDH2-137$^{neo}$, mutant protein (or corresponding RNA).

In an embodiment, the method includes providing a comparison of the value determined for a parameter with a reference value or values, to thereby evaluate the therapeutic agent. In an embodiment, the comparison includes determining if a test value determined for the therapeutic agent has a preselected relationship with the reference value, e.g., determining if it meets the reference value. The value need not be a numerical value but, e.g., can be merely an indication of whether an activity is present.

In an embodiment the method includes determining if a test value is equal to or greater than a reference value, if it is less than or equal to a reference value, or if it falls within a range (either inclusive or exclusive of one or both endpoints). In an embodiment, the test value, or an indication of whether the preselected criterion is met, can be memorialized, e.g., in a computer readable record.

In an embodiment, a decision or step is taken, e.g., a sample containing the therapeutic agent, or a batch of the therapeutic agent, is classified, selected, accepted or discarded, released or withheld, processed into a drug product, shipped, moved to a different location, formulated, labeled, packaged, contacted with, or put into, a container, e.g., a gas or liquid tight container, released into commerce, or sold or offered for sale, or a record made or altered to reflect the determination, depending on whether the preselected criterion is met. E.g., based on the result of the determination or whether an activity is present, or upon comparison to a reference standard, the batch from which the sample is taken can be processed, e.g., as just described.

The evaluation of the presence or level of activity can show if the therapeutic agent meets a reference standard.

In an embodiment, methods and compositions disclosed herein are useful from a process standpoint, e.g., to monitor or ensure batch-to-batch consistency or quality, or to evaluate a sample with regard to a reference, e.g., a preselected value.

In an embodiment, the method can be used to determine if a test batch of a therapeutic agent can be expected to have one or more of the properties. Such properties can include a property listed on the product insert of a therapeutic agent, a property appearing in a compendium, e.g., the US Pharmacopea, or a property required by a regulatory agency, e.g., the FDA, for commercial use.

In an embodiment the method includes testing the therapeutic agent for its effect on the wildtype activity of IDH1 protein, and providing a determination of whether the value determined meets a preselected criterion, e.g., is present, or is present within a preselected range.

In an embodiment the method includes:

contacting a therapeutic agent that is an inhibitor of an alpha hydroxy neoactivity, e.g., 2HG neoactivity, with an IDH1-97$^{neo}$, e.g., IDH1-G97D, or IDH2-137$^{neo}$, mutant, determining a value related to the inhibition of an alpha hydroxy neoactivity, e.g., 2HG neoactivity, and comparing the value determined with a reference value, e.g., a range of values, for the inhibition of an alpha hydroxy neoactivity, e.g., 2HG neoactivity. In an embodiment the reference value is an FDA required value, e.g., a release criteria.

In an embodiment the method includes:

contacting a therapeutic agent with an mRNA that an IDH1-97$^{neo}$, e.g., IDH1-G97D, or IDH2-137$^{neo}$, mutant enzyme determining a value related to the inhibition of the mRNA, and, comparing the value determined with a reference value, e.g., a range of values for inhibition of the mRNA. In an embodiment the reference value is an FDA required value, e.g., a release criteria.

In one aspect, the invention features a method of evaluating a sample of a therapeutic agent referred to herein, that includes receiving data with regard to an activity of the therapeutic agent; providing a record which includes said data and optionally includes an identifier for a batch of therapeutic agent; submitting said record to a decision-maker, e.g., a government agency, e.g., the FDA; optionally, receiving a communication from said decision maker; optionally, deciding whether to release market the batch of therapeutic agent based on the communication from the decision maker. In one embodiment, the method further includes releasing, or otherwise processing, e.g., as described herein, the sample.

In another aspect, the invention features, a method of selecting a payment class for treatment with a therapeutic agent described herein, e.g., an inhibitor of an IDH1-97$^{neo}$, e.g., IDH1-G97D, or IDH2-137$^{neo}$, mutant neoactivity, for a subject having a cell proliferation-related disorder. The method includes:

providing (e.g., receiving) an evaluation of whether the subject is positive for an IDH1-97$^{neo}$, e.g., IDH1-G97D, or IDH2-137$^{neo}$, mutant genotype or phenotype; and performing at least one of (1) if the subject is positive selecting a first payment class, and (2) if the subject is a not positive selecting a second payment class.

In an embodiment the selection is memorialized, e.g., in a medical records system.

In an embodiment the method includes evaluation of whether the subject is positive for unwanted levels of an alpha hydroxy neoactivity product, e.g., 2HG, e.g., R-2HG, or neoactivity, e.g., an alpha hydroxy neoactivity, e.g., 2HG neoactivity.

In an embodiment the method includes evaluation of whether the subject is positive for an IDH1-97$^{neo}$, e.g., IDH1-G97D, or IDH2-137$^{neo}$, mutation.

In an embodiment the method includes requesting the evaluation.

In an embodiment the evaluation is performed on the subject by a method described herein.

In an embodiment, the method comprises communicating the selection to another party, e.g., by computer, compact disc, telephone, facsimile, email, or letter.

In an embodiment, the method comprises making or authorizing payment for said treatment.

In an embodiment, payment is by a first party to a second party. In some embodiments, the first party is other than the subject. In some embodiments, the first party is selected from a third party payor, an insurance company, employer, employer sponsored health plan, HMO, or governmental entity. In some embodiments, the second party is selected from the subject, a healthcare provider, a treating physician, an HMO, a hospital, a governmental entity, or an entity which sells or supplies the drug. In some embodiments, the first party is an insurance company and the second party is selected from the subject, a healthcare provider, a treating physician, an HMO, a hospital, a governmental entity, or an entity which sells or supplies the drug. In some embodiments, the first party is a governmental entity and the second party is selected from the subject, a healthcare provider, a treating physician, an HMO, a hospital, an insurance company, or an entity which sells or supplies the drug.

As used herein, a cell proliferation-related disorder is a disorder characterized by unwanted cell proliferation or by a predisposition to lead to unwanted cell proliferation (sometimes referred to as a precancerous disorder). Examples of disorders characterized by unwanted cell proliferation include cancers, e.g., tumors of the CNS, e.g., a glioma. Gliomas include astrocytic tumors, oligodendroglial tumors, oligoastrocytic tumors, anaplastic astrocytomas, and glioblastomas. Other examples include hematological cancers, e.g., a leukemia, e.g., AML (e.g., an adult or pediatric form) or ALL, e.g., B-ALL or T-ALL (e.g., an adult or pediatric form), localized or metastatic prostate cancer, e.g., prostate adenocarcinoma, colon cancer; fibrosarcoma, paraganglioma, myeloma, thyroid cancer, sarcoma, osteosarcoma, or myeloproliferative neoplasms (e.g., CML). Examples of disorders characterized by a predisposition to lead to unwanted cell proliferation include myelodysplasia or myelodysplastic syndrome, which are a diverse collection of hematological conditions marked by ineffective production (or dysplasia) of myeloid blood cells and risk of transformation to AML.

As used herein, specifically inhibits a neoactivity (and similar language), means the neoactivity of the mutant enzyme is inhibited to a significantly greater degree than is the wildtype enzyme activity. By way of example, "specifically inhibits the 2HG neoactivity" means the 2HG neoactivity is inhibited to a significantly greater degree than is the forward reaction (the conversion of isocitrate to alpha ketoglutarate) of wildtype IDH1 activity. In embodiments the neoactivity is inhibited at least 2, 5, 10, or 100 fold more than the wildtype activity. In embodiments an inhibitor that is specific for the 2HG neoactivity of an IDH1-97$^{neo}$, e.g., IDH1-G97D, or IDH2-137$^{neo}$, mutant, will also inhibit another dehydrogenase, e.g., malate dehydrogenase. In other embodiments the specific inhibitor does inhibit other dehydrogenases, e.g., malate dehydrogenase.

As used herein, a cell proliferation-related disorder, e.g., a cancer, characterized by a mutation or allele, means a cell proliferation-related disorder having a substantial number of cells which carry that mutation or allele. In an embodiment at least 10, 25, 50, 75, 90, 95 or 99% of the cell proliferation-related disorder cells, e.g., the cells of a cancer, or a representative, average or typical sample of cancer cells, e.g., from a tumor or from affected blood cells, carry at least one copy of the mutation or allele. In an embodiment the mutation or allele is present as a heterozygote at the indicated frequencies.

As used herein, a "SNP" is a DNA sequence variation occurring when a single nucleotide (A, T, C, or G) in the genome (or other shared sequence) differs between members of a species (or between paired chromosomes in an individual).

As used herein, a subject can be a human or non-human subject. Non-human subjects include non-human primates, rodents, e.g., mice or rats, or other non-human animals.

The details of one or more embodiments of the invention are set forth in the description below. Other features, objects, and advantages of the invention will be apparent from the description and the drawings, and from the claims.

BRIEF DESCRIPTION OF THE DRAWINGS

FIG. 1 depicts DNA sequence verification of pET41a-IDH1 and alignment against published IDH1 CDS. The sequence of IDH1 (CDS) corresponds to SEQ ID NO:5. The sequence of pET41a-IDH1 corresponds to SEQ ID NO:6, and the "consensus" sequence corresponds to SEQ ID NO:7.

FIG. 2 depicts the amino acid sequence of IDH1 (SEQ ID NO:8) as described in GenBank Accession No. NP_005887.2 (GI No. 28178825) (record dated May 10, 2009).

FIG. 2A is the cDNA sequence of IDH1 as presented at GenBank Accession No. NM_005896.2 (Record dated May 10, 2009; GI No. 28178824) (SEQ ID NO:9).

FIG. 2B depicts the mRNA sequence of IDH1 as described in GenBank Accession No. NM_005896.2 (Record dated May 10, 2009; GI No. 28178824) (SEQ ID NO:10).

DETAILED DESCRIPTION

Figure 3:
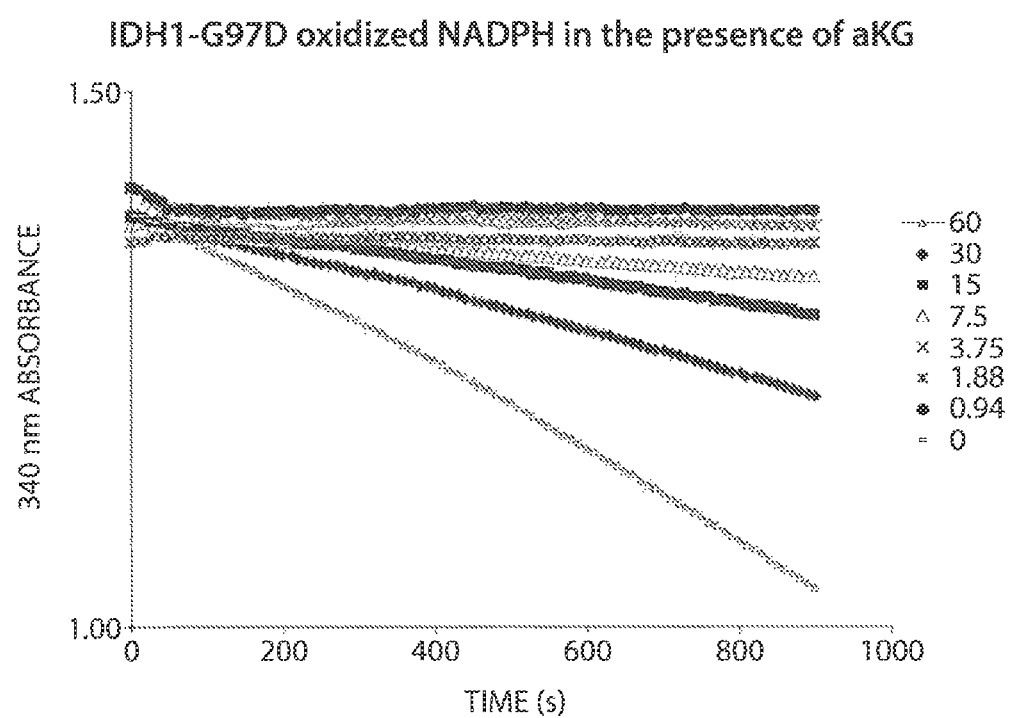
FIG. 3 is a graph depicting the oxidation of NADPH by IDH1-G97D in the presence of alpha-ketoglutarate.

The inventors have discovered that mutations at residue 97 of IDH1, e.g., IDH1-G97D, or IDH2-137$^{neo}$, can have a gain of function, referred to herein as a neoactivity, which can be targeted in the treatment of a cell proliferation-related disorder, e.g., a proliferative disorder such as cancer. Described herein are methods and compositions for the treatment of a cell proliferation-related disorder, e.g., a proliferative disorder such as cancer. The methods include, e.g., treating a subject having a glioma or brain tumor characterized by a preselected IDH1-97$^{neo}$, e.g., IDH1-G97D, or IDH2-137$^{neo}$ mutation, by administering to the subject a therapeutically effective amount of an inhibitor of IDH1. The nucleic acid based inhibitor is, for example, a dsRNA, e.g., a dsRNA that comprises the primary sequences of the sense strand and antisense strands of Tables 1-7. The dsRNA is composed of two separate strands, or a single strand folded to form a hairpin structure (e.g., a short hairpin RNA (shRNA)). In some embodiments, the nucleic acid based inhibitor is an antisense nucleic acid, such as an antisense having a sequence that overlaps, or includes, an antisense sequence provided in Tables 1-7.

Neoactivity of an Enzyme

Neoactivity, as used herein, means an alpha hydroxyl neoactivity in an IDH1-97$^{neo}$, e.g., IDH1-G97D (or IDH2-137$^{neo}$) mutant, that arises as a result of a mutation, e.g., a point mutation, e.g., a substitution, at residue 97 of IDH1 (or in the case of, or IDH2-137$^{neo}$, at residue 137 of IDH2). In an embodiment the neoactivity is substantially absent from wild type or non-mutant enzyme. This is sometimes referred to herein as a first degree neoactivity. An example of a first degree neoactivity is a "gain of function" wherein the mutant enzyme gains a new catalytic activity. In an embodiment the neoactivity is present in wild type or non-mutant enzyme but at a level which is less than 10, 5, 1, 0.1, 0.01 or 0.001% of what is seen in the mutant enzyme. This is sometimes referred to herein as a second degree neoactivity. An example of a second degree neoactivity is a "gain of function" wherein the mutant enzyme has an increase, for example, a 5 fold increase in the rate of a catalytic activity possessed by the enzyme when lacking the mutation.

In some embodiments, a non-mutant form the enzyme, e.g., a wild type form, converts substance A (e.g., isocitrate) to substance B (e.g., α-ketoglutarate), and the neoactivity converts substance B (e.g., α-ketoglutarate) to substance C, sometimes referred to as the neoactivity product (e.g., 2-hydroxyglutarate, e.g., R-2-hydroxyglutarate).

Isocitrate Dehydrogenases

Isocitrate dehydrogenases (IDHs) catalyze the oxidative decarboxylation of isocitrate to 2-oxoglutarate (i.e., α-ketoglutarate). These enzymes belong to two distinct subclasses, one of which utilizes NAD(+) as the electron acceptor and the other NADP(+). Five isocitrate dehydrogenases have been reported: three NAD(+)-dependent isocitrate dehydrogenases, which localize to the mitochondrial matrix, and two NADP(+)-dependent isocitrate dehydrogenases, one of which is mitochondrial and the other predominantly cytosolic. Each NADP(+)-dependent isozyme is a homodimer.

IDH1 (isocitrate dehydrogenase 1 (NADP+), cytosolic) is also known as IDH; IDP; IDCD; IDPC or PICD. The protein encoded by this gene is the NADP(+)-dependent isocitrate dehydrogenase found in the cytoplasm and peroxisomes. It contains the PTS-1 peroxisomal targeting signal sequence. The presence of this enzyme in peroxisomes suggests roles in the regeneration of NADPH for intraperoxisomal reductions, such as the conversion of 2,4-dienoyl-CoAs to 3-enoyl-CoAs, as well as in peroxisomal reactions that consume 2-oxoglutarate, namely the alpha-hydroxylation of phytanic acid. The cytoplasmic enzyme serves a significant role in cytoplasmic NADPH production.

The human IDH1 gene encodes a protein of 414 amino acids. The nucleotide and amino acid sequences for human IDH1 can be found as GenBank entries NM_005896.2 and NP_005887.2 respectively. The nucleotide and amino acid sequences for IDH1 are also described in, e.g., Nekrutenko et al., Mol. Biol. Evol. 15:1674-1684 (1998); Geisbrecht et al., J. Biol. Chem. 274:30527-30533 (1999); Wiemann et al., Genome Res. 11:422-435 (2001); The MGC Project Team, Genome Res. 14:2121-2127 (2004); Lubec et al., Submitted (DEC-2008) to UniProtKB; Kullmann et al., Submitted (JUN-1996) to the EMBL/GenBank/DDBJ databases; and Sjoeblom et al., Science 314:268-274 (2006).

Non-mutant, e.g., wild type, IDH1 catalyzes the oxidative decarboxylation of ioscitrate to α-ketoglutarate thereby reducing NAD$^+$ (NADP$^+$) to NADP(NADPH), e.g., in the forward reaction:

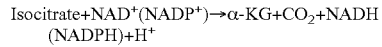
Isocitrate+NAD$^+$(NADP$^+$)→α-KG+CO$_2$+NADH (NADPH)+H$^+$

In some embodiments, an IDH1-97$^{neo}$, e.g., IDH1-G97D mutant, can have the ability to convert α-ketoglutarate to 2-hydroxyglutarate, e.g., R-2-hydroxyglutarate:

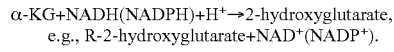
α-KG+NADH(NADPH)+H$^+$→2-hydroxyglutarate, e.g., R-2-hydroxyglutarate+NAD$^+$(NADP$^+$).

In some embodiments, the neoactivity can be the reduction of pyruvate or malate to the corresponding α-hydroxy compounds.

In some embodiments, an IDH1-97$^{neo}$, e.g., IDH1-G97D or IDH2-137$^{neo}$, mutant could lead to an increased level of 2-hydroxyglutarate, e.g., R-2-hydroxyglutarate in a subject. The accumulation of 2-hydroxyglutarate, e.g., R-2-hydroxyglutarate in a subject, e.g., in the brain of a subject, can be harmful. For example, in some embodiments, elevated levels of 2-hydroxyglutarate, e.g., R-2-hydroxyglutarate can lead to and/or be predictive of cancer in a subject such as a cancer of the central nervous system, e.g., brain tumor, e.g., glioma, e.g., glioblastoma multiforme (GBM). Accordingly, in some embodiments, a method described herein includes administering to a subject an inhibitor of the neoactivity Detection of 2-Hydroxyglutarate 2-hydroxyglutarate can be detected, e.g., by LC/MS. To detect secreted 2-hydroxyglutarate in culture media, 500 μL aliquots of conditioned media can be collected, mixed 80:20 with methanol, and centrifuged at 3,000 rpm for 20 minutes at 4 degrees Celsius. The resulting supernatant can be collected and stored at −80 degrees Celsius prior to LC-MS/MS to assess 2-hydroxyglutarate levels. To measure whole-cell associated metabolites, media can be aspirated and cells can be harvested, e.g., at a non-confluent density. A variety of different liquid chromatography (LC) separation methods can be used. Each method can be coupled by negative electrospray ionization (ESI, −3.0 kV) to triple-quadrupole mass spectrometers operating in multiple reaction monitoring (MRM) mode, with MS parameters optimized on infused metabolite standard solutions. Metabolites can be separated by reversed phase chromatography using 10 mM tributylamine as an ion pairing agent in the aqueous mobile phase, according to a variant of a previously reported method (Luo et al. *J Chromatogr A* 1147, 153-64, 2007). One method allows resolution of TCA metabolites: t=0, 50% B; t=5, 95% B; t=7, 95% B; t=8, 0% B, where B refers to an organic mobile phase of 100% methanol. Another method is specific for 2-hydroxyglutarate, running a fast linear gradient from 50%-95% B (buffers as defined above) over 5 minutes. A Synergi Hydro-RP, 100 mm×2 mm, 2.1 μm particle size (Phenomonex) can be used as the column, as described above. Metabolites can be quantified by comparison of peak areas with pure metabolite standards at known concentration. Metabolite flux studies from $^{13}$C-glutamine can be performed as described, e.g., in Munger et al. *Nat Biotechnol* 26, 1179-86, 2008.

In an embodiment 2HG, e.g., R-2HG, is evaluated and the analyte on which the determination is based is 2HG, e.g., R-2HG. In an embodiment the analyte on which the determination is based is a derivative of 2HG, e.g., R-2HG, formed in process of performing the analytic method. By way of example such a derivative can be a derivative formed in MS analysis. Derivatives can include a salt adduct, e.g., a Na adduct, a hydration variant, or a hydration variant which is also a salt adduct, e.g., an Na adduct, e.g., as formed in MS analysis. In an embodiment an alpha hydroxy neoactivity product, e.g., 2HG, e.g., R-2HG, can be assayed indirectly. In an indirect assay the analyte is a metabolic derivative of an alpha hydroxy neoactivity product, e.g., 2HG, e.g., R-2HG, or another compound(s), e.g., a cellular compound, that is correlated to the level of an alpha hydroxy neoactivity product, e.g., 2HG, e.g., R-2HG. Examples include species that build up or are elevated, or reduced, as a result of the presence of 2HG, e.g., R-2HG. E.g., in embodiments, cancer cells with the neoactive mutant have elevated levels of glutarate or glutamate that will be correlated to 2HG, e.g., R-2HG.

Exemplary 2HG derivatives include dehydrated derivatives such as the compounds provided below or a salt adduct thereof:

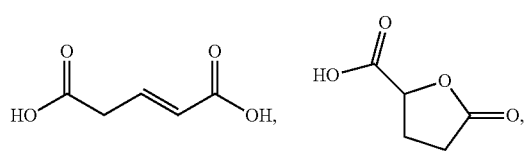

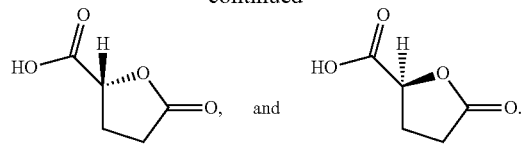

Methods of Evaluating Samples and/or Subjects

This section provides methods of obtaining and analyzing samples and of analyzing subjects.

Embodiments of the method comprise evaluation of one or more parameters related to IDH1-97$^{neo}$, e.g., IDH1-G97D, or IDH2-137$^{neo}$, neoactivity, e.g., 2HG neoactivity, e.g., to evaluate the IDH1-97$^{neo}$, e.g., IDH1-G97D, or IDH2-137$^{neo}$, genotype or phenotype. The evaluation can be performed, e.g., to select, diagnose or prognose the subject, to select a therapeutic agent, e.g., an inhibitor, or to evaluate response to the treatment or progression of disease. In an embodiment the evaluation, which can be performed before and/or after treatment has begun, is based, at least in part, on analysis of a tumor sample, cancer cell sample, or precancerous cell sample, from the subject. E.g., a sample from the patient can be analyzed for the presence or level of an alpha hydroxy neoactivity product, e.g., 2HG, e.g., R-2HG, by evaluating a parameter correlated to the presence or level of an alpha hydroxy neoactivity product, e.g., 2HG, e.g., R-2HG. An alpha hydroxy neoactivity product, e.g., 2HG, e.g., R-2HG, in the sample can be determined by a chromatographic method, e.g., by LC-MS analysis. It can also be determined by contact with a specific binding agent, e.g., an antibody, which binds the alpha hydroxy neoactivity product, e.g., 2HG, e.g., R-2HG, and allows detection. In an embodiment the sample is analyzed for the level of neoactivity, e.g., an alpha hydroxy neoactivity, e.g., 2HG neoactivity. In an embodiment the sample is analysed for the presence of an IDH1-97$^{neo}$, e.g., IDH1-G97D, or IDH2-137$^{neo}$, mutant protein having, e.g., 2HG neoactivity (or a corresponding RNA). In an embodiment a nucleic acid from the sample is sequenced (e.g., direct interrogation or by SNP analysis) to determine if an IDH1-97$^{neo}$ mutation, e.g., IDH1-G97D, or IDH2-137$^{neo}$ mutation, is present. In an embodiment the analysis is other than directly determining the presence of an IDH1-97$^{neo}$ mutation, e.g., IDH1-G97D, or IDH2-137$^{neo}$ mutation, (or corresponding RNA) or sequencing of an IDH1-97$^{neo}$ mutant, e.g., a IDH1-G97D, or IDH2-137$^{neo}$, mutant, gene. In an embodiment the analysis is other than directly determining, e.g., it is other than sequencing genomic DNA or cDNA, the presence of a mutation at residue an IDH1-97$^{neo}$ mutation, e.g., IDH1-G97D, or IDH2-137$^{neo}$ mutation. In another embodiment the analysis is comprises directly determining, e.g., by sequencing, e.g., sequencing genomic DNA or cDNA, the presence of a mutation at residue an IDH1-97$^{neo}$ mutation, e.g., IDH1-G97D, or IDH2-137$^{neo}$ mutation. E.g., the analysis can be the detection of an alpha hydroxy neoactivity product, e.g., 2HG, e.g., R-2HG, or the measurement of the mutation's an alpha hydroxy neoactivity, e.g., 2HG neoactivity. In an embodiment the sample is removed from the patient and analyzed. In an embodiment the evaluation can include one or more of performing the analysis of the sample, requesting analysis of the sample, requesting results from analysis of the sample, or receiving the results from analysis of the sample. Generally herein, determination (or determining), analysis (or analyzing), or evaluation (or evaluating) can include one or both of performing the underlying method or receiving data from another who has performed the underlying method.

In an embodiment the evaluation, which can be performed before and/or after treatment has begun, is based, at least in part, on analysis of a tissue (e.g., a tissue other than a tumor sample), or bodily fluid, or bodily product. Exemplary tissues include lymph node, skin, hair follicles and nails. Exemplary bodily fluids include blood, plasma, urine, lymph, tears, sweat, saliva, semen, and cerebrospinal fluid. Exemplary bodily products include exhaled breath. E.g., the tissue, fluid or product can be analyzed for the presence or level of an alpha hydroxy neoactivity product, e.g., 2HG, e.g., R-2HG, by evaluating a parameter correlated to the presence or level of an alpha hydroxy neoactivity product, e.g., 2HG, e.g., R-2HG. An alpha hydroxy neoactivity product, e.g., 2HG, e.g., R-2HG, in the sample can be determined by a chromatographic method, e.g., by LC-MS analysis. It can also be determined by contact with a specific binding agent, e.g., an antibody, which binds the alpha hydroxy neoactivity product, e.g., 2HG, e.g., R-2HG, and allows detection. In embodiments where sufficient levels are present, the tissue, fluid or product can be analyzed for the level of neoactivity, e.g., an alpha hydroxy neoactivity, e.g., the 2HG neoactivity. In an embodiment the sample is analysed for the presence of an IDH1-97$^{neo}$, e.g., IDH1-G97D, or IDH2-137$^{neo}$, mutant protein having, e.g., 2HG neoactivity (or a corresponding RNA). In an embodiment a nucleic acid from the sample is sequenced to determine if an IDH1-97$^{neo}$ mutation, e.g., IDH1-G97D, or IDH2-137$^{neo}$ mutation, is present. In an embodiment the analysis is other than directly determining the presence of an IDH1-97$^{neo}$ mutation, e.g., IDH1-G97D, or IDH2-137$^{neo}$, protein (or corresponding RNA) or sequencing of an IDH1-97$^{neo}$ mutation, e.g., IDH1-G97D, or IDH2-137$^{neo}$ mutation. E.g., the analysis can be the detection of an alpha hydroxy neoactivity product, e.g., 2HG, e.g., R-2HG, or the measurement of 2HG neoactivity. In an embodiment the tissue, fluid or product is removed from the patient and analyzed. In an embodiment the evaluation can include one or more of performing the analysis of the tissue, fluid or product, requesting analysis of the tissue, fluid or product, requesting results from analysis of the tissue, fluid or product, or receiving the results from analysis of the tissue, fluid or product.

In an embodiment the evaluation, which can be performed before and/or after treatment has begun, is based, at least in part, on alpha hydroxy neoactivity product, e.g., 2HG, e.g., R-2HG, imaging of the subject. In embodiments magnetic resonance methods are is used to evaluate the presence, distribution, or level of an alpha hydroxy neoactivity product, e.g., 2HG, e.g., R-2HG, in the subject. In an embodiment the subject is subjected to imaging and/or spectroscopic analysis, e.g., magnetic resonance-based analysis, e.g., MRI and/or MRS e.g., analysis, and optionally an image corresponding to the presence, distribution, or level of an alpha hydroxy neoactivity product, e.g., 2HG, e.g., R-2HG, or of the tumor, is formed. Optionally the image or a value related to the image is stored in a tangible medium and/or transmitted to a second site. In an embodiment the evaluation can include one or more of performing imaging analysis, requesting imaging analysis, requesting results from imaging analysis, or receiving the results from imaging analysis.

Methods of Treating a Proliferative Disorder

Described herein are methods of treating a cell proliferation-related disorder characterized by an IDH1-97$^{neo}$ mutation, e.g., IDH1-G97D, or IDH2-137$^{neo}$ mutation, e.g., a cancer, e.g., a glioma, e.g., by inhibiting a neoactivity of the mutant enzyme. In some embodiments, the gain of function is the conversion of α-ketoglutarate to 2-hydroxyglutarate, e.g., R-2-hydroxyglutarate.

Compounds for the Treatment of Cancer

Compounds disclosed herein for the treatment of a cell proliferation-related disorder, e.g., cancer, include: modulators, e.g., inhibitors, of a neoactive enzyme; compounds, or prodrugs thereof, that are structural analogs of a neoactivity product; anti-glycolytic agents; anti-oxidants; and nucleic acid-based therapeutic agents.

Modulators of a Neoactivity

A candidate compound can be evaluated for modulation (e g., inhibition) of neoactivity of an IDH1-97$^{neo}$ mutant, e.g., IDH1-G97D, or IDH2-137$^{neo}$ mutant, for example, using an assay described herein. A candidate compound can also be evaluated for modulation (e.g., inhibition) of wild type or non-mutant activity. For example, the formation of a product or by-product of any activity (e.g., enzymatic activity) can be assayed, thus evaluating a candidate compound. In some embodiments, the activity (e.g., wild type/non-mutant or neoactivity) can be evaluated by measuring one or more readouts from an enzymatic assay. For example, the change in nature and/or amount of substrate and/or product can be measured, e.g., using methods such as fluorescent or radiolabeled substrates. Exemplary substrates and/or products include α-ketoglutarate, $CO_2$, NADP, NADPH, NAD, NADH, and 2-hydroxyglutarate, e.g., R-2-hydroxyglutarate. In some embodiments, the rate of reaction of the enzyme can also be evaluated as can the nature and/or amount of a product of the enzymatic reaction. In addition to the measurement of potential enzymatic activities, activity (e.g., wild type/non-mutant or neoactivity) can be detected by the quenching of protein fluorescence upon binding of a potential substrate, cofactor, or enzymatic activity modulator to the enzyme.

In one embodiment, assay progress can be monitored by changes in the OD340 or fluorescence of the NAD or NADP cofactor. In another embodiment, the reaction progress can be coupled to a secondary enzyme assay system in continuous mode or endpoint mode for increasing the dynamic range of the assay. For example, an endpoint assay can be performed by adding to the reaction an excess of diaphorase and rezasarin. Diaphorase consumes the remaining NADPH or NADH while producing resorufin from rezasarin. Resorufin is a highly fluorescent product which can be measured by fluorescence at Ex544 Em590. This not only terminates the reaction but also generates an easily detectable signal with greater quantum yield than the fluorescence of the cofactor.

A continuous assay can be implemented through coupling a product of the primary reaction to a secondary enzyme reaction that yields detectable results of greater dynamic range or more convenient detection mode. For example, inclusion in the reaction mix of aldehyde dehydrogenase (ALDH), which is an NADP+ dependent enzyme, and 6-methoxy-2-napthaldehye, a chromogenic substrate for ALDH, will result in the production of the fluorescent product 6-methoxy-2-napthoate (Ex310 Em 360) at a rate dependent on the production of NADP+ by isocitrate dehydrogenase. The inclusion of a coupling enzyme such as aldehyde dehydrogenase has the additional benefit of allowing screening of neoactivity irrespective of whether NADP+ or NAD+ is produced, since this enzyme is capable of utilizing both. Additionally, since the NADPH or NADH cofactor required for the "reverse" assay is regenerated, a coupled enzyme system which cycles the cofactor back to the IDH enzyme has the further advantage of permitting continuous assays to be conducted at cofactor concentrations much below Km for the purpose of enhancing the detection of competitive inhibitors of cofactor binding.

In yet a third embodiment of an activity (e.g., wild type/non-mutant or neoactivity) screen, one or a number of IDH1 substrates, cofactors, or products can be isotopically labeled with radioactive or "heavy" elements at defined atoms for the purpose of following specific substrates or atoms of substrates through the chemical reaction. For example, the alpha carbon of a-KG, isocitrate, or 2-hydroxyglutarate, e.g., R-2-hydroxyglutarate may be $^{14}C$ or $^{13}C$. Amount, rate, identity and structure of products formed can be analyzed by means known to those of skill in the art, for example mass spectroscopy or radiometric HPLC.

Compounds that inhibit a neoactivity, e.g., a neoactivity described herein, can include, e.g., small molecule, nucleic acid, protein and antibody.

Exemplary small molecules include, e.g, small molecules that bind to enzymes and decrease their activity, e.g., a neoactivity described herein. The binding of an inhibitor can stop a substrate from entering the enzyme's active site and/or hinder the enzyme from catalyzing its reaction. Inhibitor binding is either reversible or irreversible. Irreversible inhibitors usually react with the enzyme and change it chemically. These inhibitors can modify key amino acid residues needed for enzymatic activity. In contrast, reversible inhibitors bind non-covalently and different types of inhibition are produced depending on whether these inhibitors bind the enzyme, the enzyme-substrate complex, or both. In some embodiments, the small molecule is oxalomalate, oxalofumarate, or oxalosuccinate.

In some embodiments, the small molecule is a selected inhibitor for the neoactivity (e.g., relative to the wild type activity). Exemplary small molecule compounds that inhibit the neoactivity include those of formula (XX) below:

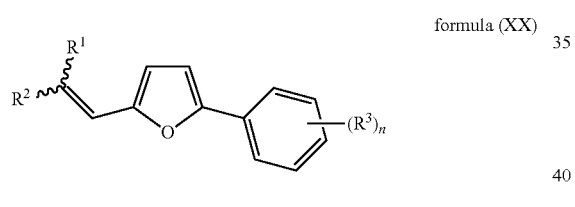

formula (XX)

wherein
$R^1$ is H, $C_1$-$C_6$ alkyl, or cyano;
$R^2$ is aryl, heteroaryl, or heterocycyl; optionally substituted with 1-3 $R^4$;
or $R^1$ and $R^2$, taken together with the carbon to which they are attached form a heteroaryl or heterocycyl;
each $R^3$ is independently $C_1$-$C_6$ alkyl, heterocyclyl, hydroxy, alkoxy, nitro, cyano, amino, amido, halo, or haloalkyl
each $R^4$ is independently $C_1$-$C_6$ alkyl, hydroxy, alkoxy, nitro, cyano, amino, amido, halo, or haloalkyl optionally substituted with 1-3 $R^4$;
n is 2.

In some embodiments, $R^1$ is cyano.
In some embodiments, $R^1$ and $R^2$, taken together with the carbon to which they are attached form a heteroaryl or heterocycyl. In some embodiments, $R^1$ and $R^2$, taken together with the carbon to which they are attached form a monocyclic heteroaryl or heterocyclyl. In some embodiments, $R^1$ and $R^2$, taken together with the carbon to which they are attached form a bicyclic heteroaryl or heterocyclyl. In some embodiments, the heteroaryl or heterocyclyl is substituted with at least 1 $R^4$ (e.g., $C_1$-$C_6$ alkyl).

In some embodiments, at least one $R^3$ is nitro. In some embodiments, at least one $R^3$ is a meta nitro. In some embodiments, the second $R^3$ is halo, hydroxy, or heterocyclyl.

Exemplary inhibitors of neoactivity are provided below:

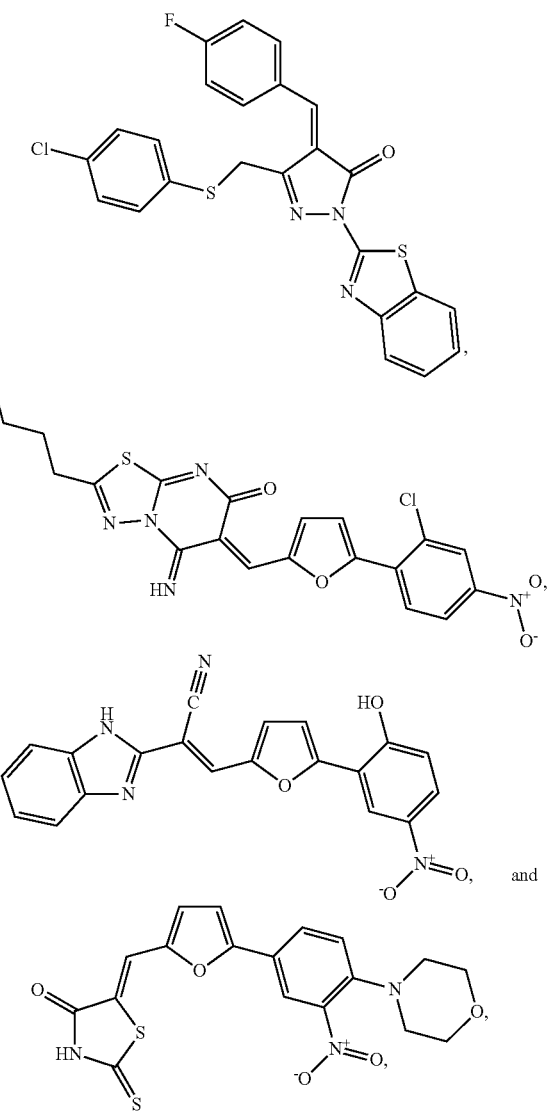

Nucleic acids can be used to inhibit a neoactivity, e.g., a neoactivity described herein, e.g., by decreasing the expression of the enzyme. Exemplary nucleic acids include, e.g., siRNA, shRNA, antisense RNA, aptamer and ribozyme. Art-known methods can be used to select inhibitory molecules, e.g., siRNA molecules, for a particular gene sequence.

Proteins can also be used to inhibit a neoactivity, e.g., a neoactivity described herein, by directly or indirectly binding to the enzyme and/or substrate, or competing binding to the enzyme and/or substrate. Exemplary proteins include, e.g., soluble receptors, peptides and antibodies. Exemplary antibodies include, e.g., whole antibody or a fragment thereof that retains its ability to bind to the enzyme or substrate.

Exemplary candidate compounds, which can be tested for inhibiting a neoactivity of an IDH1-97$^{neo}$ mutation, e.g., IDH1-G97D, or an IDH2-137$^{neo}$ mutation, are described in the following references, each of which are incorporated herein by reference: Bioorganic & Medicinal Chemistry (2008), 16(7), 3580-3586; Free Radical Biology & Medicine (2007), 42(1), 44-51; KR 2005036293 A; Applied and Environmental Microbiology (2005), 71(9), 5465-5475; KR 2002095553 A; U.S. Pat. Appl. US 2004067234 A1; PCT Int. Appl. (2002), WO 2002033063 A1; Journal of Organic Chemistry (1996), 61(14), 4527-4531; Biochimica et Biophysica Acta, Enzymology (1976), 452(2), 302-9; Journal of Biological Chemistry (1975), 250(16), 6351-4; Bollettino—Societa Italiana di Biologia Sperimentale (1972), 48(23), 1031-5; Journal of Biological Chemistry (1969), 244(20), 5709-12.

Cellular Structural Analogs of Neoactivity Products, and Prodrugs Thereof.

An exemplary cellular structural analog of a neoactivity product is alpha-ketoglutarate. Thus, the invention includes a method of treating a subject, e.g., a subject having a disorder characterized by unwanted cell proliferation, e.g., cancer, by administering a therapeutically effective amount of α-ketoglutarate (e.g., high levels as compared to normal metabolic conditions), an α-ketoglutarate prodrug, or a compound that increases the level of α-ketoglutarate to the subject.

Exemplary structural analogs include those of the formula below:

In an embodiment the cellular structural analog of a neoactive product, or prodrug thereof, is a compound of the formula below:

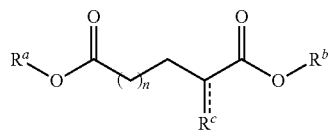

wherein

R1 and R2 are as described below;

═ is a single or double bond; and $R^4$ is O, when ═ is a double bond, or is selected from —OH, —O-(hydrophoblic moiety), —NH and —N-(hydrophobic moiety) when ═ is a single bond.

The cancer can be one described herein. A structural representation of alpha-ketoglutarate and exemplary related alpha-ketoglutarate prodrugs is provided in formula (I) below.

In some embodiments certain compounds (referred to herein as "α-ketoglutarate compounds" or "α-ketogluartates" or "α-ketogluartate esters"), can be administered to a subject to treat a cancer described herein. (These compounds may be described as α-ketoglutarates bearing (e.g., conjugated to, coupled to) a hydrophobic moiety. Exemplary compounds are described, for example, in WO2006016143, the contents of which are incorporated by reference in its entirety.

For example, these compounds may be described as α-ketoglutarate esters (i.e., esters of α-ketogluartic acid) having a hydrophobic moiety that is, or is part of, an ester group (i.e., —C(═O)OR) formed from one of the acid groups of α-ketogluartic acid.

For reference, the related parent compounds, glutaric acid and α-ketoglutaric acid are shown below.

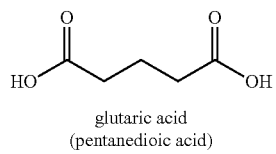

glutaric acid
(pentanedioic acid)

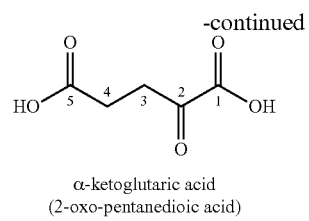

α-ketoglutaric acid
(2-oxo-pentanedioic acid)

Other structural analogues of alpha ketoglutarate can also be used for the treatment of a proliferative disorder described herein such as cancer. Additional exemplary structural analogues and prodrugs thereof are provided in the compounds of formulae (II), (III), (IV), and (V) below.

Thus, in one embodiment, alpha ketoglutarate, a structural analog, or prodrug thereof is a compound of one of the following formula (I), (II), (III), (IV), or (V):

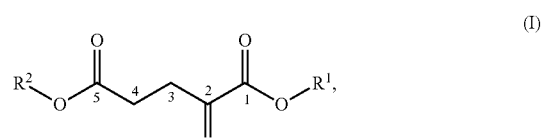

(I)

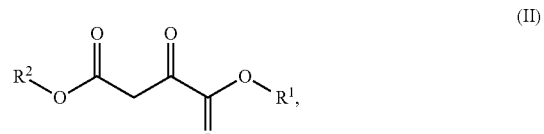

(II)

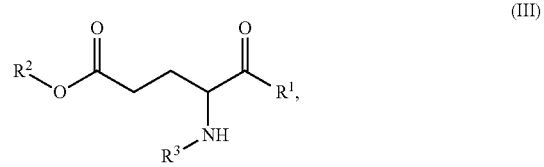

(III)

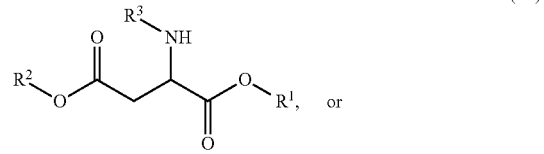

(IV)

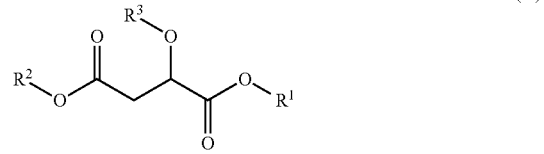

(V)

wherein each of R1 and R2 is independently selected from: (i) H; and (ii) a hydrophobic moiety; and R3 is H or a hydrophobic moiety, and pharmaceutically acceptable salts thereof.

In one embodiment, where the compound includes each of R1, R2, and R3, at least one of R1, R2, and R3 is not H.

In one embodiment, R1 and R2 are not both H

In one embodiment, neither R1 nor R2 is H (i.e., diesters).

In one embodiment, neither R1 nor R2 is H; and R1 and R2 are different. In one embodiment, neither R1 nor R2 is H; and R1 and R2 are identical.

In one embodiment, exactly one of R1 and R2 is H (i.e., monoesters).

In one embodiment, the compound is a compound of formula (I) and R1 is H (and R2 is not H):

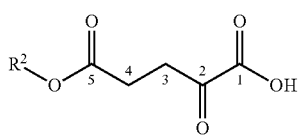

In one embodiment, the compound is a compound of formula (I) and R2 is H (and R1 is not H):

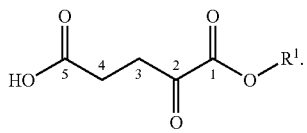

In one embodiment, the compound is a compound of formula (II) and R1 is H (and R2 is not H):

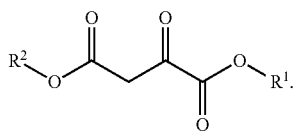

In one embodiment, the compound is a compound of formula (II) and R2 is H (and R1 is not H):

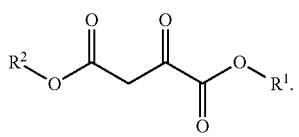

In one embodiment, the compound is a compound of formula (III) and R1 is H (and R2 is not H):

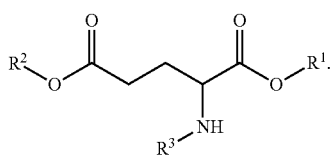

In one embodiment, the compound is a compound of formula (III) and R2 is H (and R1 is not H):

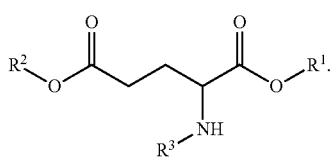

In one embodiment, the compound is a compound of formula (IV) and R1 is H (and R2 is not H):

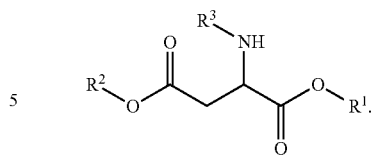

In one embodiment, the compound is a compound of formula (IV) and R2 is H (and R1 is not H):

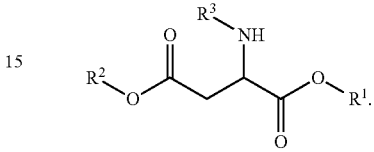

In one embodiment, the compound is a compound of formula (V) and R1 is H (and R2 is not H):

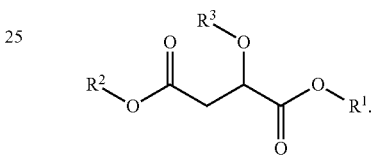

In one embodiment, the compound is a compound of formula (V) and R2 is H (and R1 is not H):

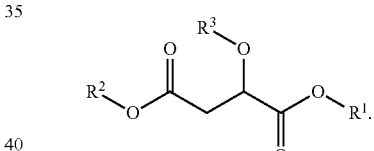

The Hydrophobic Moiety/Moieties

As used herein, the term "hydrophobic moiety" includes, but is not limited to, chemical moieties with non-polar atoms or groups that have a tendency to interact with each other rather than with water or other polar atoms or groups. Hydrophobic moieties are substantially insoluble or only poorly soluble in water. Optionally, the hydrophobic moiety may be selected according to their fusogenic properties or their interactions with components of cellular membranes, such as lectins and lipid head groups. For example, the hydrophobic moiety may comprise a polymer (e.g., a linear or branched polymer); an alkyl, alkenyl, and/or alkynyl group, which may be, for example, linear, branched or cyclic (e.g., C1-C30 alkyl, C2-C30 alkenyl, C2-C30 alkynyl, C3-C30 cycloalkyl, C3-C30 cycloalkenyl, C3-C30 cycloalkynyl); an aromatic group (e.g., C6-C20 carboaryl, Cs—C20 heteroaryl); or a combination thereof.

Optionally, the hydrophobic moiety may comprise one or more of: a heteroatom, a heterocyclic group, a peptide, a peptoid, a natural product, a synthetic compound, a steroid, and a steroid derivative (e.g., hydrophobic moieties which comprise a steroidal nucleus, e.g., a cholesterol ring system).

It is intended that the hydrophobic moiety be selected so that the α-ketoglutarate compound is capable of performing its intended function, e.g., to cross through lipid membranes into the cytosol/mitochondria.

Examples of hydrophobic moieties include, but are not limited to, those derived from: lipids, fatty acids, phospholipids, sphingolipids, acylglycerols, waxes, sterols, steroids (e.g., cholesterol), terpenes, prostaglandins, thromboxanes, leukotrienes, isoprenoids, retenoids, biotin, and hydrophobic amino acids (e.g., tryptophan, phenylalanine, isoleucine, leucine, valine, methionine, alanine, proline, and tyrosine).

In one embodiment, the hydrophobic moiety, or each hydrophobic moiety, is independently selected from: C1-C30 alkyl; C2-C30 alkenyl; C2-C30 alkynyl; C3-C30 cycloalkyl; C3-C30 cycloalkenyl; C3-C30 cycloalkynyl; C6-C20 carboaryl; C5-C20 heteroaryl; C6-C20 carboaryl-CrC7 alkyl; C5-C20 heteroaryl-d-Cr alkyl; and is unsubstituted or substituted. In one embodiment, the hydrophobic moiety, or each hydrophobic moiety, is independently selected from: C1-C30 alkyl; C2-C30 alkenyl; C2-C30 alkynyl; and is unsubstituted or substituted.

In one embodiment, the bottom of the range (for alkyl, alkenyl, alkynyl) is C4. In one embodiment, the bottom of the range is C6. In one embodiment, the bottom of the range is C8. In one embodiment, the bottom of the range is C10. In one embodiment, the bottom of the range is C12.

In one embodiment, the top of the range (for alkyl, alkenyl, alkynyl) is C30. In one embodiment, the top of the range is C24. In one embodiment, the top of the range is C22. In one embodiment, the top of the range is C20. In one embodiment, the top of the range is C18. In one embodiment, the top of the range is C16.

In one embodiment, the range (for alkyl, alkenyl, alkynyl) is C4-C20. In one embodiment, the range is C6-C18. In one embodiment, the range is C8-C16. In one embodiment, the range is C10-C24. In one embodiment, the range is C12-C22. In one embodiment, the range is C14-C20. In one embodiment, the range is C16-C18.

In one embodiment, the hydrophobic moiety, or each hydrophobic moiety, is independently C1-C30 alkyl and is unsubstituted or substituted.

In one embodiment, the bottom of the range (for alkyl) is C4. In one embodiment, the bottom of the range is C6. In one embodiment, the bottom of the range is C8. In one embodiment, the bottom of the range is C10. In one embodiment, the bottom of the range is C12.

In one embodiment, the top of the range (for alkyl) is C30. In one embodiment, the top of the range is C24. In one embodiment, the top of the range is C22. In one embodiment, the top of the range is C20. In one embodiment, the top of the range is C18. In one embodiment, the top of the range is C16.

In one embodiment, the range (for alkyl) is C4-C20. In one embodiment, the range is C6-C18. In one embodiment, the range is C8-C16. In one embodiment, the range is C10-C24. In one embodiment, the range is C12-C22. In one embodiment, the range is C14-C20. In one embodiment, the range is C16-C18.

In one embodiment, the alkyl group is a linear or branched alkyl group and is unsubstituted or substituted, for example, in one embodiment, the hydrophobic moiety is linear or branched C1-C30 alkyl and is unsubstituted or substituted.

In one embodiment, the hydrophobic moiety, or each hydrophobic moiety, is independently —(CH2)nCH3, wherein n is independently an integer from 0 to 29.

In one embodiment, the bottom of the range for n is 3. In one embodiment, the bottom of the range for n is 5. In one embodiment, the bottom of the range for n is 7. In one embodiment, the bottom of the range for n is 9. In one embodiment, the bottom of the range for n is 11.

In one embodiment, the top of the range for n is 29. In one embodiment, the top of the range for n is 23. In one embodiment, the top of the range for n is 21. In one embodiment, the top of the range for n is 19. In one embodiment, the top of the range for n is 17. In one embodiment, the top of the range for n is 15. In one embodiment, n is independently an integer from 3 to 19. In one embodiment, n is independently an integer from 5 to 17. In one embodiment, n is independently an integer from 7 to 15.

In one embodiment, the hydrophobic moiety, or each hydrophobic moiety, is independently selected from: C6-C20 carboaryl; C5-C20 heteroaryl; C6-C20 carboaryl-C1-C7 alkyl; C5-C20 heteroaryl-C1-C7 alkyl; and is unsubstituted or substituted.

In one embodiment, the hydrophobic moiety, or each hydrophobic moiety, is independently selected from: C6-C12 carboaryl; C5-C12 heteroaryl; C6-C12 carboaryl-C1-C7 alkyl; C5-C12 heteroaryl-C1-C7 alkyl; and is unsubstituted or substituted.

In one embodiment, the hydrophobic moiety, or each hydrophobic moiety, is independently selected from: C6-C10 carboaryl; C5-C10 heteroaryl; C6-C10 carboaryl-C1-C7 alkyl; C5-C10 heteroaryl-C1-C7 alkyl; and is unsubstituted or substituted.

In one embodiment, the hydrophobic moiety, or each hydrophobic moiety, is independently selected from: C6-C20 carboaryl; C6-C20 carboaryl-C1-C7 alkyl; and is unsubstituted or substituted. In one embodiment, the hydrophobic moiety, or each hydrophobic moiety, is independently selected from: C6-C12 carboaryl; C6-C12 carboaryl-C1-C7 alkyl; and is unsubstituted or substituted.

In regard to the phrase "unsubstituted or substituted", any substituents, if present, may be, in one embodiment, as defined below for Rp.

For example, in one embodiment, each carboaryl and heteroaryl group, if present, is unsubstituted or substituted with one or more (e.g., 1, 2, 3, 4, etc.) substituents independently selected from: halo; cyano; nitro; hydroxy; C1-C7 alkyoxy; C1-C7 alkyl; C1-C7 haloalkyl; and C8-C30 alkyl.

In one embodiment, the above C8-C30 alkyl groups are C10-C24 alkyl. In one embodiment, the above C8-C30 alkyl groups are C12-C22 alkyl. In one embodiment, the above C8-C30 alkyl groups are C14-C20 alkyl. In one embodiment, the above C8-C30 alkyl groups are C16-C18 alkyl.

In one embodiment, the hydrophobic moiety, or each hydrophobic moiety, is independently an optionally substituted phenyl group of formula:

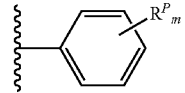

wherein m is independently 0, 1, 2, 3, 4, or 5, and each Rp, if present, is independently a substituent.

In one embodiment, the hydrophobic moiety, or each hydrophobic moiety, is independently an optionally substituted benzyl group of formula:

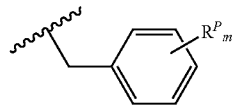

wherein m is independently 0, 1, 2, 3, 4, or 5, and each Rp, if present, is independently a substituent. In one embodiment, m is 0, 1, 2, or 3. In one embodiment, m is 0, 1, or 2. In one embodiment, m is 0 or 1.

In one embodiment, the substituents, Rp, are independently selected from the following:

(1) carboxylic acid; (2) ester; (3) amido or thioamido; (4) acyl; (5) halo; (6) cyano; (7) nitro; (8) hydroxy; (9) ether; (10) thiol; (11) thioether; (12) acyloxy; (13) carbamate; (14) amino; (15) acylamino or thioacylamino; (16) aminoacylamino or aminothioacylamino; (17) sulfonamino; (18) sulfonyl; (19) sulfonate; (20) sulfonamido; (21) C5-20aryl-C1-7alkyl; (22) C6.20-carboaryl and C5.2oheteroaryl; (23) C3-2oheterocyclyl; (24) Ci-7alkyl; C8.30alkyl; C2-7alkenyl; C2-7alkynyl; C3-7cycloalkyl; C3.7cycloalkenyl; C3-7cycloalkynyl.

In one embodiment, the substituents, Rp, are independently selected from the following:

(I) —C(O)OH; (2) —C(=O)OR1, wherein R1 is independently as defined in (21), (22), (23) or (24); (3) —C(=O)NR2R3 or —C(=S)NR2R3, wherein each of R2 and R3 is independently —H; or as defined in (21), (22), (23) or (24); or R2 and R3 taken together with the nitrogen atom to which they are attached form a ring having from 3 to 7 ring atoms; (4) —C(=O)R4, wherein R4 is independently —H, or as defined in (21), (22), (23) or (24); (5) —F, —Cl, —Br, —I; (6) —CN; (7) —NO2; (8) —OH; (9) —OR5, wherein R5 is independently as defined in (21), (22), (23) or (24); (1O) —SH; (11) —SR6, wherein R6 is independently as defined in (21), (22), (23) or (24); (12) —OC(=O)R7, wherein R7 is independently as defined in (21), (22), (23) or (24); (13) —OC(O)NR8R9, wherein each of R8 and R9 is independently —H; or as defined in (21), (22), (23) or (24); or R8 and R9 taken together with the nitrogen atom to which they are attached form a ring having from 3 to 7 ring atoms; (14) —NR10R11, wherein each of R10 and R11 is independently —H; or as defined in (21), (22), (23) or (24); or R10 and R11 taken together with the nitrogen atom to which they are attached form a ring having from 3 to 7 ring atoms; (15) —NR12C(=O)R13 or —NR12C(=S)R13, wherein R12 is independently —H; or as defined in (21), (22), (23) or (24); and R13 is independently —H, or as defined in (21), (22), (23) or (24); (16) —NR14C(=O)NR15R16 or —NR14C(=S)NR15R16, wherein R14 is independently —H; or as defined in (21), (22), (23) or (24); and each of R15 and R16 is independently —H; or as defined in (21), (22), (23) or (24); or R15 and R16 taken together with the nitrogen atom to which they are attached form a ring having from 3 to 7 ring atoms; (17) —NR17SO2R18, wherein R17 is independently —H; or as defined in (21), (22), (23) or (24); and R18 is independently —H, or as defined in (21), (22), (23) or (24); (18) —SO2R19, wherein R19 is independently as defined in (21), (22), (23) or (24); (19) —OSO2R20 and wherein R20 is independently as defined in (21), (22), (23) or (24); (20) —SO2NR21R22, wherein each of R21 and R22 is independently —H; or as defined in (21), (22), (23) or (24); or R21 and R22 taken together with the nitrogen atom to which they are attached form a ring having from 3 to 7 ring atoms; (21) C5-2oaryl-Ci-7alkyl, for example, wherein C5.20aryl is as defined in (22); unsubstituted or substituted, e.g., with one or more groups as defined in (1) to (24); (22) C6-20-carboaryl; C5-20heteroaryl; unsubstituted or substituted, e.g., with one or more groups as defined in (1) to (24); (23) C3.20heterocyclyl; unsubstituted or substituted, e.g., with one or more groups as defined in (1) to (24); (24) C1-7alkyl; C8-3oalkyl; C2-7alkenyl; C2-7alkynyl; C3-7cycloalkyl; C3-7cycloalkenyl; C3.7cycloalkynyl; unsubstituted or substituted, e.g., with one or more groups as defined in (1) to (23), e.g., halo-C1-7alkyl; e.g., amino-C1-7alkyl (e.g., —(CH2)w-amino, w is 1, 2, 3, or 4); e.g., carboxy-C1-7alkyl (e.g., —(CH2)W—COOH, w is 1, 2, 3, or 4); e.g., acyl-C1-7alkyl (e.g., —(CH2)W—C(=O)R4, w is 1, 2, 3, or 4); e.g., hydroxy-C1-7alkyl (e.g., —(CH2)W—OH, w is 1, 2, 3, or 4); e.g., C1-7alkoxy-C1.7alkyl (e.g., —(CH2)w-O—C1-7alkyl, w is 1, 2, 3, or 4).

In one embodiment, the substituents, Rp, are independently selected from the following:

(1) —C(=O)OH; (2) —C(=0)0Me, —C(=O)OEt, —C(=O)O(iPr), —C(=O)O(tBu); —C(=O)O(cPr); —C(=O)OCH2CH2OH, —C(=O)OCH2CH2OMe, —C(=O)OCH2CH2OEt; —C(=O)OPh, —C(=O)OCH2Ph; (3) —(C=O)NH2, —(C=O)NMe2, —(C=O)NEt2, —(C=O)N(IPr)2, —(C=O)N(CH2CH2OH)2; —(C=O)-morpholino, —(C=O)NHPh, —(C=O)NHCH2Ph; (4) —C(=0)H, —(C=O)Me, —(C=O)Et, —(C=0)(tBu), —(C=0)-cHex, —(C=O)Ph; —(C=O)CH2Ph; (5) —F, —Cl, —Br, —I; (6) —CN; (7) —NO2; (8) —OH; (9) —OMe, —OEt, —O(iPr), —O(tBu), —OPh, —OCH2Ph; —OCF31-OCH2CF3; —OCH2CH2OH, —OCH2CH2OMe, —OCH2CH2OEt; —OCH2CH2NH2, —OCH2CH2NMe2, —OCH2CH2N(JPr)2; —OPh-Me, —OPh-OH, —OPh-OMe, —OPh-F, —OPh-Cl, —OPh-Br, —OPh-I; (1O) —SH; (11) —SMe, —SEt, —SPh, —SCH2Ph; (12) —OC(=O)Me, —OC(=O)Et, —OC(=O)(iPr), —OC(=O)(tBu); —OC(=O)(cPr); —OC(O)CH2CH2OH, —OC(=O)CH2CH2OMe, —OC(=O)CH2CH2OEt; —OC(=O)Ph, —OC(=O)CH2Ph; (13) —OC(=O)NH2, -OC(=0)NHMe, -OC(=0)NMe2, —OC(=O)NHEt, —OC(=O)NEt2, —OC(=O)NHPh1-OC(=O)NCH2Ph; (14) —NH2, —NHMe, —NHEt, —NH(iPr), —NMe2, —NEt2, —N(JPr)2, —N(CH2CH2OH)2; —NHPh, —NHCH2Ph; piperidino, piperazino, morpholino; (15) —NH(C=O)Me, —NH(C=O)Et, —NH(C=O)nPr, —NH(C=O)Ph, —NHC(=O)CH2Ph; —NMe(C=O)Me, —NMe(C=O)Et, —NMe(C=O)Ph, —NMeC(=O)CH2Ph; (16) —NH(C=O)NH2, —NH(C=O)NHMe, —NH(C=O)NHEt, —NH(C=O)NPh, —NH(C=O)NHCH2Ph; —NH(C=S)NH2, —NH(C=S)NHMe, —NH(C=S)NHEt, —NH(C=S)NPh, —NH(C=S)NHCH2Ph; (17) —NHSO2Me, —NHSO2Et, —NHSO2Ph1-NHSO2PhMe, —NHSO2CH2Ph; —NMeSO2Me, —NMeSO2Et1-NMeSO2Ph1-NMeSO2PhMe1-NMeSO2CH2Ph; (18) —SO2Me1-SO2CF3, —SO2Et, —SO2Ph, —SO2PhMe1-SO2CH2Ph; (19) —OSO2Me1-OSO2CF3, —OSO2Et, —OSO2Ph, —OSO2PhMe, —OSO2CH2Ph; (20) —SO2NH2, —SO2NHMe, —SO2NHEt1-SO2NMe2, —SO2NEt2, —S02-morpholino, —SO2NHPh, —SO2NHCH2Ph; (21) —CH2Ph, —CH2Ph-Me, —CH2Ph-OH, —CH2Ph-F, —CH2Ph-Cl; (22)-Ph1-Ph-Me, -Ph-OH, -Ph-OMe, -Ph-NH2, -Ph-F, -Ph-Cl, -Ph-Br, -Ph-I; pyridyl, pyrazinyl, pyrimidinyl, pyridazinyl; furanyl, thiophenyl, pyrrolyl, imidazolyl, pyrazolyl, oxazolyl, thiazolyl, thiadiazolyl; (23) pyrrolidinyl, imidazolidinyl, pyrazolidinyl, piperidinyl, piperazinyl, azepinyl, tetrahydrofuranyl, tetrahydropyranyl, morpholinyl, azetidinyl; (24) -Me, -Et, -nPr, -iPr, -nBu, -iBu, -sBu, -tBu, -nPe, -nHex; —(CH2)7CH3, —(CHz)9CH3, —(CHz)11CH3, —(CH2)l3CH3, —(CH2)15CH3, —(CH2)17CH3, —(CH2J19CH3; -cPr, -cHex; —CH=CH2, —CH2-CH=CH2; —CF3, —CHF2, —CH2F, —CCI3, —CBr3, —CH2CH2F, —CH2CHF2, and —CH2CF3; —CH2OH, —CH2OMe, —CH2OEt, —CH2NH2, —CH2NMe2; —CH2CH2OH, —CH2CH2OMe, —CH2CH2OEt, —CH2CH2NH2, —CH2CH2NMe2.

In one embodiment, the substituents, Rp, are independently selected from: halo; cyano; nitro; hydroxy; C1-C7 alkyoxy; C1-C7 alkyl; C1-C7 haloalkyl; and C8-C30 alkyl.

In one embodiment, the substituents, Rp, are independently selected from: halo; cyano; nitro; hydroxy; C1-C4 alkyoxy; C1-C4 alkyl; C1-C4 haloalkyl; and C12-C22 alkyl.

In one embodiment, the substituents, Rp, are independently selected from: halo; C1-C4 alkyl; and C1-C4 haloalkyl.

In one embodiment, the substituents, Rp, are independently selected from: fluoro; C1-C4 alkyl; and C1-C4 fluoroalkyl.

In one embodiment, the substituents, Rp, are independently selected from: F, —CH3, —CF3.

As used herein, the term "halo" includes fluoro, chloro, bromo and iodo.

As used herein, the term "alkyl" pertains to monovalent, monodentate, aliphatic (linear or branched) saturated hydrocarbon moieties, for example, methyl, ethyl, n-propyl, i-propyl, etc.

Examples of (unsubstituted) alkyl groups include methyl (C1), ethyl (C2), propyl (C3), butyl (C4), pentyl (C5), hexyl (C6), heptyl (C7), octyl (C8), nonyl (C9), decyl (C10), undecyl (C11), dodecyl (C12), tridecyl (C13), tetradecyl (C14), pentadecyl (C15), and eicodecyl (C20). Examples of (unsubstituted) linear alkyl groups include methyl (C1), ethyl (C2), n-propyl (C3), n-butyl (C4), n-pentyl(amyl) (C5), n-hexyl (C6), and n-heptyl (C7).

Examples of (unsubstituted) branched alkyl groups include iso-propyl (C3), iso-butyl (C4), sec-butyl (C4), tert-butyl (C4), iso-pentyl (C5), and neo-pentyl (C5).

As used herein, the term "alkenyl" pertains to monovalent, monodentate, aliphatic (linear or branched) hydrocarbon moieties having at least one carbon-carbon double bond.

Examples of (unsubstituted) alkenyl groups include ethenyl (vinyl, —CH═CH2), 1-propenyl (—CH═CH—CH3), 2-propenyl (allyl, —CH—CH═CH2), isopropenyl (1-methylvinyl, —C(CH3)═CH2), butenyl (C4), pentenyl (C5), and hexenyl (C6).

As used herein, the term "alkynyl" pertains to monovalent, monodentate, aliphatic (linear or branched) hydrocarbon moieties having at least one carbon-carbon triple bond.

Examples of (unsubstituted) alkynyl groups include ethynyl (ethinyl, —C≡CH) and 2-propynyl (propargyl, —CH2-C≡CH).

As used herein, the term "cycloalkyl" pertains to monovalent, monodentate, non-aromatic saturated hydrocarbon moieties having at least one carbon-atom ring (preferably having from 3 to 7 ring carbon atoms).

Examples of cycloalkyl groups include those derived from saturated monocyclic hydrocarbon compounds: cyclopropane (C3), cyclobutane (C4), cyclopentane (C5), cyclohexane (C6), cycloheptane (C7), methylcyclopropane (C4), dimethylcyclopropane (C5), methylcyclobutane (C5), dimethylcyclobutane (C6), methylcyclopentane (C6), dimethylcyclopentane (C7), methylcyclohexane (C7), dimethylcyclohexane (C8), menthane (C10); and saturated polycyclic hydrocarbon compounds: thujane (C10), carane (C10), pinane (C10), bornane (C10), norcarane (C7), norpinane (C7), norbornane (C7), adamantane (C10), decalin (decahydronaphthalene) (C10).

As used herein, the term "cycloalkenyl" pertains to monovalent, monodentate, non-aromatic hydrocarbon moieties having at least one carbon-atom ring (preferably having from 3 to 7 ring carbon atoms) and at least one carbon-carbon double bond. Examples of cycloalkenyl groups include those derived from unsaturated monocyclic hydrocarbon compounds: cyclopropene (C3), cyclobutene (C4), cyclopentene (C5), cyclohexene (C6), methylcyclopropene (C4), dimethylcyclopropene (C5), methylcyclobutene (C5), dimethylcyclobutene (C6), methylcyclopentene (C6), dimethylcyclopentene (C7), methylcyclohexene (C7), dimethylcyclohexene (C8); and unsaturated polycyclic hydrocarbon compounds: camphene (C10), limonene (Ci0), pinene As used herein, the term "cycloalkynyl" pertains to monovalent, monodentate, non-aromatic hydrocarbon moieties having at least one carbon-atom ring (preferably having from 3 to 7 ring carbon atoms) and at least one carbon-carbon triple bond.

As used herein, the term "aryl" pertains to monovalent, monodentate, moieties that have an aromatic ring and which has from 3 to 20 ring atoms (unless otherwise specified). Preferably, each ring has from 5 to 7 ring atoms. The ring atoms may be all carbon atoms, as in "carboaryl" groups or the ring atoms may include one or more heteroatoms (e.g., 1, 2, 3, 4, etc.) (e.g., selected from N1 O, and S), as in "heteroaryl" groups. In this context, the prefixes (e.g., C5-C20, C5-C12, C5-C10, etc.) denote the number of ring atoms, or range of number of ring atoms, whether carbon atoms or heteroatoms.

Examples of carboaryl groups include those derived from benzene (i.e., phenyl) (C6), naphthalene (Ci0), azulene (C10), anthracene (C14), phenanthrene (C14), naphthacene (C18), and pyrene (C16).

Examples of carboaryl groups which comprise fused rings, at least one of which is an aromatic ring, include groups derived from indane (e.g., 2,3-dihydro-1H-indene) (C9), indene (C9), isoindene (C9), tetraline (1,2,3,4-tetrahydronaphthalene) (C10), acenaphthene (C12), fluorene (C13), phenalene (C13), acephenanthrene (C15), and aceanthrene (C16).

Additional examples of carboaryl groups include groups derived from: indene (C9), indane (e.g., 2,3-dihydro-1H-indene) (C9), tetraline (1,2,3,4-tetrahydronaphthalene) (C10), acenaphthene (C12), fluorene (C13), phenalene (C13), acephenanthrene (C15), aceanthrene (C16), cholanthrene (C20).

Examples of monocyclic heteroaryl groups include those derived from: N1: pyrrole (azole) (C5), pyridine (azine) (C6); Ov furan (oxole) (C5); S1: thiophene (thiole) (C5); N1O1: oxazole (C5), isoxazole (C5), isoxazine (C6); N2O1: oxadiazole (furazan) (C5); N3O1: oxatriazole (C5); N1S1: thiazole (C5), isothiazole (C5); N2: imidazole (1,3-diazole) (C5), pyrazole (1,2-diazole) (C5), pyridazine (1,2-diazine) (C6), pyrimidine (1,3-diazine) (C6) (e.g., cytosine, thymine, uracil), pyrazine (1,4-diazine) (C6); N3: triazole (C5), triazine (C6); and, N4: tetrazole (C5).

Examples of polycyclic heteroaryl groups include: Cghetherocyclic groups (with 2 fused rings) derived from benzofuran (O1), isobenzofuran (O1), indole (N1), isoindole (N1), indolizine (N1), indoline (N1), isoindoline (N1), purine (N4) (e.g., adenine, guanine), benzimidazole (N2), indazole (N2), benzoxazole (N1O1), benzisoxazole (N1-O1), benzodioxole (O2), benzofurazan (N2O1), benzotriazole (N3), benzothiofuran (S1), benzothiazole (N1S1), benzothiadiazole (N2S); doheterocyclic groups (with 2 fused rings) derived from chromene (O1), isochromene (O1), chroman (O1), isochroman (O1), benzodioxan (O2), quinoline (N1), isoquinoline (N1), quinolizine (N1), benzoxazine (N1O1), benzodiazine (N2), pyridopyridine (N2), quinoxaline (N2), quinazoline (N2), cinnoline (N2), phthalazine (N2), naphthyridine (N2), pteridine (N4); Cnheterocyclic groups (with 2 fused rings) derived from benzodiazepine (N2); C13heterocyclic groups (with 3 fused rings) derived from carbazole (N1), dibenzofuran (O1), dibenzothiophene (S1), carboline (N2), perimidine (N2), pyridoindole (N2); and, C14heterocyclic groups (with 3 fused rings) derived from acridine (N1), xanthene (O1), thioxanthene (S1), oxanthrene (O2), phenoxathiin (O1S1), phenazine (N2), phenoxazine (N1O1), phenothiazine (N1S1), thianthrene (S2), phenanthridine (N1), phenanthroline (N2), phenazine (N2).

Heteroaryl groups that have a nitrogen ring atom in the form of an —NH— group may be N-substituted, that is, as —NR—. For example, pyrrole may be N-methyl substituted, to give N-methylpyrrole. Examples of N-substitutents include C1-C7 alkyl; C6-C20 carboaryl; C6-C20 carboaryl-CrC7 alkyl; C1-C7 alkyl-acyl; C6-C20 carboaryl-acyl; C6-C20 carboaryl-CrC7 alkyl-acyl; etc. Heteroaryl groups) which have a nitrogen ring atom in the form of an —N═ group may be substituted in the form of an N-oxide, that is, as —N(→O)═ (also denoted —N+(→O")═). For example, quinoline may be substituted to give quinoline N-oxide; pyridine to give pyridine N-oxide; benzofurazan to give benzofurazan N-oxide (also known as benzofuroxan).

Molecular Weight

In one embodiment, the compound has a molecular weight of 250 to 1000. In one embodiment, the bottom of range is 275; 300; 325; 350; 375; 400; 425; 450. In one embodiment, the top of range is 900; 800; 700; 600; 500; 400. In one embodiment, the range is 250 to 900. In one embodiment, the range is 250 to 800. In one embodiment, the range is 250 to 700. In one embodiment, the range is 250 to 600. In one embodiment, the range is 250 to 500.

Some Preferred Examples

All plausible and compatible combinations of the embodiments described above are explicitly disclosed herein. Each of these combinations is disclosed herein to the same extent as if each individual combination was specifically and individually recited.

Examples of some preferred compounds include the following:

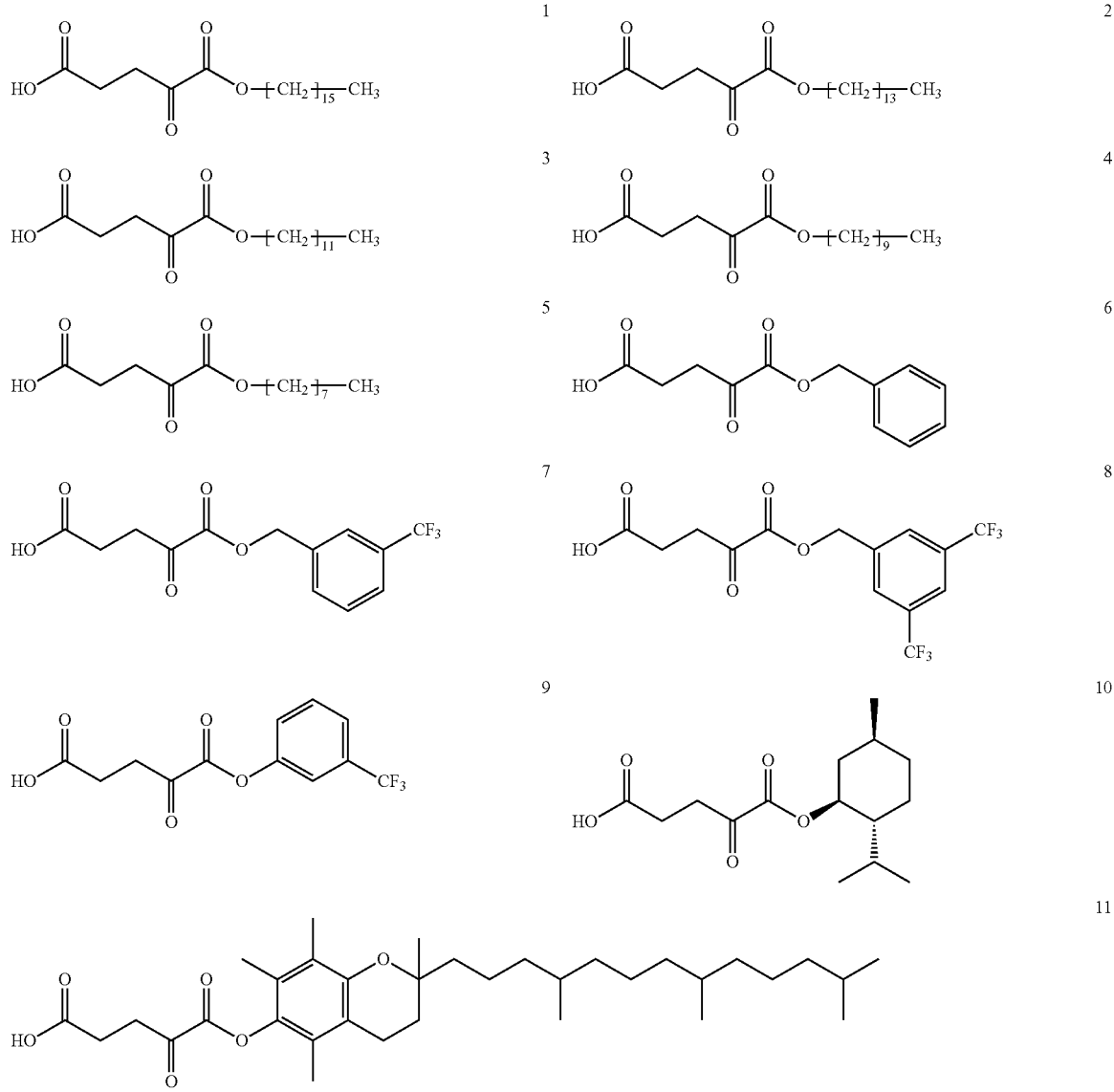

In embodiments, the compound is a compound of formula (II) wherein R1 is a moiety as shown in compounds, 1, 2, 3, 4, 5, 6, 7, 8, 9, 10, or 11 in the table above:

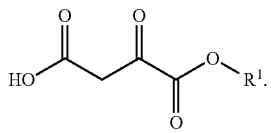

In embodiments, the compound is a compound of formula (III) wherein R1 is a moiety as shown in compounds, 1, 2, 3, 4, 5, 6, 7, 8, 9, 10, or 11 in the table above:

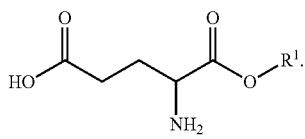

In embodiments, the compound is a compound of formula (IV) wherein R1 is a moiety as shown in compounds, 1, 2, 3, 4, 5, 6, 7, 8, 9, 10, or 11 in the table above:

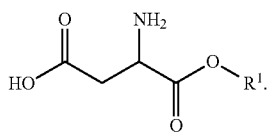

In embodiments, the compound is a compound of formula (V) wherein R1 is a moiety as shown in compounds, 1, 2, 3, 4, 5, 6, 7, 8, 9, 10, or 11 in the table above:

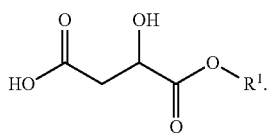

Anti-Glycolytic Compounds

In some embodiments, an anti-glycolytic compound or glycolitic inhibitor can be administered to a subject for the treatment of a proliferative disorder such as cancer such as a cancer described herein. The terms "anti-glycolytic compound" and "glycolitic inhibitor" are used herein interchangeably.

In embodiments a glycolitic inhibitor is a compound, which upon administration, turns a PET positive cancer (e.g., tumor) into a PET negative cancer.

In embodiments a glycolitic inhibitor is a compound, which upon administration of a therapeutically effective amount, inhibits an enzyme in the glycolytic pathway or inhibits glucose uptake (e.g., directly inhibits glucose uptake and/or formation).

In an embodiment a glycolitic inhibitor is a compound, which upon administration, directly competes with glucose (e.g., for access to a cellular target such as an enzyme).

As discussed above, in some embodiments, a glycolitic inhibitor is a compound, which upon administration, turns a PET positive cancer (e.g., tumor) into a PET negative cancer. In some preferred embodiments, the glycolitic inhibitor converts a cancer cell dependent on glycolysis into a cancer cell whose capability for glycolysis is so impaired such that it is essentially incapable of glycolysis. Exemplary glycolitic inhibitors that can render a cancer cell essentially incapable of glycolysis include: Alkylating Agents; Nitrosoureas; Anti-tumor Antibiotics; Corticosteroid Hormones; Anti-estrogens; Aromatase Inhibitors; Progestins; Anti-androgens; LHRH agonists; Antibody therapies; and other anti-cancer therapies. Examples of Alkylating Agents include busulfan, cisplatin, carboplatin, chlorambucil, cyclophosphamide, ifosfamide, dacarbazine $(DTIC)_5$ mechlorethamine (nitrogen mustard), and melphalan. Examples of Nitrosoureas include carmustine (BCNU) and lomustine (CCNU). Examples of Antitumor Antibiotics include dactinomycin, daunorubicin, doxorubicin (Adriamycin), idarubicin, and mitoxantrone.

Examples of Corticosteroid Hormones include prednisone and dexamethasone. Examples of anti-estrogens include tamoxifen and fulvestrant. Examples of aromatase inhibitors include anastrozole and letrozole. An example of a Progestin is megestrol acetate. Examples of anti-androgens include bicalutamide, flutamide. Examples of LHRH agonists include leuprolide and goserelin. Examples of antibody therapies include Herceptin and Avastin. Examples of other anti-cancer compounds include L-asparaginase and tretinoin. In some embodiments, combinations or two or more anticancer compounds may be used.

There are numerous methods of determining whether or not a cancer is dependent upon glycolysis. Samples of tumors can be excised and examined in vitro by any one of several well known assays to determine if the cells are dependent on glycolysis. Such methods can determine whether or not the cells utilize aerobic or anaerobic glycolysis. FDG-PETscan technology uses high levels of glucose uptake as a marker for detection. The cancer cells that take up the detectable glucose derivative $^{18}$-fluoro-2-deoxyglucose can be located on a computer image of the patient's anatomy. Those cancers which can be detected by FDG-PETscan technology have a high likelihood of being dependent on glycolysis.

PET methodologies are set forth in Czernin, J. 2002 Acta Medica Austriaca 29:162-170, which is incorporated herein by reference. Many cancers are characterized by a high rate of glycolysis wherein the cancer has cells which exhibit a higher rate of glycolysis than that of the tissue surrounding it. Such cancer cells take up above-average quantities of glucose from the environment. Cancer characterized by a high rate of glycolysis can be identified using PET imaging technology, preferably with $^{18}$-fluoro-deoxyglucose. The positive detection of a tumor using such a test indicates that the cancer is characterized by glycolysis.

As discussed elsewhere herein, in some embodiments, a glycolitic inhibitor is a compound, which upon administration, inhibits an enzyme in the glycolytic pathway or inhibits glucose uptake (e.g., directly inhibits glucose uptake and/or formation). In some preferred embodiments, the compound selectively inhibits an isoform of an enzyme in the glycolytic pathway that is present in cancer cells, for example, a cancer-specific isoform of a kinase or dehydrogenase such as PKM2 or LDHa. Other exemplary enzymes in the glycolytic pathway that can be targeted by a glycolytic inhibitor include glut1, hexokinase2, phosphofructokinase 3, and pyruvate dehydrogenase kinase 1 (PDK1). Accordingly, included herein are compounds that inhibit an enzyme in the glycolitic pathway such as an enzyme described below.

Glucose Transporter Type 1 (GLUT1)

Glucose transporter type 1 (GLUT1), also known as solute carrier family 2, facilitated glucose transporter member 1, or HepG2 glucose transporter, is an enzyme of the sugar transporter family and glucose transporter subfamily. Glucose transporters (GLUTs) facilitate the energy independent transport of glucose across the hydrophobic cell membrane down its concentration gradient, and each of the GLUTs possesses different affinities for glucose and other sugars. GLUT1 has a broad substrate specificity and can transport a range of aldoses including both pentoses and hexoses. Particularly, it has a high affinity for glucose and may be responsible for constitutive or basal glucose uptake required to sustain respiration in cells.

GLUT1 is primary located on the cell membrane and expressed at variable levels in many human tissues. It has 12 transmembrane α-helical domains, each containing 21 amino acid residues. The precursor of human GLUT1 protein have 492 amino acids and a molecular weight of about 54 kDa, and is encoded by SLC2A1 (also known as GLUT1) gene Amino acid and nucleotide sequences of human and mouse GLUT1 are described e.g., in Mueckler et al., Science 229:941-945 (1985), and Kaestner et al., Proc. Natl. Acad. Sci. U.S.A. 86:3150-3154 (1989), respectively.

Increased and deregulated expression of GLUT1 is associated with increased glucose transport in a variety of cancer cells (Macheda et al., J Cell Physiol. 202:654-62 (2005)). Oncogenic transformation of cultured mammalian cells can cause an increase of GLUT1 expression via interaction with GLUT1 promoter enhancer elements. GLUT1 is overexpressed in cultured breast cancer cell lines and the levels of GLUT1 correspond to their invasive potentials. GLUT1 levels and glucose uptake can also be increased by hypoxia in ovarian and lung cancer cells. In the clinical setting, elevated GLUT1 expression are observed in a number of cancers including e.g., hepatic, pancreatic, breast, esophageal, brain, renal, lung, cutaneous, colorectal, endometrial, ovarian, and cervical carcinoma. High levels of GLUT1 expression in tumors are also associated with poor survival.

GLUT1 inhibitors are known in the art. Exemplary GLUT1 inhibitors are described e.g., in Macheda et al., J. Cell Physiol. 202:654-62 (2005), Singh et al., Mol Cell Endocrinol. 160:61-66 (2000), and Zhang et al. Bioconjug. Chem. 14:709-714 (2003), each of which is incorporated herein by reference in its entirety.

Hexokinase 2 (HK2)

Hexokinase 2 (HK2), also known as Hexokinase type II or muscle form hexokinase, is an enzyme of hexokinase family. Hexokinases are enzymes that phosphorylate hexose to hexose phosphate. In vertebrates there are four major glucose-phosphorylating isozymes, designated hexokinase 1-4. Hexokinase 2 catalyzes the reaction of ATP+D-hexose=ADP+D-hexose 6-phosphate. It is a low $K_m$ isozyme that has a high affinity for glucose at low concentrations (e.g., below 1 mM) and follows Michaelis-Menton kinetics at physiological concentrations of substrates. Hexokinase 2 is an allosteric enzyme inhibited by its product glucose-6-phosphate.

Hexokinase 2 is primary located at the outer mitochondrial membrane and predominantly expressed in insulin-responsive tissues such as skeletal muscle. Human hexokinase 2 has 917 amino acids and a molecular weight of about 102 kDa, and is encoded by HK2 gene Amino acid and nucleotide sequences of human and mouse hexokinase 2 are described e.g., in Deeb et al., Biochem. Biophys. Res. Commun. 197: 68-74 (1993), and Heikkinen et al., Mamm. Genome 11:91-96 (2000), respectively.

Increased expression of hexokinase 2 is associated with a number of cancers e.g., lung, liver, gastrointestinal, and breast cancer. Hexokinase 2 is also overexpressed in brain metastasis in breast cancer patients. In cancer cells, the highly glycolytic phenotype is supported by the overexpression of hexokinase 2. Overexpression of hexokinase 2 leads to the production of glucose-6-phosphate at an elevated rate, thereby promotes an unfavorable environment for normal cells and support cell proliferation. Hexokinase 2 can also increase metastasis by suppression of cancer cell death (Mathupala et al., Oncogene 25:4777-4786 (2006)).

Hexokinase 2 inhibitors are known in the art. Exemplary hexokinase 2 inhibitors are described e.g., in U.S. Pat. No. 5,854,067, Mathupala et al., Oncogene 25:4777-4786 (2006), and Kim et al., Mol. Cancer. Ther. 6:2554-2562 (2007), each of which is incorporated herein by reference in its entirety.

Phosphofructokinase 3 (PFKFB3)

Phosphofructokinase 3 (PFKFB3), also known as 6-phosphofructo-2-kinase/fructose-2,6-biphosphatase 3, 6PF-2-K/Fru-2,6-P2ASE brain/placenta-type isozyme, iPFK-2, or renal carcinoma antigen NY-REN-56, is an enzyme of the 6-phosphofructo-2-kinase/fructose-2,6-biphosphatase (PFK2/FBPase) family and the phosphoglycerate mutase family. In humans there are four major PFK2/FBPases, designated PFK2/FBPases 1-4. PFK2/FBPases control the steady-state concentration of fructose-2,6-bisphosphate (Fru-2,6-BP). PFKFB3 can catalyze the following reaction:

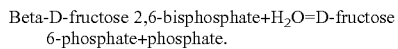

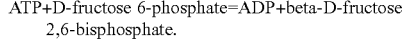

PFKFB3 has both 6-phosphofructo-2-kinase and fructose-2,6-bisphosphatase domains and is ubiquitously expressed in tissues. The precursors of human PFKFB3 isoforms 1 and 2 have 520 amino acids and a molecular weight of about 60 kDa, and 514 amino acids and a molecular weight of about 59 kDa, respectively. Human PFKFB3 is encoded by PFKFB3 gene. Amino acid and nucleotide sequences of human and mouse PFKFB3 are described e.g., in Sakai et al., J. Biochem. 119:506-511 (1996), Manzano et al., Cell Genet. 83:214-217 (1998), and the MGC Project Team, Genome Res. 14:2121-2127 (2004).

The PFKFB3 is overexpressed in a number of cancer cells including e.g., leukemia, colon, prostate, lung, breast, pancrease, thyoid, and ovarian cancer and is required for the growth of certain leukemia and cervical cancer cell lines (Clem et al., Mol Cancer Ther. 7:110-20 (2008)). By regulating the intracellular fructose-2,6-bisphosphate concentration, PFKFB3 controls glycolytic flux to lactate and the nonoxidative pentose shunt, and is required for the high glycolytic rate and anchorage-independent growth of ras-transformed cells (Chesney, Curr. Opin. Clin. Nutr. Metab. Care 9:535-539 (2006)).

PFKFB3 inhibitors are known in the art. Exemplary PFKFB3 inhibitors are described e.g., in US Patent Application Publication No. 2009/0074884 and Clem et al., Mol. Cancer. Ther. 7:110-20 (2008), each of which is incorporated herein by reference in its entirety.

Pyruvate Kinase M2 (PKM2)

Pyruvate kinase M2 (PKM2), also known as pyruvate kinase muscle isozyme, pyruvate kinase 2/3, cytosolic thyroid hormone-binding protein, THBP1, p58, M2-PK, or tumor M2-PK, is an enzyme of the pyruvate kinase family. There are four isozymes of pyruvate kinase in mammals: L, R, M1 and M2. L type is major isozyme in the liver, R is found in red cells, M1 is the main form in muscle, heart and brain, and M2 is found in early fetal tissues as well as in most cancer cells. PKM2 is a glycolytic enzyme that catalyzes the transfer of a phosphoryl group from phosphoenolpyruvate (PEP) to ADP, generating ATP. PKM2 exists as a monomer in the absence of FBP, and reversibly associates to form a homotetramer in the presence of FBP. Tetramer formation induces pyruvate kinase activity. The tetrameric form has high affinity for the substrate and is associated within the glycolytic enzyme complex. The ratio between the highly active tetrameric form and nearly inactive dimeric form determines whether glucose carbons are channeled to biosynthetic processes or used for glycolytic ATP production. PKM2 is allosterically activated by D-fructose 1,6-biphosphate (FBP) and inhibited by oxalate and 3,3',5-triiodo-L-thyronine (T3). The activity of the tetrameric form is inhibited by PML.

PKM2 stimulates POU5F1-mediated transcriptional activation and plays a role in caspase independent cell death of tumor cells. It exists in a relatively inactive dimeric form in tumor cells and the dimeric form has less affinity for the substrate. Binding to certain oncoproteins e.g., HPV-16 E7 oncoprotein can trigger dimerization. FBP stimulates the formation of tetramers from dimmers. The transition between the tetrameric and dimeric forms contributes to the control of glycolysis and is important for tumor cell proliferation and survival.

The precursor of human PKM2 has 531 amino acids and a molecular weight of about 58 kDa and is encoded by PKM2 (also known as PK2, PK3, or PKM) gene. Amino acid and nucleotide sequences of human and mouse PKM2 are described e.g., in Tani et al., Gene 73:509-516 (1988), Kato et al., Proc. Natl. Acad. Sci. U.S.A. 86:7861-7865 (1989), Izumi et al., Biochim Biophys. Acta 1267:135-138 (1995), and de Luis and del Mazo, Biochim Biophys. Acta 1396:294-305 (1998).

PKM2 inhibitors are known in the art. Exemplary PKM2 inhibitors are described e.g., in US Patent Application Publication No. 2008/0021116, International Patent Application Publication Nos. WO 2008/019139 and WO 2006/125323, Spoden et al., Int. J. Cancer 123:312-321 (2008), and Abstract #4408, AACR 100$^{th}$ annual meeting (Denver, Colo., USA, Apr. 18-22, 2009), each of which is incorporated herein by reference in its entirety.

Lactate Dehydrogenase A (LDHa)

Lactate dehydrogenase A (LDHa), also known as LDH muscle subunit, renal carcinoma antigen NY-REN-59, cell proliferation-inducing gene 19 protein, is an enzyme of the LDH family and LDH/MDH superfamily. LDHa catalyzes the conversion of L-lactate and NAD+ to pyruvate and NADH in the final step of anaerobic glycolysis.

LDHa is primary located in the cytoplasm and can form a homotetramer. Many types of cancers, e.g., testicular cancer, Ewing's sarcoma, non-Hodgkin's lymphoma, and some types of leukemia, as well as other diseases, can cause LDHa levels to be elevated. Reduction in LDHa activity can stimulate mitochondrial respiration and compromise the ability of tumor cells to proliferate under hypoxia (Fantin et al., Cancer Cell. 9:425-434 (2006)). Defects in LDHa are also a cause of exertional myoglobinuria.

The precursor of human LDHa isoform 1 has 332 amino acids and a molecular weight of about 37 kDa, and the precursor of human LDHa isoform 2 has 332 amino acids and a molecular weight of about 36 kDa. Human LDHa is encoded by LDHA gene Amino acid and nucleotide sequences of human and mouse LDHa are described e.g., in Tsujibo et al., Eur. J. Biochem. 147:9-15 (1985), Ota et al., Nat. Genet. 36:40-45 (2004) Li et al., Eur. J. Biochem. 149:215-225 (1985), and Akai et al., Int. J. Biochem. 17:645-648 (1985).

LDHa inhibitors are known in the art. Exemplary LDHa inhibitors are described e.g. in U.S. Pat. Nos. 5,853,742 and 6,124,498, and International Patent Application Publication No. WO 98/36774, each of which is incorporated herein by reference in its entirety.

Pyruvate Dehydrogenase Kinase Isoform 1 (PDK1)

Pyruvate dehydrogenase kinase isoform 1 (PDK1), is an enzyme of the pyruvate dehydrogenase kinase/branched-chain alpha-ketoacid dehydrogenase kinasePDK/BCKDK protein kinase family. Pyruvate dehydrogenase kinases inactivate pyruvate dehydrogenase by phosphorylating it using ATP. PDK has four isozymes, designated as PDK1-4. PDK1 inhibits the mitochondrial pyruvate dehydrogenase complex by phosphorylation of the E1 alpha subunit, thus contributing to the regulation of glucose metabolism. The catalytic activity of PDK1 can be illustrated as:

ATP+[pyruvate dehydrogenase (acetyl-transferring)]=
ADP+[pyruvate dehydrogenase (acetyl-transferring)]phosphate.

PDK1 is primarily located in the mitochondrion matrix and expressed predominantly in the heart. The inhibition of pyruvate dehydrogenase complex (PDC) activity by PDK1 contributes to the malignant phenotype in a number of cancers, e.g., head and neck squamous cell carcinoma, and is associated with the stabilization of HIF-1α. Inhibition of PDK1 expression can lead to the reduction of lactate levels, HIF-1α expression, and the degree of malignant phenotype in cancer cells (McFate et al., J. Biol. Chem. 283:22700-22708 (2008)).

The precursor of PDK1 has 436 amino acids and a molecular weight of about 49 kDa. Human PDK1 is encoded by PDK1 gene Amino acid and nucleotide sequences of human PDK1 are described e.g., in Gudi et al., J. Biol. Chem. 270: 28989-28994 (1995), the MGC Project Team, Genome Res. 14:2121-2127 (2004), and Carninci et al. Science 309:1559-1563 (2005).

PDK1 inhibitors are known in the art. Exemplary PDK1 inhibitors are described e.g. in U.S. Pat. No. 6,878,712, US Patent Application Publication No. 2009/0209618, International Patent Application Publication Nos: WO 2001/052825, WO 2002/081751 and WO 2005/092040, Cairns et al., Proc. Natl. Acad. Sci. U.S.A. 104:9445-9450 (2007), Mann et al., Biochim. Biophys Acta. 1480:283-292 (2000), and Aicher et al., J. Med. Chem. 42:2741-2746 (1999) each of which is incorporated herein by reference in its entirety.

Candidate compounds can be evaluated for inhibition of an enzyme described herein, e.g., a glycolytic enzyme, using methods known in the art.

As is discussed above, in some embodiments, a glycolitic inhibitor is a compound, which upon administration, directly competes with glucose. Exemplary compounds include structural derivatives of glucose such as 2 deoxyglucose (i.e., 2dg).

Antioxidants

In some embodiments, an antioxidant compound can be administered to a subject for the treatment of a cell proliferation-related disorder such as cancer such as a cancer described herein.

The term "antioxidant," as used herein, refers to a compound that slows or prevents the oxidation of a molecule, e.g., the transfer of electrons from a substance to an oxidizing agent. Oxidation reactions can produce free radicals, which can start a chain reaction that damage cells. Antioxidants can terminate these chain reactions by removing free radical intermediates, and inhibit other oxidation reactions by being oxidized themselves. Exemplary antioxidants include reducing agents such as thiols, ascorbic acids, or phenols (e.g., a polyphenol).

In general, antioxidants are classified into two broad divisions, water soluble (i.e., hydrophilic) or lipid soluble (i.e., hydrophobic). In general, water-soluble antioxidants react with oxidants in the cell cytosol and the blood plasma, while lipid-soluble antioxidants protect the cell membrane from lipid peroxidation. Exemplary water soluble antioxidants include ascorbic acid, glutathione, lipoic acid, and uric acid. Exemplary lipid soluble antioxidants include carotenes, alpha-tocopherol, and ubiquinol. Exemplary phenolic antioxidants include resveritrol and flavinoids. In some embodiments, the antioxidant is an enzymatic antioxidant such as superoxide dismutase, catalase, peroxiredoxin, thioredoxin and glutathione systems.

Candidate compounds can be evaluated for antioxidant activity using assays known in the art.

Hypomethylating Agents

It has been discovered that certain genes in patients (e.g., AML, MDS or glioma) harboring an IDH mutation (e.g., an IDH1 or IDH2 mutation) have increased methylation (e.g., hypermethylation) in the promoter region. In some embodiments, a hypomethylating agent can be administered to a subject for the treatment of a cell proliferation-related disorder such as cancer such as a cancer described herein.

The term "hypomethylating agent" as used herein, refers to a compound that inhibits DNA methylation. The term "hypomethylating agent" can be used interchangeably with the term "demethylating agent."

Exemplary hypomethylating agents include the following compounds, decitabine (5-aza-deoxycytidine), zebularine, isothiocyanates, azacitidine (5-azacytidine), 5-fluoro-2'-deoxycytidine, 5,6-dihydro-5-azacytidine, ethionine, S-adenosyl-L-homocysteine, mitoxantrone, neplanocin A, 3-deazaneplanocin A, cycloleucine, hydralazine, phenylhexyl isothiocyanate, curcumin, parthenolide, and SGI-1027.

Additional Therapeutic Compounds—Compounds that Increase the Level of α-Ketoglutarate In some embodiments, a compound (generally) that increases the level of α-ketoglutarate (e.g., in a cell) can be used in a method described herein. For example, a compound may increase α-ketoglutarate levels by inhibiting other enzymes such as α-ketoglutarate dehydrogenase and/or branched-chain keto acid dehydrogenase. Blocking these enzymes can have a dual effect of increasing α-ketoglutarate levels and decreasing succinate levels.

Moreover, both enzymes are structural homologs that use lipoic acid as a cofactor. Therefore, a lipoic acid analogue may be another potential inhibitor of these enzymes, and so be a compound that increases the level of α-ketoglutarate Alternatively, a compound might increase the level of α-ketoglutarate by enhancing glutamate oxaloacetate transaminase (GOT) activity. Glutamate itself will activate GOT activity leading to increased α-ketoglutarate levels.

Moreover, the compound may be selected from upstream metabolites of the TCA cycle including oxaloacetate, citrate, isocitrate, and derivatives thereof.

Additional Compounds—α-Ketoglutarates Generally.

Described herein are α-ketoglutaric acid, α-ketoglutarate salts, and α-ketoglutaric acid derivatives (e.g., esters of α-ketoglutaric acid, generally), and, especially, their use in medicine, for example, in the treatment of a cancer described herein.

In one embodiment, the compound is an α-ketoglutarate bearing (e.g., conjugated to, coupled to) an amino acid moiety (e.g., an α-amino acid moiety) (e.g., an ornithine or arginine moiety).

In one embodiment, the compound is an α-ketoglutarate ester (i.e., an ester of α-ketoglutaric acid) having an amino acid moiety (e.g., an α-amino acid moiety) (e.g., an ornithine or arginine moiety) that is, or is part of, an ester group (i.e., —C(=O)OR) formed from one of the acid groups of α-ketoglutaric acid.

Such compounds are known in the literature (see, e.g. Le Boucher et al. (1997)) and/or are commercially available and/or may be prepared using conventional synthetic procedures known to the skilled person.

Isomers

Certain compounds may exist in one or more particular geometric, optical, enantiomeric, diasteriomeric, epimeric, atropic, stereoisomer, tautomeric, conformational, or anomeric forms, including but not limited to, cis- and trans-forms; E- and Z-forms; c-, t-, and r-forms; endo- and exo-forms; R-, S-, and meso-forms; D- and L-forms; d- and l-forms; (+) and (−) forms; keto-, enol-, and enolate-forms; syn- and anti-forms; synclinal- and anticlinal-forms; α- and β-forms; axial and equatorial forms; boat-, chair-, twist-, envelope-, and halfchair-forms; and combinations thereof, hereinafter collectively referred to as "isomers" (or "isomeric forms").

In one embodiment, a compound described herein, e.g., an inhibitor of a neoactivity or 2-HG is an enantiomerically enriched isomer of a stereoisomer described herein. For example, the compound has an enantiomeric excess of at least about 10%, 15%, 20%, 25%, 30%, 35%, 40%, 45%, 50%, 55%, 60%, 65%, 70%, 75%, 80%, 85%, 90%, 95%, 96%, 97%, 98%, or 99%. Enantiomer, when used herein, refers to either of a pair of chemical compounds whose molecular structures have a mirror-image relationship to each other.

In one embodiment, a preparation of a compound disclosed herein is enriched for an isomer of the compound having a selected stereochemistry, e.g., R or S, corresponding to a selected stereocenter, e.g., the 2-position of 2-hydroxyglutaric acid. For example, the compound has a purity corresponding to a compound having a selected stereochemistry of a selected stereocenter of at least about 60%, 65%, 70%, 75%, 80%, 85%, 90%, 95%, 96%, 97%, 98%, or 99%.

In one embodiment, a composition described herein includes a preparation of a compound disclosed herein that is enriched for a structure or structures having a selected stereochemistry, e.g., R or S, at a selected stereocenter, e.g., the 2-position of 2-hydroxyglutaric acid. Exemplary R/S configurations can be those provided in an example described herein.

An "enriched preparation," as used herein, is enriched for a selected stereoconfiguration of one, two, three or more selected stereocenters within the subject compound. Exemplary selected stereocenters and exemplary stereoconfigurations thereof can be selected from those provided herein, e.g., in an example described herein. By enriched is meant at least 60%, e.g., of the molecules of compound in the preparation have a selected stereochemistry of a selected stereocenter. In an embodiment it is at least 65%, 70%, 75%, 80%, 85%, 90%, 95%, 96%, 97%, 98%, or 99%. Enriched refers to the level of a subject molecule(s) and does not connote a process limitation unless specified.

Note that, except as discussed below for tautomeric forms, specifically excluded from the term "isomers," as used herein, are structural (or constitutional) isomers (i.e., isomers which differ in the connections between atoms rather than merely by the position of atoms in space). For example, a reference to a methoxy group, —OCH3, is not to be construed as a reference to its structural isomer, a hydroxymethyl group, —CH2OH. Similarly, a reference to ortho-chlorophenyl is not to be construed as a reference to its structural isomer, meta-chlorophenyl. However, a reference to a class of structures may well include structurally isomeric forms falling within that class (e.g., C1-7alkyl includes n-propyl and iso-propyl; butyl includes n-, iso-, sec-, and tert-butyl; methoxyphenyl includes ortho-, meta-, and para-methoxyphenyl).

The above exclusion does not pertain to tautomeric forms, for example, keto-, enol-, and enolate-forms, as in, for example, the following tautomeric pairs: keto/enol (illustrated below), imine/enamine, amide/imino alcohol, amidine/amidine, nitroso/oxime, thioketone/enethiol, N-nitroso/hydroxyazo, and nitro/aci-nitro.

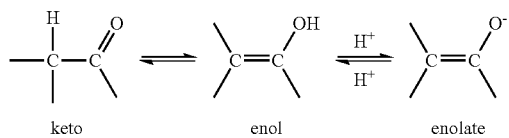

Note that specifically included in the term "isomer" are compounds with one or more isotopic substitutions. For example, H may be in any isotopic form, including 1H, 2H (D), and 3H (T); C may be in any isotopic form, including 12C, 13C, and 14C; O may be in any isotopic form, including 16O and 18O; and the like. Unless otherwise specified, a reference to a particular compound includes all such isomeric forms, including (wholly or partially) racemic and other mixtures thereof. Methods for the preparation (e.g., asymmetric synthesis) and separation (e.g., fractional crystallisation and chromatographic means) of such isomeric forms are either known in the art or are readily obtained by adapting the methods taught herein, or known methods, in a known manner.

Salts

It may be convenient or desirable to prepare, purify, and/or handle a corresponding salt of the active compound, for example, a pharmaceutically-acceptable salt. Examples of pharmaceutically acceptable salts are discussed in Berge et al., 1977, "Pharmaceutically Acceptable Salts." J. Pharm. ScL. Vol. 66, pp. 1-19.

For example, if the compound is anionic, or has a functional group which may be anionic (e.g., —COOH may be —COO"), then a salt may be formed with a suitable cation. Examples of suitable inorganic cations include, but are not limited to, alkali metal ions such as Na+ and K+, alkaline earth cations such as Ca2+ and Mg2+, and other cations such as Al+3. Examples of suitable organic cations include, but are not limited to, ammonium ion (i.e., NH4+) and substituted ammonium ions (e.g., NH3R+, NH2R2+, NHR3+, NR4+). Examples of some suitable substituted ammonium ions are those derived from: ethylamine, diethylamine, dicyclohexylamine, triethylamine, butylamine, ethylenediamine, ethanolamine, diethanolamine, piperazine, benzylamine, phenylbenzylamine, choline, meglumine, and tromethamine, as well as amino acids, such as lysine and arginine. An example of a common quaternary ammonium ion is N(CH3)4+.

If the compound is cationic, or has a functional group that may be cationic (e.g., —NH2 may • be —NH3+), then a salt may be formed with a suitable anion. Examples of suitable inorganic anions include, but are not limited to, those derived from the following inorganic acids: hydrochloric, hydrobromic, hydroiodic, sulfuric, sulfurous, nitric, nitrous, phosphoric, and phosphorous.

Examples of suitable organic anions include, but are not limited to, those derived from the following organic acids: 2-acetyoxybenzoic, acetic, ascorbic, aspartic, benzoic, camphorsulfonic, cinnamic, citric, edetic, ethanedisulfonic, ethanesulfonic, fumaric, glucheptonic, gluconic, glutamic, glycolic, hydroxymaleic, hydroxynaphthalene carboxylic, isethionic, lactic, lactobionic, lauric, maleic, malic, methanesulfonic, mucic, oleic, oxalic, palmitic, pamoic, pantothenic, phenylacetic, phenylsulfonic, propionic, pyruvic, salicylic, stearic, succinic, sulfanilic, tartaric, toluenesulfonic, and valeric. Examples of suitable polymeric organic anions include, but are not limited to, those derived from the following polymeric acids: tannic acid, carboxymethyl cellulose.

Unless otherwise specified, a reference to a particular compound also includes salt forms thereof.

Chemically Protected Forms

It may be convenient or desirable to prepare, purify, and/or handle the active compound in a chemically protected form. The term "chemically protected form" is used herein in the conventional chemical sense and pertains to a compound in which one or more reactive functional groups are protected from undesirable chemical reactions under specified conditions (e.g., pH, temperature, radiation, solvent, and the like). In practice, well known chemical methods are employed to reversibly render unreactive a functional group, which otherwise would be reactive, under specified conditions. In a chemically protected form, one or more reactive functional groups are in the form of a protected or protecting group (also known as a masked or masking group or a blocked or blocking group). By protecting a reactive functional group, reactions involving other unprotected reactive functional groups can be performed, without affecting the protected group; the protecting group may be removed, usually in a subsequent step, without substantially affecting the remainder of the molecule. See, for example, Protective Groups in Organic Synthesis (T. Green and P. Wuts; 3rd Edition; John Wiley and Sons, 1999). Unless otherwise specified, a reference to a particular compound also includes chemically protected forms thereof.

A wide variety of such "protecting," "blocking," or "masking" methods are widely used and well known in organic synthesis. For example, a compound which has two non-equivalent reactive functional groups, both of which would be reactive under specified conditions, may be derivatized to render one of the functional groups "protected," and therefore unreactive, under the specified conditions; so protected, the compound may be used as a reactant which has effectively only one reactive functional group. After the desired reaction (involving the other functional group) is complete, the protected group may be "deprotected" to return it to its original functionality.

For example, a hydroxy group may be protected as an ether (—OR) or an ester (—OC(=O)R), for example, as: a t-butyl ether; a benzyl, benzhydryl(diphenylmethyl), or trityl(triphenylmethyl)ether; a trimethylsilyl or t-butyldimethylsilyl ether; or an acetyl ester (—OC(=O)CH3, —OAc).

For example, an aldehyde or ketone group may be protected as an acetal (R—CH(OR)2) or ketal (R2C(OR)2), respectively, in which the carbonyl group (>C=O) is converted to a diether (>C(OR)2), by reaction with, for example, a primary alcohol. The aldehyde or ketone group is readily regenerated by hydrolysis using a large excess of water in the presence of acid.

For example, an amine group may be protected, for example, as an amide (—NRCO—R) or a urethane (—NRCO—OR), for example, as: a methyl amide (—NHCO—CH3); a benzyloxy amide (—NHCO—OCH2C6H5, —NH-Cbz); as a t-butoxy amide (—NHCO—OC(CH3)3, —NH-Boc); a 2-biphenyl-2-propoxy amide (—NHCO—OC(CH3)2C6H4C6H5, —NH-Bpoc), as a 9-fluorenylmethoxy amide (—NH-Fmoc), as a 6-nitroveratryloxy amide (—NH-Nvoc), as a 2-trimethylsilylethyloxy amide (—NH-Teoc), as a 2,2,2-trichloroethyloxy amide (—NH-Troc), as an allyloxy amide (—NH-Alloc), as a 2(-phenylsulphonyl)ethyloxy amide (—NH-Psec); or, in suitable cases (e.g., cyclic amines), as a nitroxide radical (>N=O<<).

For example, a carboxylic acid group may be protected as an ester for example, as: an Cˆalkyl ester (e.g., a methyl ester; a t-butyl ester); a Cvrhaloalkyl ester (e.g., a C1-7-trihaloalkyl ester); a triC1-7alkylsilyl-Ci.7alkyl ester; or a C5.2oaryl-C1-7alkyl ester (e.g., a benzyl ester; a nitrobenzyl ester); or as an amide, for example, as a methyl amide.

For example, a thiol group may be protected as a thioether (—SR), for example, as: a benzyl thioether; an acetamidomethyl ether (—S—CH2NHC(=O)CH3).

Prodrugs

It may be convenient or desirable to prepare, purify, and/or handle the active compound in the form of a prodrug. The term "prodrug," as used herein, pertains to a compound which, when metabolised (e.g., in vivo), yields the desired active compound. Typically, the prodrug is inactive, or less active than the active compound, but may provide advantageous handling, administration, or metabolic properties.

Unless otherwise specified, a reference to a particular compound also includes prodrugs thereof.

For example, some prodrugs are esters of the active compound (e.g., a physiologically acceptable metabolically labile ester). During metabolism, the ester group (—C(=O)OR) is cleaved to yield the active drug. Such esters may be formed by esterification, for example, of any of the carboxylic acid groups (—C(=O)OH) in the parent compound, with, where appropriate, prior protection of any other reactive groups present in the parent compound, followed by deprotection if required.

Also, some prodrugs are activated enzymatically to yield the active compound, or a compound which, upon further chemical reaction, yields the active compound (for example, as in ADEPT, GDEPT, LIDEPT, etc.). For example, the prodrug may be a sugar derivative or other glycoside conjugate, or may be an amino acid ester derivative.

Chemical Synthesis

The synthesis method may employ protective groups, for example, O-protecting groups, such as groups known to be suitable for protecting primary and/or secondary hydroxy groups, for example, the O-protecting groups mentioned in "Protective Groups in Organic Chemistry", edited by J. W. F. McOmie, Plenum Press (1973), and "Protective Groups in Organic Synthesis", 3rd edition, T. W. Greene & P. G. M. Wutz, Wiley-Interscience (1999). Some preferred O-protecting groups include alkylcarbonyl and arylcarbonyl groups (e.g., acyl, e.g., benzoyl), triarylmethyl groups (e.g., triphenylmethyl(trityl) and dimethoxytrityl) and silyl groups (e.g., trialkylsilyl, such as trimethylsilyl).

Nucleic Acid Based Inhibitors

Nucleic acid-based inhibitors for inhibition IDH, e.g., IDH1, can be, e.g., double stranded RNA (dsRNA) that function, e.g., by an RNA interference (RNAi mechanism), an antisense RNA, or a microRNA (miRNA). In an embodiment the nucleic-acid based inhibitor binds to the target mRNA and inhibits the production of protein therefrom, e.g., by cleavage of the target mRNA.

Double Stranded RNA (dsRNA)

A nucleic acid based inhibitor useful for decreasing an IDH1-97$^{neo}$, e.g., IDH1-G97D, or IDH2-137$^{neo}$, mutant function is, e.g., a dsRNA, such as a dsRNA that acts by an RNAi mechanism. RNAi refers to the process of sequence-specific post-transcriptional gene silencing in animals mediated by short interfering RNAs (siRNAs). dsRNAs as used herein are understood to include siRNAs. Typically, inhibition of IDH, e.g., IDH1, by dsRNAs does not trigger the interferon response that results from dsRNA-mediated activation of protein kinase PKR and 2',5'-oligoadenylate synthetase resulting in non-specific cleavage of mRNA by ribonuclease L.

dsRNAs targeting an IDH1-97$^{neo}$, e.g., IDH1-G97D, or IDH2-137$^{neo}$, enzyme, e.g., a wildtype or mutant IDH1 or IDH2, can be unmodified or chemically modified. The dsRNA can be chemically synthesized, expressed from a vector or enzymatically synthesized. The invention also features various chemically modified synthetic dsRNA molecules capable of modulating IDH1 or IDH2 gene expression or activity in cells by RNA interference (RNAi). The use of chemically modified dsRNA improves various properties of native dsRNA molecules, such as through increased resistance to nuclease degradation in vivo and/or through improved cellular uptake.

The dsRNAs targeting nucleic acid can be composed of two separate RNAs, or of one RNA strand, which is folded to form a hairpin structure. Hairpin dsRNAs are typically referred to as shRNAs.

An shRNA that targets IDH, e.g., a mutant or wildtype IDH1 or IDH2 gene can be expressed from a vector, e.g., viral vector, such as a lentiviral or adenoviral vector. In certain embodiments, a suitable dsRNA for inhibiting expression of an IDH1 gene will be identified by screening an siRNA library, such as an adenoviral or lentiviral siRNA library.

In an embodiment, a dsRNA that targets IDH, e.g., IDH1 or IDH2, is about 15 to about 30 base pairs in length (e.g., about 16, 17, 18, 19, 20, 21, 22, 23, 24, 25, 26, 27, 28, or 29) base pairs in length. In another embodiment, the dsRNA includes overhanging ends of about 1 to about 3 (e.g., about 1, 2, or 3) nucleotides. By "overhang" is meant that 3'-end of one strand of the dsRNA extends beyond the 5'-end of the other strand, or vice versa. The dsRNA can have an overhang on one or both ends of the dsRNA molecule. In some embodiments, the single-stranded overhang is located at the 3'-terminal end of the antisense strand, or, alternatively, at the 3'-terminal end of the sense strand. In some embodiments, the overhang is a TT or UU dinucleotide overhang, e.g., a TT or UU dinucleotide overhang. For example, in an embodiment, the dsRNA includes a 21-nucleotide antisense strand, a 19 base pair duplex region, and a 3'-terminal dinucleotide. In yet another embodiment, a dsRNA includes a duplex nucleic acid where both ends are blunt, or alternatively, where one of the ends is blunt.

In an embodiment, the dsRNA includes a first and a second strand, each strand is about 18 to about 28 nucleotides in length, e.g., about 19 to about 23 nucleotides in length, the first strand of the dsRNA includes a nucleotide sequence having sufficient complementarity to the IDH, e.g., IDH1 or IDH2, RNA for the dsRNA to direct cleavage of the IDH, e.g., IDH1, mRNA via RNA interference, and the second strand of the dsRNA includes a nucleotide sequence that is complementary to the first strand.

In an embodiment, a dsRNA targeting an IDH, e.g., IDH1 or IDH2, gene can target wildtype and mutant forms of the gene, or can target different allelic isoforms of the same gene. For example, the dsRNA will target a sequence that is identical in two or more of the different isoforms.

In an embodiment, a dsRNA will preferentially or specifically target an IDH1-97$^{neo}$ mutation, e.g., IDH1-G97D.

In an embodiment, a dsRNA will preferentially or specifically target an IDH2-137$^{neo}$ mutant.

In an embodiment, a dsRNA targeting an IDH1-97$^{neo}$ mutant, e.g., IDH1-G97D, or IDH2-137$^{neo}$ mutant, RNA includes one or more chemical modifications. Non-limiting examples of such chemical modifications include without limitation phosphorothioate internucleotide linkages, 2'-deoxyribonucleotides, 2'-O-methyl ribonucleotides, 2'-deoxy-2'-fluoro ribonucleotides, "universal base" nucleotides, "acyclic" nucleotides, 5-C-methyl nucleotides, and terminal glyceryl and/or inverted deoxy abasic residue incorporation. Such chemical modifications have been shown to preserve RNAi activity in cells while at the same time, dramatically increasing the serum stability of these compounds. Furthermore, one or more phosphorothioate substitutions are well-tolerated and have been shown to confer substantial increases in serum stability for modified dsRNA constructs.

In an embodiment, a dsRNA targeting an IDH1-97$^{neo}$ mutant, e.g., IDH1-G97D, or IDH2-137$^{neo}$ mutant, RNA includes modified nucleotides while maintaining the ability to mediate RNAi. The modified nucleotides can be used to improve in vitro or in vivo characteristics such as stability, activity, and/or bioavailability. For example, the dsRNA can include modified nucleotides as a percentage of the total number of nucleotides present in the molecule. As such, the dsRNA can generally include about 5% to about 100% modified nucleotides (e.g., about 5%, 10%, 15%, 20%, 25%, 30%, 35%, 40%, 45%, 50%, 55%, 60%, 65%, 70%, 75%, 80%, 85%, 90%, 95% or 100% modified nucleotides).

In some embodiments, the dsRNA targeting an IDH1-97$^{neo}$ mutant, e.g., IDH1-G97D, or IDH2-137$^{neo}$ mutant, RNA is about 21 nucleotides long. In another embodiment, the dsRNA does not contain any ribonucleotides, and in another embodiment, the dsRNA includes one or more ribonucleotides. In an embodiment, each strand of the dsRNA molecule independently includes about 15 to about 30 (e.g., about 15, 16, 17, 18, 19, 20, 21, 22, 23, 24, 25, 26, 27, 28, 29, or 30) nucleotides, wherein each strand includes about 15 to about 30 (e.g., about 15, 16, 17, 18, 19, 20, 21, 22, 23, 24, 25, 26, 27, 28, 29, or 30) nucleotides that are complementary to the nucleotides of the other strand. In an embodiment, one of the strands of the dsRNA includes a nucleotide sequence that is complementary to a nucleotide sequence or a portion thereof of an IDH1-97$^{neo}$ mutant, e.g., IDH1-G97D, or IDH2-137$^{neo}$ mutant, gene, and the second strand of the dsRNA includes a nucleotide sequence substantially similar to the nucleotide sequence of the IDH1 or IDH2 or a portion thereof.

In an embodiment, the dsRNA targeting an IDH1-97$^{neo}$ mutant, e.g., IDH1-G97D, or IDH2-137$^{neo}$ mutant, RNA includes an antisense region having a nucleotide sequence that is complementary to a nucleotide sequence of the IDH1 or IDH2 gene or a portion thereof, and a sense region having a nucleotide sequence substantially similar to the nucleotide sequence of the IDH1 or IDH2 gene or a portion thereof. In an embodiment, the antisense region and the sense region independently include about 15 to about 30 (e.g., about 15, 16, 17, 18, 19, 20, 21, 22, 23, 24, 25, 26, 27, 28, 29, or 30) nucleotides, where the antisense region includes about 15 to about 30 (e.g., about 15, 16, 17, 18, 19, 20, 21, 22, 23, 24, 25, 26, 27, 28, 29, or 30) nucleotides that are complementary to nucleotides of the sense region.

As used herein, the term "dsRNA" is meant to include nucleic acid molecules that are capable of mediating sequence specific RNAi, such as short interfering RNA (siRNA), short hairpin RNA (shRNA), short interfering oligonucleotide, short interfering nucleic acid, short interfering modified oligonucleotide, chemically modified siRNA, post-transcriptional gene silencing RNA (ptgsRNA), and others. In addition, as used herein, the term "RNAi" is meant to include sequence specific RNA interference, such as post transcriptional gene silencing, translational inhibition, or epigenetics.

Nucleic Acid-Based IDH Inhibitors

In an embodiment the inhibitor is a nucleic acid-based inhibitor, such as a double stranded RNA (dsRNA) or antisense RNA that targets an IDH1-97$^{neo}$, e.g., IDH1-G97D, mutant.

In one embodiment, the nucleic acid based inhibitor decreases or inhibits expression of an IDH1 having other than Gly at residue 97, e.g., having Asp, Ser, Arg, Cys, Ala, or Val at residue 97, according to the amino acid sequence of SEQ ID NO:8 (see also FIG. 2). In one embodiment, the nucleic acid based inhibitor decreases or inhibits expression of an IDH1 enzyme having Asp at residue 97.

In an embodiment the nucleic acid-based inhibitor is a dsRNA that targets an mRNA that encodes an IDH1 allele described herein, e.g., an IDH1 allele having other than a Gly at residue 97. E.g., the allele can have Asp, Ser, Arg, Cys, Ala, or Val at residue 97, according to the sequence of SEQ ID NO:8 (see also FIG. 2).

In an embodiment the allele encodes an IDH1 having Asp at residue 97.

In an embodiment, the nucleic acid-based inhibitor is a dsRNA that targets IDH1, e.g., an IDH1 having an A or C or T (or a nucleotide other than G) at nucleotide position 289, or an A or T or C (or a nucleotide other than G) at nucleotide position 290, e.g., a mutant allele carrying a G289A or a G289C or a G289T mutation, or a G290A or a G290C or a G290T mutation according to the IDH1 sequence of SEQ ID NO:9 (FIG. 2A).

In an embodiment, the nucleic acid-based inhibitor is a dsRNA that targets IDH1, e.g., an IDH1 having an A at nucleotide position 289 or a C at nucleotide position 289 or a T at nucleotide position 289, according to the IDH1 sequence of SEQ ID NO:9.

In an embodiment, the nucleic acid-based inhibitor is a dsRNA that targets IDH1, e.g., an IDH1 having an A at nucleotide position 290 or a C at nucleotide position 290 or a T at nucleotide position 290, according to the IDH1 sequence of SEQ ID NO:9.

In an embodiment, the dsRNA targets an IDH1 having other than G, e.g., an A or C or T, at nucleotide position 289, or other than G, e.g., an A or C or T at position 290, or other than C, e.g., A or G or T at nucleotide position 291 (e.g., a mutant), and an IDH1 having a G at nucleotide position 289 or a G at nucleotide position 290 or a C at position 291 (e.g., a wildtype), e.g., by targeting a region of the IDH1 mRNA that is identical between the wildtype and mutant transcripts. In yet another embodiment, the dsRNA targets a particular mutant or polymorphism (such as a single nucleotide polymorphism (SNP)), but not a wildtype allele. In this case, the nucleic acid based inhibitor, e.g., a dsRNA, targets the region of the IDH1 containing the mutation.

In some embodiments, the nucleic acid based inhibitor, e.g., a dsRNA, preferentially or specifically inhibits the product of a mutant IDH1 as compared to the product of a wildtype IDH1. For example, in one embodiment, a dsRNA targets a region of an IDH1 mRNA that carries the mutation (e.g., a G289A or G289C or G289T or G290A or G290C or G290T mutation according to SEQ ID NO:9 (FIG. 2A).

In one embodiment, the nucleic acid-based inhibitor is a dsRNA including a sense strand and an antisense strand having a primary sequence presented in Tables 1-7. In another embodiment, the nucleic acid based inhibitor is an antisense oligonucleotide that includes all or a part of an antisense primary sequence presented in Tables 1-7 or which targets the same or substantially the same region as does a dsRNA from Tables 1-7.

In an embodiment, the nucleic acid based inhibitor is delivered to the brain, e.g., directly to the brain, e.g., by intrathecal or intraventricular delivery. The nucleic acid based inhibitor can also be delivered from an inplantable device. In an embodiment, the nucleic acid-based inhibitor is delivered by infusion using, e.g., a catheter, and optionally, a pump.

Antisense

Suitable nucleic acid based inhibitors include antisense nucleic acids. While not being bound by theory it is believed that antisense inhibition is typically based upon hydrogen bonding-based hybridization of oligonucleotide strands or segments such that at least one strand or segment is cleaved, degraded, or otherwise rendered inoperable.

An antisense agent can bind an IDH1-97$^{neo}$ mutant, e.g., IDH1-G97D, or IDH2-137$^{neo}$ mutant, DNA. In embodiments it inhibits replication and transcription. While not being bound by theory it is believed that an antisense agent can also function to inhibit target RNA translocation, e.g., to a site of protein translation, translation of protein from the RNA, splicing of the RNA to yield one or more RNA species, and catalytic activity or complex formation involving the RNA.

An antisense agent can have a chemical modification described above as being suitable for dsRNA.

Antisense agents can include, for example, from about 8 to about 80 nucleobases (i.e., from about 8 to about 80 nucleotides), e.g., about 8 to about 50 nucleobases, or about 12 to about 30 nucleobases. Antisense compounds include ribozymes, external guide sequence (EGS) oligonucleotides (oligozymes), and other short catalytic RNAs or catalytic oligonucleotides which hybridize to the target nucleic acid and modulate its expression. Anti-sense compounds can include a stretch of at least eight consecutive nucleobases that are complementary to a sequence in the target gene. An oligonucleotide need not be 100% complementary to its target nucleic acid sequence to be specifically hybridizable. An oligonucleotide is specifically hybridizable when binding of the oligonucleotide to the target interferes with the normal function of the target molecule to cause a loss of utility, and there is a sufficient degree of complementarity to avoid non-specific binding of the oligonucleotide to non-target sequences under conditions in which specific binding is desired, i.e., under physiological conditions in the case of in vivo assays or therapeutic treatment or, in the case of in vitro assays, under conditions in which the assays are conducted.

Hybridization of antisense oligonucleotides with an IDH1-97$^{neo}$ mutant, e.g., IDH1-G97D, or IDH2-137$^{neo}$ mutant, RNA can interfere with one or more of the normal functions of mRNA. While not being bound by theory it is believed that the functions of mRNA to be interfered with include all key functions such as, for example, translocation of the RNA to the site of protein translation, translation of protein from the RNA, splicing of the RNA to yield one or more mRNA species, and catalytic activity which may be engaged in by the RNA. Binding of specific protein(s) to the RNA may also be interfered with by antisense oligonucleotide hybridization to the RNA.

Exemplary antisense compounds include DNA or RNA sequences that specifically hybridize to the target nucleic acid, e.g., an IDH1-97$^{neo}$ mutant, e.g., IDH1-G97D, or IDH2-137$^{neo}$ mutant, RNA. The complementary region can extend for between about 8 to about 80 nucleobases. The compounds can include one or more modified nucleobases. Modified nucleobases may include, e.g., 5-substituted pyrimidines such as 5-iodouracil, 5-iodocytosine, and C5-propynyl pyrimidines such as C5-propynylcytosine and C5-propynyluracil. Other suitable modified nucleobases include $N^4$—($C_1$-$C_{12}$) alkylaminocytosines and $N^4,N^4$—($C_1$-$C_{12}$) dialkylaminocytosines. Modified nucleobases may also include 7-substituted-5-aza-7-deazapurines and 7-substituted-7-deazapurines such as, for example, 7-iodo-7-deazapurines, 7-cyano-7-deazapurines, 7-aminocarbonyl-7-deazapurines. Examples of these include 6-amino-7-iodo-7-deazapurines, 6-amino-7-cyano-7-deazapurines, 6-amino-7-aminocarbonyl-7-deazapurines, 2-amino-6-hydroxy-7-iodo-7-deazapurines, 2-amino-6-hydroxy-7-cyano-7-deazapurines, and 2-amino-6-hydroxy-7-aminocarbonyl-7-deazapurines. Furthermore, $N^6$—($C_1$-$C_{12}$) alkylaminopurines and $N^6,N^6$—($C_1$-$C_{12}$) dialkylaminopurines, including $N^6$-methylaminoadenine and $N^6,N^6$-dimethylaminoadenine, are also suitable modified nucleobases. Similarly, other 6-substituted purines including, for example, 6-thioguanine may constitute appropriate modified nucleobases. Other suitable nucleobases include 2-thiouracil, 8-bromoadenine, 8-bromoguanine, 2-fluoroadenine, and 2-fluoroguanine. Derivatives of any of the aforementioned modified nucleobases are also appropriate. Substituents of any of the preceding compounds may include $C_1$-$C_{30}$ alkyl, $C_2$-$C_{30}$ alkenyl, $C_2$-$C_{30}$ alkynyl, aryl, aralkyl, heteroaryl, halo, amino, amido, nitro, thio, sulfonyl, carboxyl, alkoxy, alkylcarbonyl, alkoxycarbonyl, and the like.

MicroRNA

In some embodiments, the nucleic acid-based inhibitor suitable for targeting an IDH1-97$^{neo}$ mutant, e.g., IDH1-G97D, or IDH2-137$^{neo}$ mutant, is a microRNA (miRNA). A miRNA is a single stranded RNA that regulates the expression of target mRNAs either by mRNA cleavage, translational repression/inhibition or heterochromatic silencing. The miRNA is 18 to 25 nucleotides, typically 21 to 23 nucleotides in length. In some embodiments, the miRNA includes chemical modifications, such as one or more modifications described herein.

In some embodiments, a nucleic acid based inhibitor targeting IDH has partial complementarity (i.e., less than 100% complementarity) with the target IDH1 or IDH2, mRNA. For example, partial complementarity can include various mismatches or non-base paired nucleotides (e.g., 1, 2, 3, 4, 5 or more mismatches or non-based paired nucleotides, such as nucleotide bulges), which can result in bulges, loops, or overhangs that result between the antisense strand or antisense region of the nucleic acid-based inhibitor and the corresponding target nucleic acid molecule.

The nucleic acid-based inhibitors described herein, e.g., antisense nucleic acid described herein, can be incorporated into a gene construct to be used as a part of a gene therapy protocol to deliver nucleic acids that can be used to express and produce agents within cells. Expression constructs of such components may be administered in any biologically-effective carrier, e.g., any formulation or composition capable of effectively delivering the component gene to cells in vivo. Approaches include insertion of the subject gene in viral vectors including recombinant retroviruses, adenovirus, adeno-associated virus, lentivirus, and herpes simplex virus-1, or recombinant bacterial or eukaryotic plasmids. Viral vectors transfect cells directly; plasmid DNA can be delivered with the help of, for example, cationic liposomes (lipofectin) or derivatized (e.g., antibody conjugated) polylysine conjugates, gramacidin S, artificial viral envelopes or other such intracellular earners, as well as direct injection of the gene construct or $CaPO_4$ precipitation carried out in vivo.

In an embodiment, in vivo introduction of nucleic acid into a cell includes use of a viral vector containing nucleic acid, e.g., a cDNA. Infection of cells with a viral vector has the advantage that a large proportion of the targeted cells can receive the nucleic acid. Additionally, molecules encoded within the viral vector, e.g., by a cDNA contained in the viral vector, are expressed efficiently in cells which have taken up viral vector nucleic acid.

Retroviral vectors and adeno-associated virus vectors can be used as a recombinant gene delivery system for the transfer of exogenous genes in vivo particularly into humans. These vectors provide efficient delivery of genes into cells, and the transferred nucleic acids are stably integrated into the chromosomal DNA of the host. Protocols for producing recombinant retroviruses and for infecting cells in vitro or in vivo with such viruses can be found in Current Protocols in Molecular Biology, Ausubel, F. M. et al. (eds.) Greene Publishing Associates (1989), Sections 9.10-9.14 and other standard laboratory manuals. Examples of suitable retroviruses include pLJ, pZIP, pWE, and pEM which are known to those skilled in the art. Examples of suitable packaging virus lines for preparing both ecotropic and amphotropic retroviral systems include Crip, Cre, 2, and Am. Retroviruses have been used to introduce a variety of genes into many different cell types, including epithelial cells, in vitro and/or in vivo (see, for example, Eglitis et al. (1985) Science 230:1395-1398; Danos and Mulligan (1988) Proc. Natl. Acad. Sci. USA 85:6460-6464; Wilson et al. (1988) Proc. Natl. Acad. Sci. USA 85:3014-3018; Armentano et al. (1990) Proc. Natl. Acad. Sci. USA 87:6141-6145; Huber et al. (1991) Proc. Natl. Acad. Sci. USA 88:8039-8043; Ferry et al. (1991) Proc. Natl. Acad. Sci. USA 88:8377-8381; Chowdhury et al. (1991) Science 254:1802-1805; van Beusechem et al. (1992) Proc. Natl. Acad. Sci. USA 89:7640-7644; Kay et al. (1992) Human Gene Therapy 3:641-647; Dai et al. (1992) Proc. Natl. Acad. Sci. USA 89:10892-10895; Hwu et al. (1993) J. Immunol. 150:4104-4115; U.S. Pat. Nos. 4,868,116 and 4,980,286; PCT Pub. Nos. WO 89/07136, WO 89/02468, WO 89/05345, and WO 92/07573).

Another viral gene delivery system utilizes adenovirus-derived vectors. See, for example, Berkner et al. (1988) BioTechniques 6:616; Rosenfeld et al. (1991) Science 252:431-434; and Rosenfeld et al. (1992) Cell 68:143-155. Suitable adenoviral vectors derived from the adenovirus strain Ad type 5 d1324 or other strains of adenovirus (e.g., Ad2, Ad3, Ad7 etc.) are known to those skilled in the art.

Yet another viral vector system useful for delivery of the subject gene is the adeno-associated virus (AAV). See, for example, Flotte et al. (1992) Am. J. Respir. Cell. Mol. Biol. 7:349-356; Samulski et al. (1989) J. Virol. 63:3822-3828; and McLaughlin et al. (1989) J. Virol. 62:1963-1973.

Pharmaceutical Compositions

The compositions delineated herein include the compounds delineated herein, as well as additional therapeutic agents if present, in amounts effective for achieving a modulation of disease or disease symptoms, including those described herein.

The term "pharmaceutically acceptable carrier or adjuvant" refers to a carrier or adjuvant that may be administered to a patient, together with a compound of this invention, and which does not destroy the pharmacological activity thereof and is nontoxic when administered in doses sufficient to deliver a therapeutic amount of the compound.

Pharmaceutically acceptable carriers, adjuvants and vehicles that may be used in the pharmaceutical compositions of this invention include, but are not limited to, ion exchangers, alumina, aluminum stearate, lecithin, self-emulsifying drug delivery systems (SEDDS) such as d-α-tocopherol polyethyleneglycol 1000 succinate, surfactants used in pharmaceutical dosage forms such as Tweens or other similar polymeric delivery matrices, serum proteins, such as human serum albumin, buffer substances such as phosphates, glycine, sorbic acid, potassium sorbate, partial glyceride mixtures of saturated vegetable fatty acids, water, salts or electrolytes, such as protamine sulfate, disodium hydrogen phosphate, potassium hydrogen phosphate, sodium chloride, zinc salts, colloidal silica, magnesium trisilicate, polyvinyl pyrrolidone, cellulose-based substances, polyethylene glycol, sodium carboxymethylcellulose, polyacrylates, waxes, polyethylene-polyoxypropylene-block polymers, polyethylene glycol and wool fat. Cyclodextrins such as α-, β-, and γ-cyclodextrin, or chemically modified derivatives such as hydroxyalkylcyclodextrins, including 2- and 3-hydroxypropyl-β-cyclodextrins, or other solubilized derivatives may also be advantageously used to enhance delivery of compounds of the formulae described herein.

The pharmaceutical compositions containing inhibitors of IDH1 or IDH2, may be administered directly to the central nervous system, such as into the cerebrospinal fluid or into the brain. Delivery can be, for example, in a bolus or by continuous pump infusion. In certain embodiments, delivery is by intrathecal delivery or by intraventricular injection directly into the brain. A catheter and, optionally, a pump can be used for delivery. The inhibitors can be delivered in and released from an implantable device, e.g., a device that is implanted in association with surgical removal of tumor tissue. E.g., for delivery to the brain, the delivery can be analogous to that with Gliadel, a biopolymer wafer designed to deliver carmustine directly into the surgical cavity created when a brain tumor is resected. The Gliadel wafer slowly dissolves and delivers carmustine.

The therapeutics disclosed herein, e.g., nucleic acid based inhibitors, e.g. siRNAs can be administered directly to the CNS, e.g., the brain, e.g., using a pump and/or catheter system. In one embodiment, the pump is implanted under the skin. In an embodiment and a catheter attached to a pump is inserted into the CNS, e.g., into the brain or spine. In one embodiment, the pump (such as the IsoMed Drug Pump from Medtronic) delivers dosing, e.g, constant dosing, of a nucleic acid based inhibitor. In an embodiment, the pump is programmable to administer variable or constant doses at predetermined time intervals. For example, the IsoMed Drug pump from Medtronic (or a similar device) can be used to administer a constant supply of the inhibitor, or the SynchroMedII Drug Pump (or a similar device) can be used to administer a variable dosing regime.

Methods and devices described in U.S. Pat. Nos. 7,044,932, 6,620,151, 6,283,949, and 6,685,452 can be used in methods described herein.

The pharmaceutical compositions of this invention may be administered orally, parenterally, by inhalation, topically, rectally, nasally, buccally, vaginally or via an implanted reservoir, preferably by oral administration or administration by injection. The pharmaceutical compositions of this invention may contain any conventional non-toxic pharmaceutically-acceptable carriers, adjuvants or vehicles. In some cases, the pH of the formulation may be adjusted with pharmaceutically acceptable acids, bases or buffers to enhance the stability of the formulated compound or its delivery form. The term parenteral as used herein includes subcutaneous, intracutaneous, intravenous, intramuscular, intraarticular, intraarterial, intrasynovial, intrasternal, intrathecal, intralesional and intracranial injection or infusion techniques.

The pharmaceutical compositions may be in the form of a sterile injectable preparation, for example, as a sterile injectable aqueous or oleaginous suspension. This suspension may be formulated according to techniques known in the art using suitable dispersing or wetting agents (such as, for example, Tween 80) and suspending agents. The sterile injectable preparation may also be a sterile injectable solution or suspension in a non-toxic parenterally acceptable diluent or solvent, for example, as a solution in 1,3-butanediol. Among the acceptable vehicles and solvents that may be employed are mannitol, water, Ringer's solution and isotonic sodium chloride solution. In addition, sterile, fixed oils are conventionally employed as a solvent or suspending medium. For this purpose, any bland fixed oil may be employed including synthetic mono- or diglycerides. Fatty acids, such as oleic acid and its glyceride derivatives are useful in the preparation of injectables, as are natural pharmaceutically-acceptable oils, such as olive oil or castor oil, especially in their polyoxyethylated versions. These oil solutions or suspensions may also contain a long-chain alcohol diluent or dispersant, or carboxymethyl cellulose or similar dispersing agents which are commonly used in the formulation of pharmaceutically acceptable dosage forms such as emulsions and or suspensions. Other commonly used surfactants such as Tweens or Spans and/or other similar emulsifying agents or bioavailability enhancers which are commonly used in the manufacture of pharmaceutically acceptable solid, liquid, or other dosage forms may also be used for the purposes of formulation.

The pharmaceutical compositions of this invention may be orally administered in any orally acceptable dosage form including, but not limited to, capsules, tablets, emulsions and aqueous suspensions, dispersions and solutions. In the case of tablets for oral use, carriers which are commonly used include lactose and corn starch. Lubricating agents, such as magnesium stearate, are also typically added. For oral administration in a capsule form, useful diluents include lactose and dried corn starch. When aqueous suspensions and/or emulsions are administered orally, the active ingredient may be suspended or dissolved in an oily phase is combined with emulsifying and/or suspending agents. If desired, certain sweetening and/or flavoring and/or coloring agents may be added.

The pharmaceutical compositions of this invention may also be administered in the form of suppositories for rectal administration. These compositions can be prepared by mixing a compound of this invention with a suitable non-irritating excipient which is solid at room temperature but liquid at the rectal temperature and therefore will melt in the rectum to release the active components. Such materials include, but are not limited to, cocoa butter, beeswax and polyethylene glycols.

Topical administration of the pharmaceutical compositions of this invention is useful when the desired treatment involves areas or organs readily accessible by topical application. For application topically to the skin, the pharmaceutical composition should be formulated with a suitable ointment containing the active components suspended or dissolved in a carrier. Carriers for topical administration of the compounds of this invention include, but are not limited to, mineral oil, liquid petroleum, white petroleum, propylene glycol, polyoxyethylene polyoxypropylene compound, emulsifying wax and water. Alternatively, the pharmaceutical composition can be formulated with a suitable lotion or cream containing the active compound suspended or dissolved in a carrier with suitable emulsifying agents. Suitable carriers include, but are not limited to, mineral oil, sorbitan monostearate, polysorbate 60, cetyl esters wax, cetearyl alcohol, 2-octyldodecanol, benzyl alcohol and water. The pharmaceutical compositions of this invention may also be topically applied to the lower intestinal tract by rectal suppository formulation or in a suitable enema formulation. Topically-transdermal patches are also included in this invention.

The pharmaceutical compositions of this invention may be administered by nasal aerosol or inhalation. Such compositions are prepared according to techniques well-known in the art of pharmaceutical formulation and may be prepared as solutions in saline, employing benzyl alcohol or other suitable preservatives, absorption promoters to enhance bioavailability, fluorocarbons, and/or other solubilizing or dispersing agents known in the art.

When the compositions of this invention comprise a combination of a compound of the formulae described herein and one or more additional therapeutic or prophylactic agents, both the compound and the additional agent should be present at dosage levels of between about 1 to 100%, and more preferably between about 5 to 95% of the dosage normally administered in a monotherapy regimen. The additional agents may be administered separately, as part of a multiple dose regimen, from the compounds of this invention. Alternatively, those agents may be part of a single dosage form, mixed together with the compounds of this invention in a single composition.

The compounds described herein can, for example, be administered by injection, intravenously, intraarterially, subdermally, intraperitoneally, intramuscularly, or subcutaneously; or orally, buccally, nasally, transmucosally, topically, in an ophthalmic preparation, or by inhalation, with a dosage ranging from about 0.02 to about 100 mg/kg of body weight, alternatively dosages between 1 mg and 1000 mg/dose, every 4 to 120 hours, or according to the requirements of the particular drug. The methods herein contemplate administration of an effective amount of compound or compound composition to achieve the desired or stated effect. Typically, the pharmaceutical compositions of this invention will be administered from about 1 to about 6 times per day or alternatively, as a continuous infusion. Such administration can be used as a chronic or acute therapy. The amount of active ingredient that may be combined with the carrier materials to produce a single dosage form will vary depending upon the host treated and the particular mode of administration. A typical preparation will contain from about 5% to about 95% active compound (w/w). Alternatively, such preparations contain from about 20% to about 80% active compound.

Lower or higher doses than those recited above may be required. Specific dosage and treatment regimens for any particular patient will depend upon a variety of factors, including the activity of the specific compound employed, the age, body weight, general health status, sex, diet, time of administration, rate of excretion, drug combination, the severity and course of the disease, condition or symptoms, the patient's disposition to the disease, condition or symptoms, and the judgment of the treating physician.

Upon improvement of a patient's condition, a maintenance dose of a compound, composition or combination of this invention may be administered, if necessary. Subsequently, the dosage or frequency of administration, or both, may be reduced, as a function of the symptoms, to a level at which the improved condition is retained when the symptoms have been alleviated to the desired level. Patients may, however, require intermittent treatment on a long-term basis upon any recurrence of disease symptoms.

Kits

A compound described herein can be provided in a kit.

In an embodiment the kit includes (a) a compound described herein, e.g., a composition that includes a compound described herein (wherein, e.g., the compound can be an inhibitor described herein), and, optionally (b) informational material. The informational material can be descriptive, instructional, marketing or other material that relates to the methods described herein and/or the use of a compound described herein for the methods described herein.

In an embodiment the kit provides materials for evaluating a subject. The evaluation can be, e.g., for: identifying a subject having unwanted levels (e.g., higher than present in normal or wildtype cells) of any of 2HG, 2HG neoactivity, or mutant IDH1-97$^{neo}$, e.g., IDH1-G97D, or IDH2-137$^{neo}$, protein having 2HG neoactivity (or corresponding RNA), or having an IDH1-97$^{neo}$ mutant, e.g., IDH1-G97D, or IDH2-137$^{neo}$, mutant, characterized by 2HG neoactivity; diagnosing, prognosing, or staging, a subject, e.g., on the basis of having unwanted levels of 2HG, 2HG neoactivity, or an IDH1-97$^{neo}$ mutant, e.g., IDH1-G97D, or IDH2-137$^{neo}$, mutant protein having 2HG neoactivity (or corresponding RNA), or having an IDH1-97$^{neo}$ mutant, e.g., IDH1-G97D, or IDH2-137$^{neo}$, mutant, characterized by 2HG neoactivity; selecting a treatment for, or evaluating the efficacy of, a treatment, e.g., on the basis of the subject having unwanted levels of 2HG, 2HG neoactivity, or an IDH1-97$^{neo}$ mutant, e.g., IDH1-G97D, or IDH2-137$^{neo}$, mutant protein having 2HG neoactivity (or corresponding RNA), or having an IDH1-97$^{neo}$ mutation, e.g., IDH1-G97D, or IDH2-137$^{neo}$, mutation, characterized by 2HG neoactivity. The kit can include one or more reagent useful in the evaluation, e.g., reagents mentioned elsewhere herein. A detection reagent, e.g., an antibody or other specific binding reagent can be included. Standards or reference samples, e.g., a positive or negative control standard can be included. E.g., if the evaluation is based on the presence of 2HG the kit can include a reagent, e.g, a positive or negative control standards for an assay, e.g., a LC-MS assay. If the evaluation is based on the presence of 2HG neoactivity, the kit can include a reagent, e.g., one or more of those mentioned elsewhere herein, for assaying 2HG neoactivity. If the evaluation is based on sequencing, the kit can include primers or other materials useful for sequencing the relevant nucleic acids. E.g., the kit can contain a reagent that provides for interrogation of the identity, i.e., sequencing of, residue 97 of IDH1 to determine if an IDH1-97$^{neo}$ mutant, e.g., IDH1-G97D, is present, or residue 137 of IDH2 to determine if a, or IDH2-137$^{neo}$, mutant is present. The kit can include nucleic acids, e.g., an oligomer, e.g., primers, which allow sequencing of the nucleotides that encode residue 97 of IDH1 or 137 of IDH2. In an embodiment the kit includes a nucleic acid whose hybridization, or ability to be amplified, is dependent on the identity of residue 97 of IDH1 137 of IDH2. In other embodiments the kit includes a reagent, e.g., an antibody or other specific binding molecule, that can identify the presence of an IDH1-97$^{neo}$ mutant, e.g., IDH1-G97D, or IDH2-137$^{neo}$ mutant, protein. As described below, a kit can also include buffers, solvents, and information related to the evaluation.

In one embodiment, the informational material can include information about production of the compound, molecular weight of the compound, concentration, date of expiration, batch or production site information, and so forth. In one embodiment, the informational material relates to methods for administering the compound.

In one embodiment, the informational material can include instructions to administer a compound described herein in a suitable manner to perform the methods described herein, e.g., in a suitable dose, dosage form, or mode of administration (e.g., a dose, dosage form, or mode of administration described herein). In another embodiment, the informational material can include instructions to administer a compound described herein to a suitable subject, e.g., a human, e.g., a human having or at risk for a disorder described herein.

The informational material of the kits is not limited in its form. In many cases, the informational material, e.g., instructions, is provided in printed matter, e.g., a printed text, drawing, and/or photograph, e.g., a label or printed sheet. However, the informational material can also be provided in other formats, such as Braille, computer readable material, video recording, or audio recording. In another embodiment, the informational material of the kit is contact information, e.g., a physical address, email address, website, or telephone number, where a user of the kit can obtain substantive information about a compound described herein and/or its use in the methods described herein. Of course, the informational material can also be provided in any combination of formats.

In addition to a compound described herein, the composition of the kit can include other ingredients, such as a solvent or buffer, a stabilizer, a preservative, a flavoring agent (e.g., a bitter antagonist or a sweetener), a fragrance or other cosmetic ingredient, and/or a second agent for treating a condition or disorder described herein. Alternatively, the other ingredients can be included in the kit, but in different compositions or containers than a compound described herein. In such embodiments, the kit can include instructions for admixing a compound described herein and the other ingredients, or for using a compound described herein together with the other ingredients.

A compound described herein can be provided in any form, e.g., liquid, dried or lyophilized form. It is preferred that a compound described herein be substantially pure and/or sterile. When a compound described herein is provided in a liquid solution, the liquid solution preferably is an aqueous solution, with a sterile aqueous solution being preferred. When a compound described herein is provided as a dried form, reconstitution generally is by the addition of a suitable solvent. The solvent, e.g., sterile water or buffer, can optionally be provided in the kit.

The kit can include one or more containers for the composition containing a compound described herein. In some embodiments, the kit contains separate containers, dividers or compartments for the composition and informational material. For example, the composition can be contained in a bottle, vial, or syringe, and the informational material can be contained in a plastic sleeve or packet. In other embodiments, the separate elements of the kit are contained within a single, undivided container. For example, the composition is contained in a bottle, vial or syringe that has attached thereto the informational material in the form of a label. In some embodiments, the kit includes a plurality (e.g., a pack) of individual containers, each containing one or more unit dosage forms (e.g., a dosage form described herein) of a compound described herein. For example, the kit includes a plurality of syringes, ampules, foil packets, or blister packs, each containing a single unit dose of a compound described herein. The containers of the kits can be air tight, waterproof (e.g., impermeable to changes in moisture or evaporation), and/or light-tight.

The kit optionally includes a device suitable for administration of the composition, e.g., a syringe, inhalant, pipette, forceps, measured spoon, dropper (e.g., eye dropper), swab (e.g., a cotton swab or wooden swab), or any such delivery device. In an embodiment, the device is a medical implant device, e.g., packaged for surgical insertion.

Combination Therapies

In some embodiments, a compound or composition described herein is administered together with an additional cancer treatment. Exemplary cancer treatments include, for example: surgery, chemotherapy, targeted therapies such as antibody therapies, immunotherapy, and hormonal therapy. Examples of each of these treatments are provided below.

Chemotherapy

In some embodiments, a compound or composition described herein, is administered with a chemotherapy. Chemotherapy is the treatment of cancer with drugs that can destroy cancer cells. "Chemotherapy" usually refers to cytotoxic drugs which affect rapidly dividing cells in general, in contrast with targeted therapy. Chemotherapy drugs interfere with cell division in various possible ways, e.g., with the duplication of DNA or the separation of newly formed chromosomes. Most forms of chemotherapy target all rapidly dividing cells and are not specific for cancer cells, although some degree of specificity may come from the inability of many cancer cells to repair DNA damage, while normal cells generally can.

Examples of chemotherapeutic agents used in cancer therapy include, for example, antimetabolites (e.g., folic acid, purine, and pyrimidine derivatives) and alkylating agents (e.g., nitrogen mustards, nitrosoureas, platinum, alkyl sulfonates, hydrazines, triazenes, aziridines, spindle poison, cytotoxic agents, toposimerase inhibitors and others). Exemplary agents include Aclarubicin, Actinomycin, Alitretinon, Altretamine, Aminopterin, Aminolevulinic acid, Amrubicin, Amsacrine, Anagrelide, Arsenic trioxide, Asparaginase, Atrasentan, Belotecan, Bexarotene, endamustine, Bleomycin, Bortezomib, Busulfan, Camptothecin, Capecitabine, Carboplatin, Carboquone, Carmofur, Carmustine, Celecoxib, Chlorambucil, Chlormethine, Cisplatin, Cladribine, Clofarabine, Crisantaspase, Cyclophosphamide, Cytarabine, Dacarbazine, Dactinomycin, Daunorubicin, Decitabine, Demecolcine, Docetaxel, Doxorubicin, Efaproxiral, Elesclomol, Elsamitrucin, Enocitabine, Epirubicin, Estramustine, Etoglucid, Etoposide, Floxuridine, Fludarabine, Fluorouracil (5FU), Fotemustine, Gemcitabine, Gliadel implants, Hydroxycarbamide, Hydroxyurea, Idarubicin, Ifosfamide, Irinotecan, Irofulven, Ixabepilone, Larotaxel, Leucovorin, Liposomal doxorubicin, Liposomal daunorubicin, Lonidamine, Lomustine, Lucanthone, Mannosulfan, Masoprocol, Melphalan, Mercaptopurine, Mesna, Methotrexate, Methyl aminolevulinate, Mitobronitol, Mitoguazone, Mitotane, Mitomycin, Mitoxantrone, Nedaplatin, Nimustine, Oblimersen, Omacetaxine, Ortataxel, Oxaliplatin, Paclitaxel, Pegaspargase, Pemetrexed, Pentostatin, Pirarubicin, Pixantrone, Plicamycin, Porfimer sodium, Prednimustine, Procarbazine, Raltitrexed, Ranimustine, Rubitecan, Sapacitabine, Semustine, Sitimagene ceradenovec, Strataplatin, Streptozocin, Talaporfin, Tegafur-uracil, Temoporfin, Temozolomide, Teniposide, Tesetaxel, Testolactone, Tetranitrate, Thiotepa, Tiazofurine, Tioguanine, Tipifarnib, Topotecan, Trabectedin, Triaziquone, Triethylenemelamine, Triplatin, Tretinoin, Treosulfan, Trofosfamide, Uramustine, Valrubicin, Verteporfin, Vinblastine, Vincristine, Vindesine, Vinflunine, Vinorelbine, Vorinostat, Zorubicin, and other cytostatic or cytotoxic agents described herein.

Because some drugs work better together than alone, two or more drugs are often given at the same time. Often, two or more chemotherapy agents are used as combination chemotherapy. In some embodiments, the chemotherapy agents (including combination chemotherapy) can be used in combination with a compound described herein, e.g., phenformin.

Targeted Therapy

In some embodiments, a compound or composition described herein, is administered with a targeted therapy. Targeted therapy constitutes the use of agents specific for the deregulated proteins of cancer cells. Small molecule targeted therapy drugs are generally inhibitors of enzymatic domains on mutated, overexpressed, or otherwise critical proteins within the cancer cell. Prominent examples are the tyrosine kinase inhibitors such as Axitinib, Bosutinib, Cediranib, desatinib, erlotinib, imatinib, gefitinib, lapatinib, Lestaurtinib, Nilotinib, Semaxanib, Sorafenib, Sunitinib, and Vandetanib, and also cyclin-dependent kinase inhibitors such as Alvocidib and Seliciclib. Monoclonal antibody therapy is another strategy in which the therapeutic agent is an antibody which specifically binds to a protein on the surface of the cancer cells. Examples include the anti-HER2/neu antibody trastuzumab (HERCEPTIN®) typically used in breast cancer, and the anti-CD20 antibody rituximab and Tositumomab typically used in a variety of B-cell malignancies. Other exemplary antibodies include Cetuximab, Panitumumab, Trastuzumab, Alemtuzumab, Bevacizumab, Edrecolomab, and Gemtuzumab. Exemplary fusion proteins include Aflibercept and Denileukin diftitox. In some embodiments, the targeted therapy can be used in combination with a compound described herein, e.g., a biguanide such as metformin or phenformin, preferably phenformin.

Targeted therapy can also involve small peptides as "homing devices" which can bind to cell surface receptors or affected extracellular matrix surrounding the tumor. Radionuclides which are attached to these peptides (e.g., RGDs) eventually kill the cancer cell if the nuclide decays in the vicinity of the cell. An example of such therapy includes BEXXAR®.

Immunotherapy

In some embodiments, a compound or composition described herein is administered with an immunotherapy. Cancer immunotherapy refers to a diverse set of therapeutic strategies designed to induce the patient's own immune system to fight the tumor. Contemporary methods for generating an immune response against tumors include intravesicular BCG immunotherapy for superficial bladder cancer, and use of interferons and other cytokines to induce an immune response in renal cell carcinoma and melanoma patients.

Allogeneic hematopoietic stem cell transplantation can be considered a form of immunotherapy, since the donor's immune cells will often attack the tumor in a graft-versus-tumor effect. In some embodiments, the immunotherapy agents can be used in combination with a compound or composition described herein.

Hormonal Therapy

In some embodiments, a compound or composition described herein, is administered with a hormonal therapy. The growth of some cancers can be inhibited by providing or blocking certain hormones. Common examples of hormone-sensitive tumors include certain types of breast and prostate cancers. Removing or blocking estrogen or testosterone is often an important additional treatment. In certain cancers, administration of hormone agonists, such as progestogens may be therapeutically beneficial. In some embodiments, the hormonal therapy agents can be used in combination with a compound or a composition described herein.

In some embodiments, a compound or composition described herein, is administered together with an additional cancer treatment (e.g., surgical removal), in treating cancer in nervous system, e.g., cancer in central nervous system, e.g., brain tumor, e.g., glioma, e.g., glioblastoma multiforme (GBM).

Several studies have suggested that more than 25% of glioblastoma patients obtain a significant survival benefit from adjuvant chemotherapy. Meta-analyses have suggested that adjuvant chemotherapy results in a 6-10% increase in 1-year survival rate.

Temozolomide is an orally active alkylating agent that is used for persons newly diagnosed with glioblastoma multiforme. It was approved by the United States Food and Drug Administration (FDA) in March 2005. Studies have shown that the drug was well tolerated and provided a survival benefit. Adjuvant and concomitant temozolomide with radiation was associated with significant improvements in median progression-free survival over radiation alone (6.9 vs 5 mo), overall survival (14.6 vs 12.1 mo), and the likelihood of being alive in 2 years (26% vs 10%).

Nitrosoureas: BCNU (carmustine)-polymer wafers (Gliadel) were approved by the FDA in 2002. Though Gliadel wafers are used by some for initial treatment, they have shown only a modest increase in median survival over placebo (13.8 vs. 11.6 months) in the largest such phase III trial, and are associated with increased rates of CSF leak and increased intracranial pressure secondary to edema and mass effect.

MGMT is a DNA repair enzyme that contributes to temozolomide resistance. Methylation of the MGMT promoter, found in approximately 45% of glioblastoma multiforms, results in an epigenetic silencing of the gene, decreasing the tumor cell's capacity for DNA repair and increasing susceptibility to temozolomide.

When patients with and without MGMT promoter methylation were treated with temozolomide, the groups had median survivals of 21.7 versus 12.7 months, and 2-year survival rates of 46% versus 13.8%, respectively.

Though temozolomide is currently a first-line agent in the treatment of glioblastoma multiforme, unfavorable MGMT methylation status could help select patients appropriate for future therapeutic investigations.

O6-benzylguanine and other inhibitors of MGMT as well as RNA interference-mediated silencing of MGMT offer promising avenues to increase the effectiveness of temozolomide and other alkylating antineoplastics, and such agents are under active study.

Carmustine (BCNU) and cis-platinum (cisplatin) have been the primary chemotherapeutic agents used against malignant gliomas. All agents in use have no greater than a 30-40% response rate, and most fall into the range of 10-20%.

Data from the University of California at San Francisco indicate that, for the treatment of glioblastomas, surgery followed by radiation therapy leads to 1-, 3-, and 5-year survival rates of 44%, 6%, and 0%, respectively. By comparison, surgery followed by radiation and chemotherapy using nitrosourea-based regimens resulted in 1-, 3-, and 5-year survival rates of 46%, 18%, and 18%, respectively.

A major hindrance to the use of chemotherapeutic agents for brain tumors is the fact that the blood-brain barrier (BBB) effectively excludes many agents from the CNS. For this reason, novel methods of intracranial drug delivery are being developed to deliver higher concentrations of chemotherapeutic agents to the tumor cells while avoiding the adverse systemic effects of these medications.

Pressure-driven infusion of chemotherapeutic agents through an intracranial catheter, also known as convection-enhanced delivery (CED), has the advantage of delivering drugs along a pressure gradient rather than by simple diffusion. CED has shown promising results in animal models with agents including BCNU and topotecan.

Initial attempts investigated the delivery of chemotherapeutic agents via an intraarterial route rather than intravenously. Unfortunately, no survival advantage was observed.

Chemotherapy for recurrent glioblastoma multiforme provides modest, if any, benefit, and several classes of agents are used. Carmustine wafers increased 6-month survival from 36% to 56% over placebo in one randomized study of 222 patients, though there was a significant association between the treatment group and serious intracranial infections.

Genotyping of brain tumors may have applications in stratifying patients for clinical trials of various novel therapies.

The anti-angiogenic agent bevacizumab, when used with irinotecan improved 6-month survival in recurrent glioma patients to 46% compared with 21% in patients treated with temozolomide. This bevacizumab and irinotecan combination for recurrent glioblastoma multiforme has been shown to improve survival over bevacizumab alone. Anti-angiogenic agents also decrease peritumoral edema, potentially reducing the necessary corticosteroid dose.

Some glioblastomas responds to gefitinib or erlotinib (tyrosine kinase inhibitors). The simultaneous presence in glioblastoma cells of mutant EGFR (EGFRviii) and PTEN was associated with responsiveness to tyrosine kinase inhibitors, whereas increased p-akt predicts a decreased effect. Other targets include PDGFR, VEGFR, mTOR, farnesyltransferase, and PI3K.

Other possible therapy modalities include imatinib, gene therapy, peptide and dendritic cell vaccines, synthetic chlorotoxins, and radiolabeled drugs and antibodies.

Patient Selection/Monitoring

Described herein are methods of treating a cell proliferation-related disorder characterized by an $IDH1\text{-}97^{neo}$ mutation, e.g., IDH1-G97D, or $IDH2\text{-}137^{neo}$ mutation, e.g., cancer, in a subject and methods of identifying a subject for a treatment described herein. Also described herein are methods of predicting a subject who is at risk of developing cancer characterized by an $IDH1\text{-}97^{neo}$ mutation, e.g., IDH1-G97D, or $IDH2\text{-}137^{neo}$ mutation. The cancer is generally characterized by the presence of characterized by an $IDH1\text{-}97^{neo}$ mutation, e.g., IDH1-G97D, or $IDH2\text{-}137^{neo}$ mutation. The subject can be selected on the basis of the subject having a characterized by an $IDH1\text{-}97^{neo}$ mutation, e.g., IDH1-G97D, or $IDH2\text{-}137^{neo}$ mutation. As used herein, "select" means selecting in whole or part on said basis.

In some embodiments, a subject is selected for treatment with a compound described herein based on a determination that the subject has an $IDH1\text{-}97^{neo}$, e.g., IDH1-G97D, or $IDH2\text{-}137^{neo}$, mutant enzyme. In some embodiments, the patient is selected on the basis of having $IDH1\text{-}97^{neo}$, e.g., IDH1-G97D, or $IDH2\text{-}137^{neo}$, neoactivity. The neoactivity of the enzyme can be identified, for example, by evaluating the subject or sample (e.g., tissue or bodily fluid) therefrom, for the presence or amount of a substrate, cofactor and/or product of the enzyme. The presence and/or amount of substrate, cofactor and/or product can correspond to the wild-type/non-mutant activity or can correspond to the neoactivity of the enzyme. Exemplary bodily fluid that can be used to identify (e.g., evaluate) the neoactivity of the enzyme include amniotic fluid surrounding a fetus, aqueous humour, blood (e.g., blood plasma), Cerebrospinal fluid, cerumen, chyme, Cowper's fluid, female ejaculate, interstitial fluid, lymph, breast milk, mucus (e.g., nasal drainage or phlegm), pleural fluid, pus, saliva, sebum, semen, serum, sweat, tears, urine, vaginal secretion fecal matter, or vomit.

In some embodiments, a subject can be evaluated for neoactivity of an $IDH1\text{-}97^{neo}$ e.g., IDH1-G97D, or $IDH2\text{-}137^{neo}$, mutant enzyme using magnetic resonance. For example, where the neoactivity is conversion of α-ketoglutarate to 2-hydroxyglutarate, the subject can be evaluated for the presence of and/or an elevated amount of 2-hydroxyglutarate, e.g., R-2-hydroxyglutarate relative to the amount of 2-hydroxyglutarate, e.g., R-2-hydroxyglutarate present in a subject who does not have a mutation in IDH1 having the above neoactivity. In some embodiments, neoactivity of an IDH1-97$^{neo}$ mutation, e.g., IDH1-G97D, or IDH2-137$^{neo}$ mutation, can be determined by the presence or elevated amount of a peak corresponding to 2-hydroxyglutarate, e.g., R-2-hydroxyglutarate as determined by magnetic resonance. For example, a subject can be evaluated for the presence and/or strength of a signal at about 2.5 ppm to determine the presence and/or amount of 2-hydroxyglutarate, e.g., R-2-hydroxyglutarate in the subject. This can be correlated to and/or predictive of a neoactivity described herein for the mutant enzyme IDH. Similarly, the presence, strength and/or absence of a signal at about 2.5 ppm could be predictive of a response to treatment and thereby used as a noninvasive biomarker for clinical response.

Neoactivity of an IDH1-97$^{neo}$, e.g., IDH1-G97D, or IDH2-137$^{neo}$, mutant enzyme can also be evaluated using other techniques known to one skilled in the art. For example, the presence or amount of a labeled substrate, cofactor, and/or reaction product can be measured such as a $^{13}$C or $^{14}$C labeled substrate, cofactor, and/or reaction product. The neoactivity can be evaluated by evaluating the forward reaction of the wild-type/non mutant enzyme (such as the oxidative decarboxylation of ioscitrate to α-ketoglutarate in a mutant IDH1 enzyme) and/or the reaction corresponding to the neoactivity (e.g., the conversion of α-ketoglutarate to 2-hydroxyglutarate, e.g., R-2-hydroxyglutarate in a mutant IDH1 enzyme).

Disorders

The IDH1-related methods disclosed herein, e.g., methods of evaluating or treating subjects, are directed to subjects having a cell proliferation-related disorder characterized by an IDH1-97$^{neo}$ mutant, e.g., an IDH1-G97D mutant, or IDH2-137$^{neo}$ mutant, having, e.g., 2HG neoactivity. E.g., it has been shown that cancer cell lines derived from a colon cancer are characterized by an IDH1-97$^{neo}$ mutation, e.g., IDH1-G97D, or IDH2-137$^{neo}$ mutation. Others, e.g., those listed below, can be analyzed, e.g., by sequencing cell samples to determine the presence of an IDH1-97$^{neo}$ mutation, e.g., IDH1-G97D, or IDH2-137$^{neo}$ mutation. Without being bound by theory it is expected that a portion of the tumors of given type of cancer will have an IDH1-97$^{neo}$ mutation, e.g., IDH1-G97D, or IDH2-137$^{neo}$ mutation, having 2HG neoactivity.

The disclosed methods are useful in evaluating or treating proliferative disorders, e.g. evaluating or treating solid tumors, soft tissue tumors, and metastases thereof wherein the solid tumor, soft tissue tumor or metastases thereof is a cancer described herein. Exemplary solid tumors include malignancies (e.g., sarcomas, adenocarcinomas, and carcinomas) of the various organ systems, such as those of brain, lung, breast, lymphoid, gastrointestinal (e.g., colon), and genitourinary (e.g., renal, urothelial, or testicular tumors) tracts, pharynx, prostate, and ovary. Exemplary adenocarcinomas include colorectal cancers, renal-cell carcinoma, liver cancer, non-small cell carcinoma of the lung, and cancer of the small intestine. The disclosed methods are also useful in evaluating or treating non-solid cancers.

The methods described herein can be used with any cancer, for example those described herein, including glioma, AML, ALL (e.g., B-ALL or T-ALL), prostate cancer, or myelodysplasia or myelodysplastic syndrome, thyroid cancer such as follicular thyroid cancer, fibrosarcoma, paraganglioma, melanoma, myeloproliferative neoplasms such as CML, or colorectal cancer Metastases of the aforementioned cancers can also be treated or prevented in accordance with the methods described herein.

The methods described herein are useful in treating cancer in nervous system, e.g., brain tumor, e.g., glioma, e.g., glioblastoma multiforme (GBM), e.g., by inhibiting a neoactivity of an IDH1-97$^{neo}$ mutation, e.g., IDH1-G97D.

Gliomas, a type of brain tumors, can be classified as grade I to grade IV on the basis of histopathological and clinical criteria established by the World Health Organization (WHO). WHO grade I gliomas are often considered benign. Gliomas of WHO grade II or III are invasive, progress to higher-grade lesions. WHO grade IV tumors (glioblastomas) are the most invasive form. Exemplary brain tumors include, e.g., astrocytic tumor (e.g., pilocytic astrocytoma, subependymal giant-cell astrocytoma, diffuse astrocytoma, pleomorphic xanthoastrocytoma, anaplastic astrocytoma, astrocytoma, giant cell glioblastoma, glioblastoma, secondary glioblastoma, primary adult glioblastoma, and primary pediatric glioblastoma); oligodendroglial tumor (e.g., oligodendroglioma, and anaplastic oligodendroglioma); oligoastrocytic tumor (e.g., oligoastrocytoma, and anaplastic oligoastrocytoma); ependymoma (e.g., myxopapillary ependymoma, and anaplastic ependymoma); medulloblastoma; primitive neuroectodermal tumor, schwannoma, meningioma, meatypical meningioma, anaplastic meningioma; and pituitary adenoma. Exemplary cancers are described in Acta Neuropathol (2008) 116:597-602 and N Engl J. Med. 2009 Feb. 19; 360(8):765-73, the contents of which are each incorporated herein by reference.

In embodiments the disorder is glioblastoma.

In an embodiment the disorder is prostate cancer characterized by an IDH1-97$^{neo}$ mutation, e.g., IDH1-G97D, or IDH2-137$^{neo}$ mutation, e.g., stage T1 (e.g., T1a, T1b and T1c), T2 (e.g., T2a, T2b and T2c), T3 (e.g., T3a and T3b) and T4, on the TNM staging system. In embodiments the prostate cancer is grade G1, G2, G3 or G4 (where a higher number indicates greater difference from normal tissue). Types of prostate cancer include, e.g., prostate adenocarcinoma, small cell carcinoma, squamous carcinoma, sarcomas, and transitional cell carcinoma.

Methods and compositions of the invention can be combined with art-known treatment. Art-known treatment for prostate cancer can include, e.g., active surveillance, surgery (e.g., radical prostatectomy, transurethral resection of the prostate, orchiectomy, and cryosurgegry), radiation therapy including brachytherapy (prostate brachytherapy) and external beam radiation therapy, High-Intensity Focused Ultrasound (HIFU), chemotherapy, cryosurgery, hormonal therapy (e.g., antiandrogens (e.g., flutamide, bicalutamide, nilutamide and cyproterone acetate, ketoconazole, aminoglutethimide), GnRH antagonists (e.g., Abarelix)), or a combination thereof.

The methods described herein are useful in treating colon cancer, e.g., by inhibiting a neoactivity of an IDH1-97$^{neo}$ mutation, e.g., IDH1-G97D. Types of colon cancer include adenocarcinoma, leiomyosarcoma, lymphoma, melanoma, and neuroendocrine tumors.

The methods and compositions of the invention can be combined with art-known treatment. Art know treatment for colon cancer can include surgery, chemotherapy, radiation therapy, and/or targeted therapy.

All references described herein are expressly incorporated herein by reference.

EXAMPLES

Example 1

IDH1 Cloning, Mutagenesis, Expression and Purification

1. Wild Type IDH1 was Cloned into pET41a, Creating His8 Tag at C-Terminus

The IDH1 gene coding region (cDNA) was purchased from Invitrogen in pENTR221 vector (www.invitrogen.com, Cat #B-068487_Ultimate_ORF). Oligo nucleotides were designed to PCR out the coding region of IDH1 with NdeI at the 5' end and XhoI at the 3'. (IDH1-f: TAATCATATGTC-CAAAAAAATCAGT (SEQ ID NO:1), IDH1-r: TAATCTC-GAGTGAAAGTTTGGCCTGAGCTAGTT (SEQ ID NO:2)). The PCR product is cloned into the NdeI/XhoI cleaved pET41a vector. NdeI/XhoI cleavage of the vector pET41a releases the GST portion of the plasmid, and creating a C-terminal His8 tag (SEQ ID NO:3) without the N-terminal GST fusion. The original stop codon of IDH1 is change to serine, so the junction sequence in final IDH1 protein is: Ser-Leu-Glu-His-His-His-His-His-His-His-His-Stop (SEQ ID NO:4).

The C-terminal His tag strategy instead of N-terminal His tag strategy was chosen, because C-terminal tag might not negatively impact IDH1 protein folding or activity. See, e.g., Xu X et al, J Biol. Chem. 2004 Aug. 6; 279(32):33946-57.

The sequence for pET41a-IDH1 plasmid is confirmed by DNA sequencing. FIG. 1 shows detailed sequence verification of pET41a-IDH1 and alignment against published IDH1 CDS below.

2. IDH1 Site Directed Mutagenesis to Create the IDH1-G97D Mutant

Site directed mutagenesis was performed to convert Gly97 residue to Asp of IDH1 protein using the following two primers; Primer 1: CAAATGTGGAAATCACCAAATGAC ACCATACGAAATATTCTGGG, Primer 2: CCCA-GAATATTTCGTATGGTGTCATTTGGT-GATTTCCACATTTG. (SEQ ID NO:12) A detailed method for site directed mutagenesis is described in the user manual for QuikChange® MultiSite-Directed Mutagenesis Kit (Stratagene, cat #200531). DNA sequencing confirmed that nucleotide G290 of GGC was mutated to GAC, creating residue 97Gly→Asp mutation in the IDH1 protein.

3. IDH1 Protein Expression and Purification

IDHwt, IDH1-G97D protein was expressed in the *E. coli* strain Rosetta and purified according to the detailed procedure below. Active IDH1 proteins are in dimer form, and SEC column fraction/peak that correspond to the dimer form were collected for enzymology analysis and cross comparison of catalytic activities of these proteins.

A. Cell Culturing:

Cells were grown in LB (20 µg/ml Kanamycin) at 37° C. with shaking until OD600 reaches 0.6. The temperature was changed to 18° C. and protein was induced by adding IPTG to final concentration of 1 mM. Cells were collected 12-16 hours after IPTG induction.

B. Buffer System:

Lysis buffer: 20 mM Tris, pH7.4, 0.1% Triton X-100, 500 mM NaCl, 1 mM PMSF, 5 mM β-mercaptoethanol, 10% glycerol.

Ni-Column Buffer A: 20 mM Tris, pH7.4, 500 mM NaCl, 5 mM β-mercaptoethanol, 10% glycerol.

Ni-column Buffer B: 20 mM Tris, pH7.4, 500 mM NaCl, 5 mM β-mercaptoethanol, 500 mM Imidazole, 10% glycerol.

Gel filtration Buffer C: 200 mM NaCl, 50 mM Tris 7.5, 5 mM β-mercaptoethanol, 2 mM $MnSO_4$, 10% glycerol.

C. Protein Purification Procedure

1. Cell pellet were resuspended in the lysis buffer (1 gram cell/5-10 ml buffer).
2. Cells were broken by passing the cell through Microfludizer with at a pressure of 15,000 psi for 3 times.
3. Soluble protein was collected from supernatant after centrifugation at 20,000 g (Beckman Avanti J-26XP) for 30 min at 4° C.
4. 5-10 ml of Ni-column was equilibrated by Buffer A until the A280 value reached baseline. The supernatant was loaded onto a 5-ml Ni-Sepharose column (2 ml/min) The column was washed by 10-20 CV of washing buffer (90% buffer A+10% buffer B) until A280 reach the baseline (2 ml/min).
5. The protein was eluted by liner gradient of 10-100% buffer B (20 CV) with the flow rate of 2 ml/min and the sample fractions were collected as 2 ml/tube.
6. The samples were analyzed on SDS-PAGE gel.
7. The samples were collected and dialyzed against 200× Gel filtration buffer for 2 times (1 hour and >4 hours).
8. The samples were concentrated to 10 ml.
9. 200 ml of S-200 Gel-filtration column was equilibrated by buffer C until the A280 value reached baseline. The samples were loaded onto Gel filtration column (0.5 ml/min)
10. The column was washed by 10 CV of buffer C, collect fractions as 2-4 ml/tube.
11. The samples were analyzed on SDS-PAGE gel and protein concentration was determined.

Example 2

IDH1-G97D Oxidized NADPH in the Presence of Alpha-Ketoglutarate (AlphaKG)

Figure 4A:
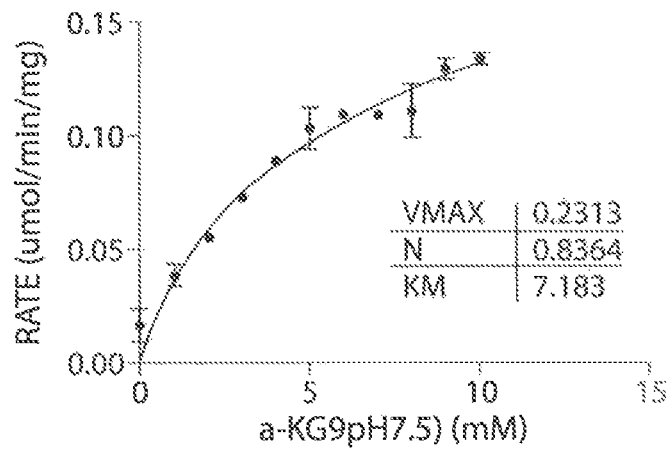
FIGS. 4A and 4B are graphs depicting Michaelis constants of alpha-ketoglutarate and NADPH for IDH1-G97D.
Figure 4B:
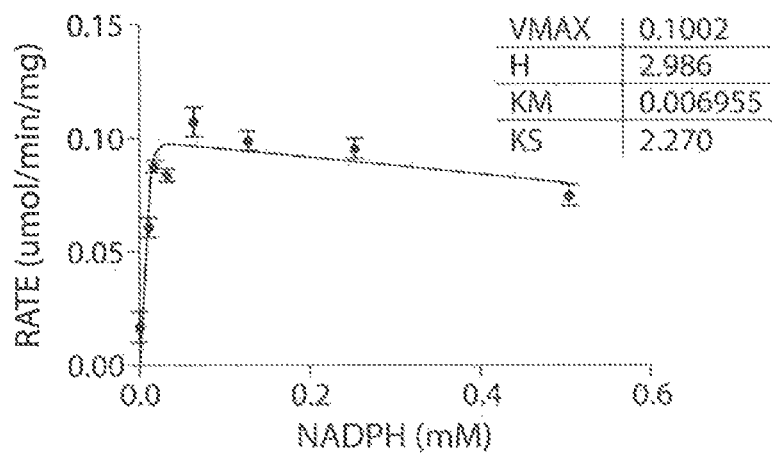

An isocitrate dehydrogenase 1 enzyme containing the mutation G97D (IDH1-G97D) was cloned, expressed, and purified as described above. Enzymatic reactions were set up and reaction progress was followed by spectrophotometric monitoring of the oxidation state of NADPH at 340 nM. The G97D mutant demonstrated the neoactivity of oxidizing NADPH in the presence of alpha-KG (FIG. 3). From this activity, the Michaelis constants of the reaction were determined (FIGS. 4A and 4B).

Methods:

To determine the catalytic efficiency of enzymes in the reduction of α-Ketoglutarate (α-KG), reactions were performed to determine Vmax and Km for α-KG. In these reactions, substrate was varied while the cofactor was held constant at 500 uM. All reactions were performed in 50 mM potassium phosphate buffer, pH 6.5, 10% glycerol, 0.03% (w/v) BSA, 5 mM $MgCl_2$, and 40 mM sodium hydrocarbonate. Reaction progress was followed by spectroscopy at 340 nM monitoring the change in oxidation state of the cofactor. Reaction was performed in a SFN-400 Stop Flow Spectraphotometer using enzyme sufficient for 3 sec reaction.

Example 3

Figure 5A:
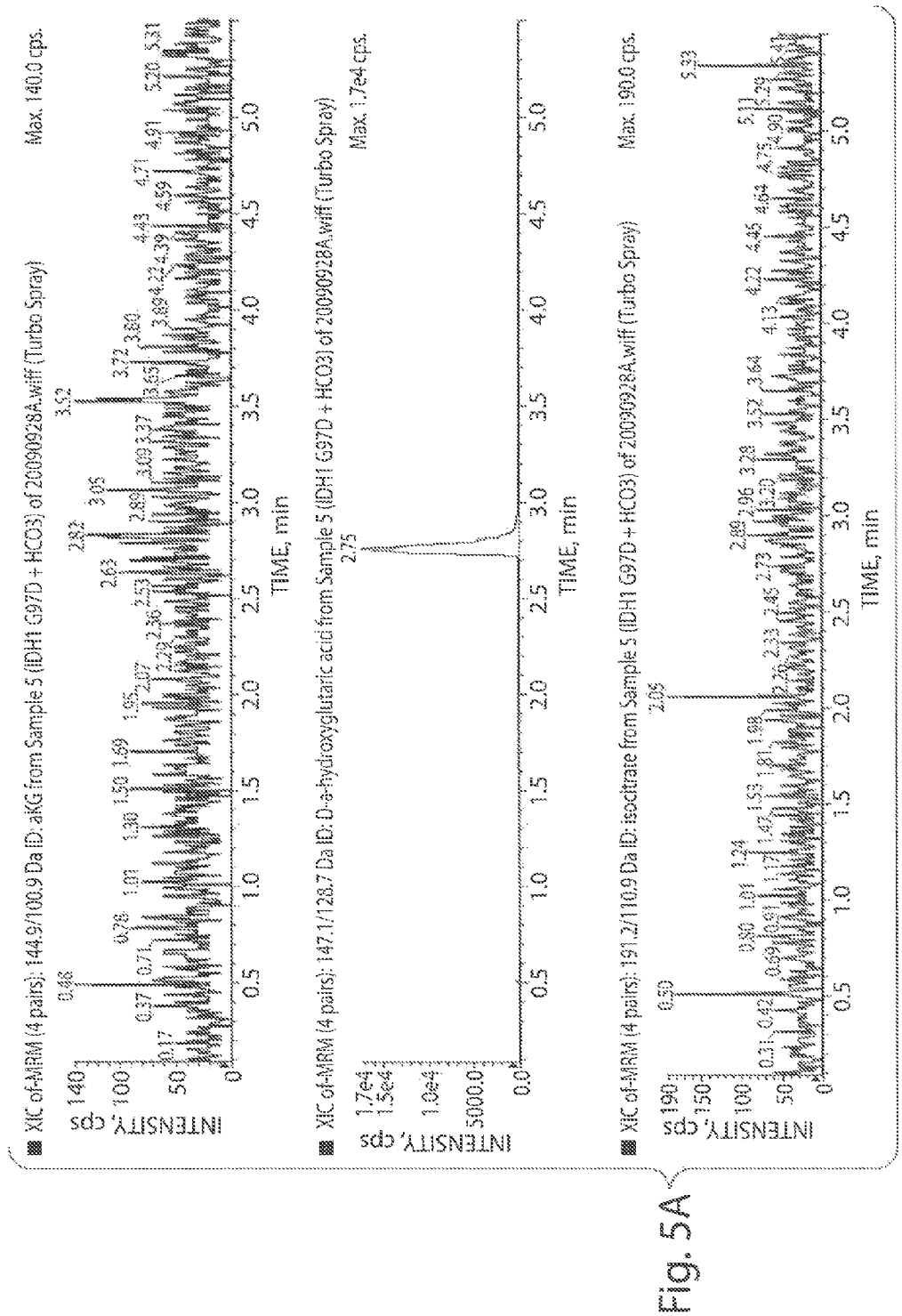
FIGS. 5A and 5B are results of LC-MS/MS analysis, which indicate that IDH1-G97D reduced alpha-ketoglutarate to 2-hydroxyglutaric acid in the presence of carbonate and in the absence of carbonate. No isocitrate was produced by the mutant enzyme as determined by LC-MS/MS analysis.
Figure 5B:
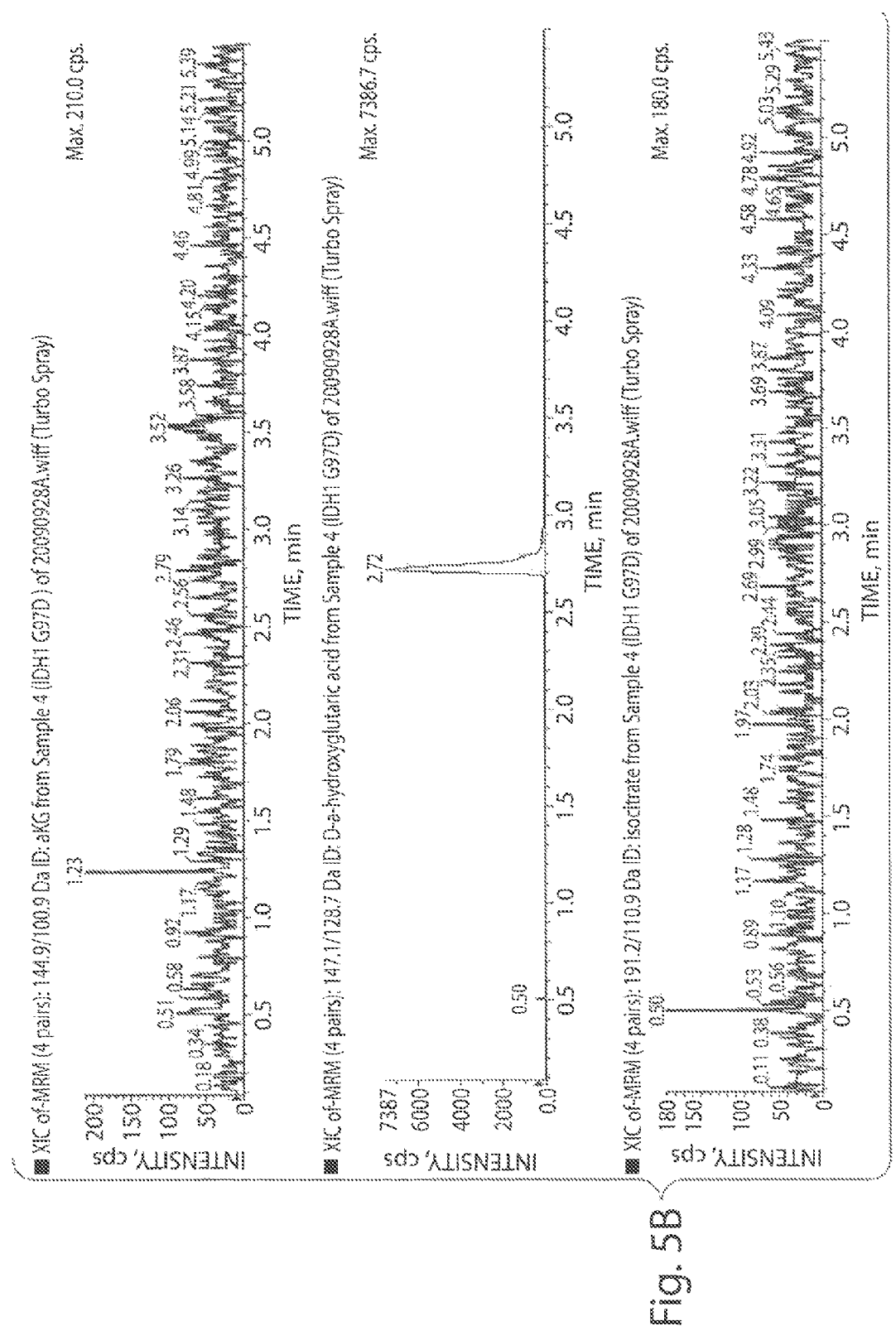

The Described IDH1-G97D Oxidation of NADPH in the Presence of AlphaKG Resulted in the Reduction of AlphaKG to 2-Hydroxyglutarate Enzymatic reactions with or without the addition of $NaHCO_3$ to supply a source of $CO_2$ were set up and run to completion as judged by a return to baseline of the $OD_{340}$. Reactions were extracted with acetonitrile, dried down, and re-suspended in Mobile Phase A before being subjected to LC-MS/MS (liquid chromatography-mass spectrometry/mass spectrometry) analysis using the described method. A single peak corresponding to the multiple reaction monitoring (MRM) transition and retention time of 2-hydroxyglutarate was observed (FIGS. 5A and 5B). The presence of 2-hydroxyglutarate was not dependent on $NaHCO_3$, and neither alphaKG nor isocitrate was detectable in either case.

Methods: Using standard experimental methods, an API2000 mass spectrometer was configured for optimal detection 2-hydroxyglutarate. The reaction products of the control and enzyme-containing reactions from above were investigated for the presence of 2-hydroxyglutarate. In the control reaction, no 2-hydroxyglutarate was detected, while in reaction containing G97D, 2-hydroxyglutarate was detected. This data confirms that one neoactivity of the G97D mutant is the reduction of α-KG to 2-hydroxyglutarate.

Example 4

Levels of 2-Hydroxyglutarate are Elevated in Cell Lines Carrying the G97D IDH-1 Mutation Cell Culture.

HCT-15 and DLD-1 cells have been previously reported to harbor the IDH1-G97D mutation while HCT116 cells do not have any mutations in IDH1 (Bleeker et al 2009, Hum. Mutat. 2009, January; 30(1) 7-11).

Metabolite Extraction.

Cells were grown in 10 cm tissue culture dishes, and the medium was replaced with identical fresh medium 1 h prior to metabolite extraction. One million cells were plated grown for two days prior to harvesting cell lysates for metabolite analysis. Metabolism was quenched and metabolites extracted by aspiration of media and immediate addition of 1.6 mL 80:20 methanol:water at −80° C., and transferred to a dry-ice bed to simultaneously lyse cells and quench metabolism. Cell remnants were scraped from the tissue culture dish and transferred, along with the methanol:water, into a 15 mL conical centrifuge tube. The resulting mixture was centrifuged at 14,000×g for 20 min, and the supernatant was moved to a new tube. A 50 µL portion of the extraction supernatant was combined with 50 µL of aqueous LC buffer (10 mM tributylamine, 10 mM Acetic Acid), spun at 13,000×g for 10 min to remove any remaining debris, and 10 µL injected into the LC for analysis by LC-MS, as described below.

Targeted Liquid Chromatography—Mass Spectrometry, 2-Hydroxyglutarate (2-HG) and TCA Metabolite Measurements.

Figure 6:
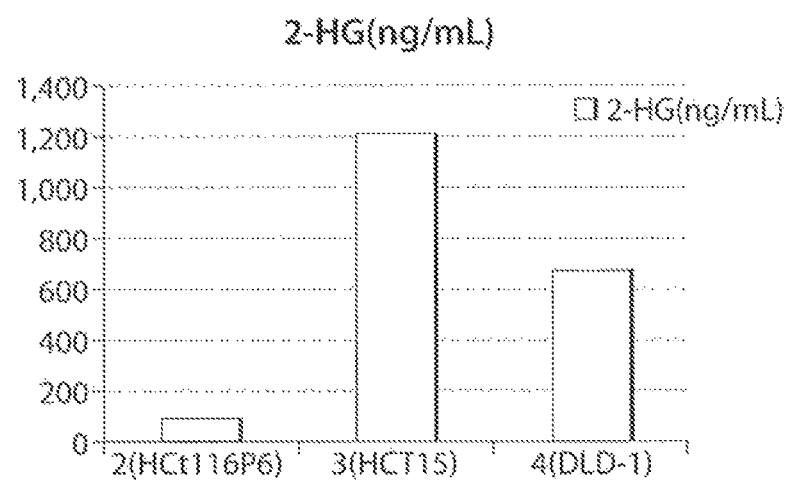
FIG. 6 is a bar graph depicting levels of 2-HG in HCT-15, HCT116, and DLD-1 cell lines.
Figure 7:
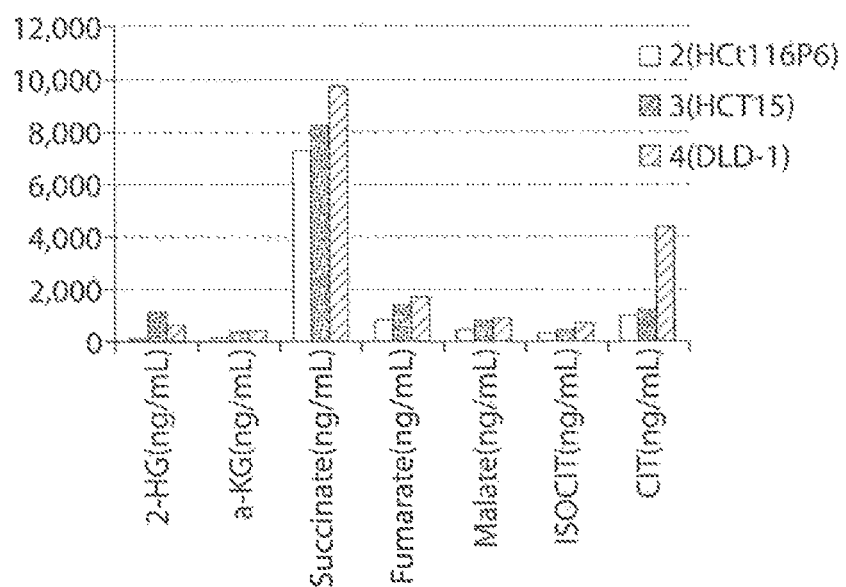
FIG. 7 is a bar graph depicting concentrations of TCA (tricarboxylic acid) metabolites (ng/mL) in cell lines HCT-15, DLD-1, and HCT116.

To measure whole-cell associated metabolites, media was aspirated and cells were harvested as described above. A liquid chromatography (LC) separation method was used to separate metabolites, coupled by negative electrospray ionization (ESI, −3.0 kV) to a triple-quadrupole mass spectrometer operating in multiple reaction monitoring (MRM) mode, with MS parameters optimized on infused metabolite standard solutions. Metabolites were separated by reversed phase chromatography using 10 mM tributyl-amine as an ion pairing agent in the aqueous mobile phase, according to a variant of a previously reported method (Luo et al., "Simultaneous determination of multiple intracellular metabolites in glycolysis, pentose phosphate pathway and tricarboxylic acid cycle by liquid chromatography-mass spectrometry" *J. Chromatogr* A 1147:153-64, 2007). The method allowed resolution of TCA metabolites: t=0, 50% B; t=5, 95% B; t=7, 95% B; t=8, 0% B, where B refers to an organic mobile phase of 100% methanol; the column was a Synergi Hydro-RP, 100 mm×2 mm, 2.1 µm particle size (Phenomonex). Metabolites were quantified by comparison of peak areas with pure metabolite standards at known concentration. Data and results are shown in Table 8 and FIGS. 6 and 7

Results.

Most notably, the cellular levels of 2-HG are significantly higher in cell lines carrying the G97D mutation of IDH-1. It too was notable that cell lines with elevated levels of 2-HG also showed elevated levels of alpha-ketoglutarate.

TABLE 8

| | Extracted TCA metabolite concentrations, reported in ng/mL. | | | | | | |
|---|---|---|---|---|---|---|---|
| | 2-HG (ng/mL) | a-KG (ng/mL) | Succinate (ng/mL) | Fumarate (ng/mL) | Malate (ng/mL) | ISOCIT (ng/mL) | CIT (ng/mL) |
| 2(HCt116 P6) | 94 | 231 | 7.297 | 926 | 615 | 384 | 1.071 |
| 3(HCT15) | 1.215 | 398 | 8.258 | 1.493 | 829 | 511 | 1.308 |
| 4(DLD-1) | 684 | 484 | 9.749 | 1.757 | 976 | 821 | 4.405 |

Example 5 siRNAs

IDH1

Exemplary siRNAs are presented in the following tables. Art-known methods can be used to select other siRNAs. siRNAs can be evaluated, e.g., by determining the ability of an siRNA to silence an IDH, e.g., IDH1, e.g., in an in vitro system, e.g., in cultured cells, e.g., HeLa cells or cultured glioma cells. siRNAs known in the art for silencing the target can also be used, see, e.g., *Silencing of cytosolic NADP+ dependent isocitrate dehydrogenase by small interfering RNA enhances the sensitivity of HeLa cells toward stauraropine*, Lee et al., 2009, Free Radical Research, 43: 165-173.

The siRNAs in Tables 1-7 represent candidates spanning the IDH1 mRNA at nucleotide positions 523, 524, and 525 according to the mRNA sequence presented at GenBank Accession No. NM_005896.2 (Record dated May 10, 2009; GI28178824) (SEQ ID NO:10, FIG. 2B); equivalent to nucleotide positions 289, 290, and 291 of the cDNA sequence presented at GenBank Accession No. NM_005896.2 (Record dated May 10, 2009; GI28178824) (SEQ ID NO:9, FIG. 2A).

The RNAs in the tables can be modified, e.g., as described herein. Modifications include chemical modifications to enhance properties, such as resistance to degradation, and the use of overhangs. For example, either one or both of the sense and antisense strands in the tables can include an additional dinucleotide (e.g., TT, UU, dTdT) at one or both ends, e.g., at the 3' end.

TABLE 1 siRNAs targeting wildtype IDH1

| Position on mRNA (FIG. 2B) | sense (5' to 3') | SEQ ID NO: | antisense (5' to 3') | SEQ ID NO: |
|---|---|---|---|---|
| 507 | GUGGAAAUCACCAAAUGGC | 13 | GCCAUUUGGUGAUUUCCAC | 24 |
| 508 | UGGAAAUCACCAAAUGGCA | 15 | UGCCAUUUGGUGAUUUCCA | 16 |
| 509 | GGAAAUCACCAAAUGGCAC | 17 | GUGCCAUUUGGUGAUUUCC | 18 |
| 510 | GAAAUCACCAAAUGGCACC | 19 | GGUGCCAUUUGGUGAUUUC | 20 |
| 511 | AAAUCACCAAAUGGCACCA | 21 | UGGUGCCAUUUGGUGAUUU | 22 |
| 512 | AAUCACCAAAUGGCACCAU | 23 | AUGGUGCCAUUUGGUGAUU | 24 |
| 513 | AUCACCAAAUGGCACCAUA | 25 | UAUGGUGCCAUUUGGUGAU | 26 |
| 514 | UCACCAAAUGGCACCAUAC | 27 | GUAUGGUGCCAUUUGGUGA | 28 |
| 515 | CACCAAAUGGCACCAUACG | 29 | CGUAUGGUGCCAUUUGGUG | 30 |
| 516 | ACCAAAUGGCACCAUACGA | 31 | UCGUAUGGUGCCAUUUGGU | 32 |
| 517 | CCAAAUGGCACCAUACGAA | 33 | UUCGUAUGGUGCCAUUUGG | 34 |
| 518 | CAAAUGGCACCAUACGAAA | 35 | UUUCGUAUGGUGCCAUUUG | 36 |
| 519 | AAAUGGCACCAUACGAAAU | 37 | AUUUCGUAUGGUGCCAUUU | 38 |
| 520 | AAUGGCACCAUACGAAAUA | 39 | UAUUUCGUAUGGUGCCAUU | 40 |
| 521 | AUGGCACCAUACGAAAUAU | 41 | AUAUUUCGUAUGGUGCCAU | 42 |
| 522 | UGGCACCAUACGAAAUAUU | 43 | AAUAUUUCGUAUGGUGCCA | 44 |
| 523 | GGCACCAUACGAAAUAUUC | 45 | GAAUAUUUCGUAUGGUGCC | 46 |

35

TABLE 2 siRNAs targeting G289A mutant IDH1 (equivalent to G523A of SEQ ID NO: 10, FIG. 2B)

| Position on mRNA (FIG. 2B) | sense (5' to 3') | SEQ ID NO: | antisense (5' to 3') | SEQ ID NO: |
|---|---|---|---|---|
| 507 | GUGGAAAUCACCAAAUAGC | 47 | GCUAUUUGGUGAUUUCCAC | 48 |
| 508 | UGGAAAUCACCAAAUAGCA | 49 | UGCUAUUUGGUGAUUUCCA | 50 |
| 509 | GGAAAUCACCAAAUAGCAC | 51 | GUGCUAUUUGGUGAUUUCC | 52 |
| 510 | GAAAUCACCAAAUAGCACC | 53 | GGUGCUAUUUGGUGAUUUC | 54 |
| 511 | AAAUCACCAAAUAGCACCA | 55 | UGGUGCUAUUUGGUGAUUU | 56 |
| 512 | AAUCACCAAAUAGCACCAU | 57 | AUGGUGCUAUUUGGUGAUU | 58 |
| 513 | AUCACCAAAUAGCACCAUA | 59 | UAUGGUGCUAUUUGGUGAU | 60 |
| 514 | UCACCAAAUAGCACCAUAC | 61 | GUAUGGUGCUAUUUGGUGA | 62 |
| 515 | CACCAAAUAGCACCAUACG | 63 | CGUAUGGUGCUAUUUGGUG | 64 |
| 516 | ACCAAAUAGCACCAUACGA | 65 | UCGUAUGGUGCUAUUUGGU | 66 |
| 517 | CCAAAUAGCACCAUACGAA | 67 | UUCGUAUGGUGCUAUUUGG | 68 |
| 518 | CAAAUAGCACCAUACGAAA | 69 | UUUCGUAUGGUGCUAUUUG | 70 |
| 519 | AAAUAGCACCAUACGAAAU | 71 | AUUUCGUAUGGUGCUAUUU | 72 |
| 520 | AAUAGCACCAUACGAAAUA | 73 | UAUUUCGUAUGGUGCUAUU | 74 |

TABLE 2-continued siRNAs targeting G289A mutant IDH1 (equivalent to G523A of SEQ ID NO: 10, FIG. 2B)

| Position on mRNA (FIG. 2B) | sense (5' to 3') | SEQ ID NO: | antisense (5' to 3') | SEQ ID NO: |
|---|---|---|---|---|
| 521 | AUAGCACCAUACGAAAUAU | 75 | AUAUUUCGUAUGGUGCUAU | 76 |
| 522 | UAGCACCAUACGAAAUAUU | 77 | AAUAUUUCGUAUGGUGCUA | 78 |
| 523 | AGCACCAUACGAAAUAUUC | 79 | GAAUAUUUCGUAUGGUGCU | 80 |

TABLE 3 siRNAs targeting G289C mutant IDH1 (equivalent to G523C of SEQ ID NO: 10, FIG. 2B)

| Position on mRNA (FIG. 2B) | sense (5' to 3') | SEQ ID NO: | antisense (5' to 3') | SEQ ID NO: |
|---|---|---|---|---|
| 507 | GUGGAAAUCACCAAAUCGC | 81 | GCGAUUUGGUGAUUUCCAC | 82 |
| 508 | UGGAAAUCACCAAAUCGCA | 83 | UGCGAUUUGGUGAUUUCCA | 84 |
| 509 | GGAAAUCACCAAAUCGCAC | 85 | GUGCGAUUUGGUGAUUUCC | 86 |
| 510 | GAAAUCACCAAAUCGCACC | 87 | GGUGCGAUUUGGUGAUUUC | 88 |
| 511 | AAAUCACCAAAUCGCACCA | 89 | UGGUGCGAUUUGGUGAUUU | 90 |
| 512 | AAUCACCAAAUCGCACCAU | 91 | AUGGUGCGAUUUGGUGAUU | 92 |
| 513 | AUCACCAAAUCGCACCAUA | 93 | UAUGGUGCGAUUUGGUGAU | 94 |
| 514 | UCACCAAAUCGCACCAUAC | 95 | GUAUGGUGCGAUUUGGUGA | 96 |
| 515 | CACCAAAUCGCACCAUACG | 97 | CGUAUGGUGCGAUUUGGUG | 98 |
| 516 | ACCAAAUCGCACCAUACGA | 99 | UCGUAUGGUGCGAUUUGGU | 100 |
| 517 | CCAAAUCGCACCAUACGAA | 101 | UUCGUAUGGUGCGAUUUGG | 102 |
| 518 | CAAAUCGCACCAUACGAAA | 103 | UUUCGUAUGGUGCGAUUUG | 104 |
| 519 | AAAUCGCACCAUACGAAAU | 105 | AUUUCGUAUGGUGCGAUUU | 106 |
| 520 | AAUCGCACCAUACGAAAUA | 107 | UAUUUCGUAUGGUGCGAUU | 108 |
| 521 | AUCGCACCAUACGAAAUAU | 109 | AUAUUUCGUAUGGUGCGAU | 110 |
| 522 | UCGCACCAUACGAAAUAUU | 111 | AAUAUUUCGUAUGGUGCGA | 112 |
| 523 | CGCACCAUACGAAAUAUUC | 113 | GAAUAUUUCGUAUGGUGCG | 114 |

TABLE 4 siRNAs targeting G289U mutant IDH1 (equivalent to G523U of SEQ ID NO: 10, FIG. 2B)

| Position on mRNA (FIG. 2B) | sense (5' to 3') | SEQ ID NO: | antisense (5' to 3') | SEQ ID NO: |
|---|---|---|---|---|
| 507 | GUGGAAAUCACCAAAUUGC | 115 | GCAAUUUGGUGAUUUCCAC | 116 |
| 508 | UGGAAAUCACCAAAUUGCA | 117 | UGCAAUUUGGUGAUUUCCA | 118 |
| 509 | GGAAAUCACCAAAUUGCAC | 119 | GUGCAAUUUGGUGAUUUCC | 120 |
| 510 | GAAAUCACCAAAUUGCACC | 121 | GGUGCAAUUUGGUGAUUUC | 122 |
| 511 | AAAUCACCAAAUUGCACCA | 123 | UGGUGCAAUUUGGUGAUUU | 124 |

TABLE 4-continued siRNAs targeting G289U mutant IDH1 (equivalent to G523U of SEQ ID NO: 10, FIG. 2B)

| Position on mRNA (FIG. 2B) | sense (5' to 3') | SEQ ID NO: | antisense (5' to 3') | SEQ ID NO: |
|---|---|---|---|---|
| 512 | AAUCACCAAAUUGCACCAU | 125 | AUGGUGCAAUUUGGUGAUU | 126 |
| 513 | AUCACCAAAUUGCACCAUA | 127 | UAUGGUGCAAUUUGGUGAU | 128 |
| 514 | UCACCAAAUUGCACCAUAC | 129 | GUAUGGUGCAAUUUGGUGA | 130 |
| 515 | CACCAAAUUGCACCAUACG | 131 | CGUAUGGUGCAAUUUGGUG | 132 |
| 516 | ACCAAAUUGCACCAUACGA | 133 | UCGUAUGGUGCAAUUUGGU | 134 |
| 517 | CCAAAUUGCACCAUACGAA | 135 | UUCGUAUGGUGCAAUUUGG | 136 |
| 518 | CAAAUUGCACCAUACGAAA | 137 | UUUCGUAUGGUGCAAUUUG | 138 |
| 519 | AAAUUGCACCAUACGAAAU | 139 | AUUUCGUAUGGUGCAAUUU | 140 |
| 520 | AAUUGCACCAUACGAAAUA | 141 | UAUUUCGUAUGGUGCAAUU | 142 |
| 521 | AUUGCACCAUACGAAAUAU | 143 | AUAUUUCGUAUGGUGCAAU | 144 |
| 522 | UUGCACCAUACGAAAUAUU | 145 | AAUAUUUCGUAUGGUGCAA | 146 |
| 523 | UGCACCAUACGAAAUAUUC | 147 | GAAUAUUUCGUAUGGUGCA | 148 |

TABLE 5 siRNAs targeting G290A mutant IDH1 (equivalent to G524A of SEQ ID NO: 10, FIG. 2B)

| Position on mRNA (FIG. 2B) | sense (5' to 3') | SEQ ID NO: | antisense (5' to 3') | SEQ ID NO: |
|---|---|---|---|---|
| 507 | GUGGAAAUCACCAAAUGAC | 149 | GUCAUUUGGUGAUUUCCAC | 150 |
| 508 | UGGAAAUCACCAAAUGACA | 151 | UGUCAUUUGGUGAUUUCCA | 152 |
| 509 | GGAAAUCACCAAAUGACAC | 153 | GUGUCAUUUGGUGAUUUCC | 154 |
| 510 | GAAAUCACCAAAUGACACC | 155 | GGUGUCAUUUGGUGAUUUC | 156 |
| 511 | AAAUCACCAAAUGACACCA | 157 | UGGUGUCAUUUGGUGAUUU | 158 |
| 512 | AAUCACCAAAUGACACCAU | 159 | AUGGUGUCAUUUGGUGAUU | 160 |
| 513 | AUCACCAAAUGACACCAUA | 161 | UAUGGUGUCAUUUGGUGAU | 162 |
| 514 | UCACCAAAUGACACCAUAC | 163 | GUAUGGUGUCAUUUGGUGA | 14 |
| 515 | CACCAAAUGACACCAUACG | 165 | CGUAUGGUGUCAUUUGGUG | 166 |
| 516 | ACCAAAUGACACCAUACGA | 167 | UCGUAUGGUGUCAUUUGGU | 168 |
| 517 | CCAAAUGACACCAUACGAA | 169 | UUCGUAUGGUGUCAUUUGG | 170 |
| 518 | CAAAUGACACCAUACGAAA | 171 | UUUCGUAUGGUGUCAUUUG | 172 |
| 519 | AAAUGACACCAUACGAAAU | 173 | AUUUCGUAUGGUGUCAUUU | 174 |
| 520 | AAUGACACCAUACGAAAUA | 175 | UAUUUCGUAUGGUGUCAUU | 176 |
| 521 | AUGACACCAUACGAAAUAU | 177 | AUAUUUCGUAUGGUGUCAU | 178 |
| 522 | UGACACCAUACGAAAUAUU | 179 | AAUAUUUCGUAUGGUGUCA | 180 |
| 523 | GACACCAUACGAAAUAUUC | 181 | GAAUAUUUCGUAUGGUGUC | 182 |

TABLE 6 siRNAs targeting G290C mutant IDH1 (equivalent to G524C of SEQ ID NO: 10, FIG. 2B)

| Position on mRNA (FIG. 2B) | sense (5' to 3') | SEQ ID NO: | antisense (5' to 3') | SEQ ID NO: |
|---|---|---|---|---|
| 507 | GUGGAAAUCACCAAAUGCC | 183 | GGCAUUUGGUGAUUUCCAC | 184 |
| 508 | UGGAAAUCACCAAAUGCCA | 185 | UGGCAUUUGGUGAUUUCCA | 186 |
| 509 | GGAAAUCACCAAAUGCCAC | 187 | GUGGCAUUUGGUGAUUUCC | 188 |
| 510 | GAAAUCACCAAAUGCCACC | 189 | GGUGGCAUUUGGUGAUUUC | 190 |
| 511 | AAAUCACCAAAUGCCACCA | 191 | UGGUGGCAUUUGGUGAUUU | 192 |
| 512 | AAUCACCAAAUGCCACCAU | 193 | AUGGUGGCAUUUGGUGAUU | 194 |
| 513 | AUCACCAAAUGCCACCAUA | 195 | UAUGGUGGCAUUUGGUGAU | 196 |
| 514 | UCACCAAAUGCCACCAUAC | 197 | GUAUGGUGGCAUUUGGUGA | 198 |
| 515 | CACCAAAUGCCACCAUACG | 199 | CGUAUGGUGGCAUUUGGUG | 200 |
| 516 | ACCAAAUGCCACCAUACGA | 201 | UCGUAUGGUGGCAUUUGGU | 201 |
| 517 | CCAAAUGCCACCAUACGAA | 203 | UUCGUAUGGUGGCAUUUGG | 202 |
| 518 | CAAAUGCCACCAUACGAAA | 205 | UUUCGUAUGGUGGCAUUUG | 204 |
| 519 | AAAUGCCACCAUACGAAAU | 207 | AUUUCGUAUGGUGGCAUUU | 206 |
| 520 | AAUGCCACCAUACGAAAUA | 209 | UAUUUCGUAUGGUGGCAUU | 208 |
| 521 | AUGCCACCAUACGAAAUAU | 211 | AUAUUUCGUAUGGUGGCAU | 210 |
| 522 | UGCCACCAUACGAAAUAUU | 213 | AAUAUUUCGUAUGGUGGCA | 212 |
| 523 | GCCACCAUACGAAAUAUUC | 215 | GAAUAUUUCGUAUGGUGGC | 214 |

TABLE 7 siRNAs targeting G290U mutant IDH1 (equivalent to G524U of SEQ ID NO: 10, FIG. 2B)

| Position on mRNA (FIG. 2B) | sense (5' to 3') | SEQ ID NO: | antisense (5' to 3') | SEQ ID NO: |
|---|---|---|---|---|
| 507 | GUGGAAAUCACCAAAUGUC | 215 | GACAUUUGGUGAUUUCCAC | 216 |
| 508 | UGGAAAUCACCAAAUGUCA | 217 | UGACAUUUGGUGAUUUCCA | 218 |
| 509 | GGAAAUCACCAAAUGUCAC | 219 | GUGACAUUUGGUGAUUUCC | 220 |
| 510 | GAAAUCACCAAAUGUCACC | 221 | GGUGACAUUUGGUGAUUUC | 222 |
| 511 | AAAUCACCAAAUGUCACCA | 223 | UGGUGACAUUUGGUGAUUU | 224 |
| 512 | AAUCACCAAAUGUCACCAU | 225 | AUGGUGACAUUUGGUGAUU | 226 |
| 513 | AUCACCAAAUGUCACCAUA | 227 | UAUGGUGACAUUUGGUGAU | 228 |
| 514 | UCACCAAAUGUCACCAUAC | 229 | GUAUGGUGACAUUUGGUGA | 230 |
| 515 | CACCAAAUGUCACCAUACG | 231 | CGUAUGGUGACAUUUGGUG | 232 |
| 516 | ACCAAAUGUCACCAUACGA | 233 | UCGUAUGGUGACAUUUGGU | 234 |
| 517 | CCAAAUGUCACCAUACGAA | 235 | UUCGUAUGGUGACAUUUGG | 236 |
| 518 | CAAAUGUCACCAUACGAAA | 237 | UUUCGUAUGGUGACAUUUG | 238 |
| 519 | AAAUGUCACCAUACGAAAU | 239 | AUUUCGUAUGGUGACAUUU | 240 |
| 520 | AAUGUCACCAUACGAAAUA | 241 | UAUUUCGUAUGGUGACAUU | 242 |

TABLE 7-continued siRNAs targeting G290U mutant IDH1 (equivalent to G524U of SEQ ID NO: 10, FIG. 2B)

| Position on mRNA (FIG. 2B) | sense (5' to 3') | SEQ ID NO: | antisense (5' to 3') | SEQ ID NO: |
|---|---|---|---|---|
| 521 | AUGUCACCAUACGAAAUAU | 243 | AUAUUUCGUAUGGUGACAU | 244 |
| 522 | UGUCACCAUACGAAAUAUU | 245 | AAUAUUUCGUAUGGUGACA | 246 |
| 523 | GUCACCAUACGAAAUAUUC | 247 | GAAUAUUUCGUAUGGUGAC | 248 |

Example 6

Materials and Methods

Summary

The G97D mutation was introduced into human IDH1 by standard molecular biology techniques. Cells were cultured in DMEM, 10% fetal bovine serum. Cells were transfected and selected using standard techniques. Protein expression levels were determined by Western blot analysis using IDHc antibody (Santa Cruz Biotechnology), IDH1 antibody (proteintech), MYC tag antibody (Cell Signaling Technology). Metabolites were extracted from cultured cells and from tissue samples according to close variants of a previously reported method (Lu, W., Kimball, E. & Rabinowitz, J. D. J Am Soc Mass Spectrom 17, 37-50 (2006)), using 80% aqueous methanol (−80° C.) and either tissue scraping or homogenization to disrupt cells. Enzymatic activity in cell lysates was assessed by following a change in NADPH fluorescence over time in the presence of isocitrate and NADP, or αKG and NADPH. For enzyme assays using recombinant IDH1 enzyme, proteins were produced in E. coli and purified using Ni affinity chromatography followed by Sephacryl S-200 size-exclusion chromatography. Enzymatic activity for recombinant IDH1 protein was assessed by following a change in NADPH UV absorbance at 340 nm using a stop-flow spectrophotometer in the presence of isocitrate and NADP or αKG and NADPHMetabolites were extracted and analyzed by LC-MS/MS as described above.

Supplementary Methods

Cloning, Expression, and Purification of IDH1 Wt and Mutants in E. coli.

The open reading frame (ORF) clone of human isocitrate dehydrogenase 1 (cDNA) (IDH1; ref. ID NM_005896) was purchased from Invitrogen in pENTR221 (Carlsbad, Calif.) and Origene Inc. in pCMV6 (Rockville, Md.). To transfect cells with wild-type or mutant IDH1, standard molecular biology mutagenesis techniques were utilized to alter the DNA of the ORF in pCMV6 to introduce base pair change which resulted in a change in the amino acid code at position 97 from G (wt) to D (mutant; or G97D), and confirmed by standard DNA sequencing methods. For expression in E. coli, the coding region was amplified from pENTR221 by PCR using primers designed to add NDEI and XHO1 restrictions sites at the 5' and 3' ends respectively. The resultant fragment was cloned into vector pET41a (EMD Biosciences, Madison, Wis.) to enable the E. coli expression of C-terminus His8-tagged protein. Site directed mutagenesis was performed on the pET41a-ICHD1 plasmid using the QuikChange® Multi-Site-Directed Mutagenesis Kit (Stratagene, La Jolla, Calif.).

Wild-type and mutant proteins were expressed in and purified from the E. coli Rosetta™ strain (Invitrogen, Carlsbad, Calif.) as follows. Cells were grown in LB (20 μg/ml Kanamycin) at 37° C. with shaking until OD600 reaches 0.6. The temperature was changed to 18° C. and protein expression was induced by adding IPTG to final concentration of 1 mM. After 12-16 hours of IPTG induction, cells were resuspended in Lysis Buffer (20 mM Tris, pH7.4, 0.1% Triton X-100, 500 mM NaCl, 1 mM PMSF, 5 mM β-mercaptoethanol, 10% glycerol) and disrupted by microfluidation. The 20,000 g supernatant was loaded on metal chelate affinity resin (MCAC) equilibrated with Nickel Column Buffer A (20 mM Tris, pH7.4, 500 mM NaCl, 5 mM β-mercaptoethanol, 10% glycerol) and washed for 20 column volumes. Elution from the column was effected by a 20 column-volume linear gradient of 10% to 100% Nickel Column Buffer B (20 mM Tris, pH7.4, 500 mM NaCl, 5 mM β-mercaptoethanol, 500 mM Imidazole, 10% glycerol) in Nickel Column Buffer A). Fractions containing the protein of interest were identified by SDS-PAGE, pooled, and dialyzed twice against a 200-volume excess of Gel Filtration Buffer (200 mM NaCl, 50 mM Tris 7.5, 5 mM β-mercaptoethanol, 2 mM $MnSO_4$, 10% glycerol), then concentrated to 10 ml using Centricon (Millipore, Billerica, Mass.) centrifugal concentrators. Purification of active dimers was achieved by applying the concentrated eluent from the MCAC column to a Sephacryl S-200 (GE Life Sciences, Piscataway, N.J.) column equilibrated with Gel Filtration Buffer and eluting the column with 20 column volumes of the same buffer. Fractions corresponding to the retention time of the dimeric protein were identified by SDS-PAGE and pooled for storage at −80° C.

Detection of Isocitrate, αKG, and 2HG in Purified Enzyme Reactions by LC-MS/MS.

Enzyme reactions performed as described in the text were run to completion as judged by measurement of the oxidation state of NADPH at 340 nm Reactions were extracted with eight volumes of methanol, and centrifuged to remove precipitated protein. The supernatant was dried under a stream of nitrogen and resuspended in $H_2O$. Analysis was conducted on an API2000 LC-MS/MS (Applied Biosystems, Foster City, Calif.). Sample separation and analysis was performed on a 150×2 mm, 4 uM Synergi Hydro-RP 80 A column, using a gradient of Buffer A (10 mM tributylamine, 15 mM acetic acid, 3% (v/v) methanol, in water) and Buffer B (methanol) using MRM transitions.

Recombinant IDH1 Enzyme Assays.

All reactions were performed in standard enzyme reaction buffer (150 mM NaCl, 20 mM Tris-Cl, pH 7.5, 10% glycerol, 5 mM $MgCl_2$ and 0.03% (w/v) bovine serum albumin) For determination of kinetic parameters, sufficient enzyme was added to give a linear reaction for 1 to 5 seconds. Reaction progress was monitored by observation of the reduction state of the cofactor at 340 nm in an SFM-400 stopped-flow spectrophotometer (BioLogic, Knoxyille, Tenn.). Enzymatic constants were determined using curve fitting algorithms to standard kinetic models with the Sigmaplot software package (Systat Software, San Jose, Calif.).

Example 8

Identification of Compounds with IDH1 G97D Inhibitory Activity

Assays were conducted in a standard 384-well plate in a reaction volume of 76 uL assay buffer (150 mM NaCl, 10 mM MgCl2, 20 mM Tris pH 7.5, 0.05% bovine serum albumin, 2 mM beta-mercaptoethanol) as follows: To 25 uL of substrate mix (4 uM NADPH, 1 mM aKG), 1 uL of test compound in DMSO was added. The plate was centrifuged briefly, and then 25 ul of enzyme mix was added (0.1 ug/mL ICDH1 G97D) followed by a brief centrifugation and shake at 100 RPM. The reaction was incubated for 50 minutes at room temperature, then 25 ul of detection mix (30 uM resazurin, 36 ug/ml diaphorase) was added, and the mixture further incubated for 5 minutes at room temperature. The activity readout as a result of the conversion of resazurin to resorufin was detected by fluorescent spectroscopy at excitation 544 nm and emission 590 nm (c/o 590 nm).

Four compounds were identified, which inhibited IDH1 G97D activity and are provided below:

| Compound | Activity (IC$_{50}$) |
|---|---|
| 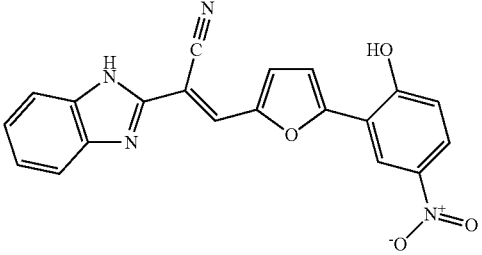 | A |
| 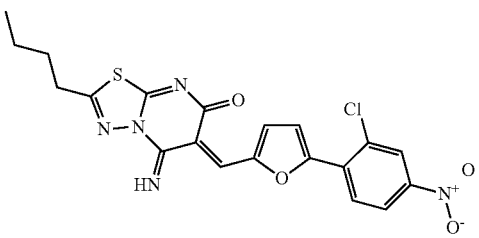 | A |
| 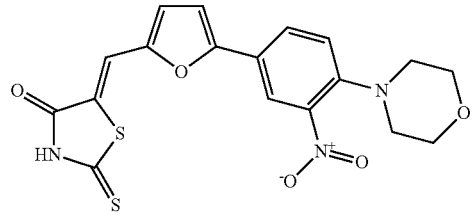 | A |
| (see above) | B |

*Indicates activity.
A indicates a compound having activity of from 1 to 5 μM.
B indicates a compound having activity of >5 to 10 μM.

---

The invention claimed is:

1. A method of diagnosing a subject having a cell proliferation-related disorder or suspected of having a cell proliferation-related disorder characterized by:
   (a) the presence, distribution, or level of an isocitrate dehydrogenase 1 enzyme having a mutation at residue 97 wherein the glycine residue has been replaced with an aspartic acid residue (IDH1-G97D), which has 2-hydroxyglutarate (2HG) neoactivity, wherein 2HG neoactivity is the ability to convert alpha ketoglutarate to 2-hydroxyglutarate, or
   (b) elevated levels of 2HG due to the presence of IDH1-G97D mutant enzyme having 2HG neoactivity,
   wherein said method comprises analyzing the presence, distribution, or level of 2HG in a tissue, product, or bodily fluid of said subject by a chromatographic method, wherein an increased presence, distribution, or level of 2HG indicates the presence of the cell proliferation-related disorder,
   thereby diagnosing the subject for the cell proliferation-related disorder.

2. A method of evaluating a subject for the susceptibility to a cell proliferation-related disorder characterized by:
   (a) the presence, distribution, or level of an isocitrate dehydrogenase 1 enzyme having a mutation at residue 97 wherein the glycine residue has been replaced with an aspartic acid residue (IDH1-G97D), which has 2-hydroxyglutarate (2HG) neoactivity, wherein 2HG neoactivity is the ability to convert alpha ketoglutarate to 2-hydroxyglutarate, or
   (b) elevated levels of 2HG due to the presence of IDH1-G97D mutant enzyme having 2HG neoactivity,
   wherein said method comprises analyzing the presence, distribution, or level of 2HG in a tissue, product, or bodily fluid of said subject by a chromatographic method,
   wherein an increased presence, distribution, or level of 2HG indicates the susceptibility of the subject to the cell proliferation-related disorder,
   thereby evaluating the subject for the susceptibility to the cell proliferation-related disorder.

3. The method of claim 1 or 2, wherein said cell proliferation-related disorder is selected from the group consisting of colon cancer and glioma.

4. The method of claim 1 or 2, wherein said bodily fluid is blood or plasma.

5. The method of claim 1 or 2, wherein the chromatographic method is LC-MS.

6. The method of claim 1 or 2, wherein the chromatographic method is GC-MS.

7. A method of evaluating a subject for the susceptibility to a cell proliferation-related disorder, said method comprising analyzing the subject or a sample from the subject for the presence, distribution, or level of 2-hydroxyglutarate (2HG), wherein the subject does not have or is not diagnosed as having 2-hydroxyglutaric aciduria, and wherein the subject has an isocitrate dehydrogenase 1 enzyme having a mutation at residue 97 wherein the glycine residue has been replaced with an aspartic acid residue (IDH1-G97D), and evaluating bodily fluid of the subject by a chromatographic method to identify 2HG, wherein an increased presence, distribution, or level of 2HG indicates the susceptibility of the subject to the cell proliferation-related disorder, thereby evaluating the subject for the susceptibility to the cell proliferation-related disorder.

8. A method of diagnosing a subject having a cell proliferation-related disorder or suspected of having a cell proliferation-related disorder, said method comprising analyzing the subject or a sample from the subject for the presence, distribution, or level of 2-hydroxyglutarate (2HG), wherein the subject is not having or not diagnosed as having 2-hydroxyglutaric aciduria, and wherein the subject has an isocitrate dehydrogenase 1 enzyme having a mutation at residue 97 wherein the glycine residue has been replaced with an aspartic acid residue (IDH1-G97D), and evaluating bodily fluid of the subject by a chromatographic method to identify 2HG, wherein an increased presence, distribution, or level of 2HG indicates the presence of the cell proliferation-related disorder in the subject, thereby diagnosing the subject for the cell proliferation-related disorder.

9. The method of claim 7 or 8, wherein said cell proliferation-related disorder is selected from the group consisting of colon cancer, glioma, prostate cancer, acute lymphoblastic leukemia, myelodysplasia, myelodysplastic syndrome, acute lymphoblastic leukemia and acute myelogenous leukemia.

10. The method of claim 7 or 8, wherein the bodily fluid of the subject is blood, plasma, or urine.

11. The method of claim 7 or 8, wherein the chromatographic method is LC-MS.

12. The method of claim 7 or 8, wherein the chromatographic method is GC-MS.

\* \* \* \* \*

SEQUENCE LISTING

<160> NUMBER OF SEQ ID NOS: 250

<210> SEQ ID NO 1
<211> LENGTH: 25
<212> TYPE: DNA
<213> ORGANISM: Artificial Sequence
<220> FEATURE:
<223> OTHER INFORMATION: Description of Artificial Sequence: Synthetic primer

<400> SEQUENCE: 1
taatcatatg tccaaaaaaa tcagt                                           25

<210> SEQ ID NO 2
<211> LENGTH: 33
<212> TYPE: DNA
<213> ORGANISM: Artificial Sequence
<220> FEATURE:
<223> OTHER INFORMATION: Description of Artificial Sequence: Synthetic primer

<400> SEQUENCE: 2

```
taatctcgag tgaaagtttg gcctgagcta gtt                                    33
```

<210> SEQ ID NO 3
<211> LENGTH: 8
<212> TYPE: PRT
<213> ORGANISM: Artificial Sequence
<220> FEATURE:
<223> OTHER INFORMATION: Description of Artificial Sequence: Synthetic
      8xHis tag

<400> SEQUENCE: 3

```
His His His His His His His His
1               5
```

<210> SEQ ID NO 4
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 4

```
Ser Leu Glu His His His His His His His His
1               5                   10
```

<210> SEQ ID NO 5
<211> LENGTH: 1245
<212> TYPE: DNA
<213> ORGANISM: Homo sapiens

<400> SEQUENCE: 5

```
atgtccaaaa aaatcagtgg cggttctgtg gtagagatgc aaggagatga aatgacacga      60
atcatttggg aattgattaa agagaaactc attttcccct acgtggaatt ggatctacat     120
agctatgatt taggcataga gaatcgtgat gccaccaacg accaagtcac caaggatgct     180
gcagaagcta taaagaagca taatgttggc gtcaaatgtg ccactatcac tcctgatgag     240
aagagggttg aggagttcaa gttgaaacaa atgtggaaat caccaaatgg caccatacga     300
aatattctgg gtggcacggt cttcagagaa gccattatct gcaaaaatat ccccggctt      360
gtgagtggat gggtaaaacc tatcatcata ggtcgtcatg cttatgggga tcaatacaga     420
gcaactgatt ttgttgttcc tgggcctgga aaagtagaga taacctacac accaagtgac     480
ggaacccaaa aggtgacata cctggtacat aactttgaag aaggtggtgg tgttgccatg     540
gggatgtata atcaagataa gtcaattgaa gattttgcac acagttcctt ccaaatggct     600
ctgtctaagg gttggcctt  gtatctgagc accaaaaaca ctattctgaa gaaatatgat     660
gggcgtttta aagacatctt tcaggagata tatgacaagc agtacaagtc ccagtttgaa     720
gctcaaaaga tctggtatga gcataggctc atcgacgaca tggtggccca agctatgaaa     780
tcagggggag gcttcatctg ggcctgtaaa aactatgatg gtgacgtgca gtcggactct     840
gtggcccaag gtatggctc  tctcggcatg atgaccagcg tgctggtttg tccagatggc     900
aagacagtag aagcagaggc tgcccacggg actgtaaccc gtcactaccg catgtaccag     960
aaaggacagg agacgtccac caatcccatt gcttccattt ttgcctggac cagagggtta    1020
gcccacagag caaagcttga taacaataaa gagcttgcct tctttgcaaa tgctttggaa    1080
gaagtctcta ttgagacaat tgaggctggc ttcatgacca aggacttggc tgcttgcatt    1140
aaaggtttac ccaatgtgca acgttctgac tacttgaata catttgagtt catggataaa    1200
cttggagaaa acttgaagat caaactagct caggccaaac tttaa                    1245
```

<210> SEQ ID NO 6
<211> LENGTH: 1297
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 6

```
atgtccaaaa aaatcagtgg cggttctgtg gtagagatgc aaggagatga atgacacga      60 atcatttggg aattgattaa agagaaactc attttccct acgtggaatt ggatctacat     120
agctatgatt taggcataga gaatcgtgat gccaccaacg accaagtcac caaggatgct    180
gcagaagcta taaagaagca taatgttggc gtcaaatgtg ccactatcac tcctgatgag    240
aagagggttg aggagttcaa gttgaaacaa atgtggaaat caccaaatgg caccatacga    300
aatattctgg gtggcacggt cttcagagaa gccattatct gcaaaaatat ccccggctt     360 gtgagtggat gggtaaaacc tatcatcata ggtcgtcatg cttatgggga tcaatacaga    420
gcaactgatt ttgttgttcc tgggcctgga aaagtagaga taacctacac accaagtgac    480
ggaacccaaa aggtgacata cctggtacat aactttgaag aaggtggtgg tgttgccatg    540
gggatgtata atcaagataa gtcaattgaa gattttgcac acagttcctt ccaaatggct    600
ctgtctaagg gttggccttt gtatctgagc accaaaaaca ctattctgaa gaaatatgat    660
gggcgtttta aagacatctt tcaggagata tatgacaagc agtacaagtc ccagtttgaa    720
gctcaaaaga tctggtatga gcataggctc atcgacgaca tggtggccca agctatgaaa    780
tcagagggag gcttcatctg ggcctgtaaa aactatgatg gtgacgtgca gtcggactct    840
gtggcccaag gtatggctc tctcggcatg atgaccagcg tgctggtttg tccagatggc    900
aagacagtag aagcagaggc tgcccacggg actgtaaccc gtcactaccg catgtaccag    960
aaaggacagg agacgtccac caatcccatt gcttccattt ttgcctggac cagagggtta   1020
gcccacagag caaagcttga taacaataaa gagcttgcct tctttgcaaa tgctttggaa   1080
gaagtctcta ttgagacaat tgaggctggc ttcatgacca aggacttggc tgcttgcatt   1140
aaaggtttac ccaatgtgca acgttctgac tacttgaata catttgagtt catggataaa   1200
cttggagaaa acttgaagat caaactagct caggccaaac tttcactcga gcaccaccac   1260
caccaccacc accactaatt gattaatacc taggctg                             1297
```

<210> SEQ ID NO 7
<211> LENGTH: 1245
<212> TYPE: DNA
<213> ORGANISM: Artificial Sequence
<220> FEATURE:
<223> OTHER INFORMATION: Description of Artificial Sequence: Synthetic
      consensus polynucleotide

<400> SEQUENCE: 7

```
atgtccaaaa aaatcagtgg cggttctgtg gtagagatgc aaggagatga atgacacga      60 atcatttggg aattgattaa agagaaactc attttccct acgtggaatt ggatctacat     120
agctatgatt taggcataga gaatcgtgat gccaccaacg accaagtcac caaggatgct    180
gcagaagcta taaagaagca taatgttggc gtcaaatgtg ccactatcac tcctgatgag    240
aagagggttg aggagttcaa gttgaaacaa atgtggaaat caccaaatgg caccatacga    300
aatattctgg gtggcacggt cttcagagaa gccattatct gcaaaaatat ccccggctt     360
```

```
gtgagtggat gggtaaaacc tatcatcata ggtcgtcatg cttatgggga tcaatacaga    420
gcaactgatt tgttgttcc tgggcctgga aaagtagaga taacctacac accaagtgac     480
ggaacccaaa aggtgacata cctggtacat aactttgaag aaggtggtgg tgttgccatg    540
gggatgtata atcaagataa gtcaattgaa gattttgcac acagttcctt ccaaatggct    600
ctgtctaagg gttggccttt gtatctgagc accaaaaaca ctattctgaa gaaatatgat    660
gggcgtttta agacatcttt tcaggagata tatgacaagc agtacaagtc ccagtttgaa    720
gctcaaaaga tctggtatga gcataggctc atcgacgaca tggtggccca agctatgaaa    780
tcagagggag gcttcatctg ggcctgtaaa aactatgatg gtgacgtgca gtcggactct    840
gtggcccaag ggtatggctc tctcggcatg atgaccagcg tgctggtttg tccagatggc    900
aagacagtag aagcagaggc tgcccacggg actgtaaccc gtcactaccg catgtaccag    960
aaaggacagg agacgtccac caatcccatt gcttccattt ttgcctggac cagagggtta   1020
gcccacagag caaagcttga taacaataaa gagcttgcct tctttgcaaa tgctttggaa   1080
gaagtctcta ttgagacaat tgaggctggc ttcatgacca aggacttggc tgcttgcatt   1140
aaaggtttac ccaatgtgca acgttctgac tacttgaata catttgagtt catggataaa   1200
cttggagaaa acttgaagat caaactagct caggccaaac tttma               1245

<210> SEQ ID NO 8
<211> LENGTH: 414
<212> TYPE: PRT
<213> ORGANISM: Homo sapiens

<400> SEQUENCE: 8

Met Ser Lys Lys Ile Ser Gly Gly Ser Val Val Glu Met Gln Gly Asp
 1               5                  10                  15

Glu Met Thr Arg Ile Ile Trp Glu Leu Ile Lys Glu Lys Leu Ile Phe
            20                  25                  30

Pro Tyr Val Glu Leu Asp Leu His Ser Tyr Asp Leu Gly Ile Glu Asn
        35                  40                  45

Arg Asp Ala Thr Asn Asp Gln Val Thr Lys Asp Ala Ala Glu Ala Ile
    50                  55                  60

Lys Lys His Asn Val Gly Val Lys Cys Ala Thr Ile Thr Pro Asp Glu
65                  70                  75                  80

Lys Arg Val Glu Glu Phe Lys Leu Lys Gln Met Trp Lys Ser Pro Asn
                85                  90                  95

Gly Thr Ile Arg Asn Ile Leu Gly Gly Thr Val Phe Arg Glu Ala Ile
            100                 105                 110

Ile Cys Lys Asn Ile Pro Arg Leu Val Ser Gly Trp Val Lys Pro Ile
        115                 120                 125

Ile Ile Gly Arg His Ala Tyr Gly Asp Gln Tyr Arg Ala Thr Asp Phe
    130                 135                 140

Val Val Pro Gly Pro Gly Lys Val Glu Ile Thr Tyr Thr Pro Ser Asp
145                 150                 155                 160

Gly Thr Gln Lys Val Thr Tyr Leu Val His Asn Phe Glu Glu Gly Gly
                165                 170                 175

Gly Val Ala Met Gly Met Tyr Asn Gln Asp Lys Ser Ile Glu Asp Phe
            180                 185                 190

Ala His Ser Ser Phe Gln Met Ala Leu Ser Lys Gly Trp Pro Leu Tyr
        195                 200                 205

Leu Ser Thr Lys Asn Thr Ile Leu Lys Lys Tyr Asp Gly Arg Phe Lys
    210                 215                 220
```

```
Asp Ile Phe Gln Glu Ile Tyr Asp Lys Gln Tyr Lys Ser Gln Phe Glu
225                 230                 235                 240

Ala Gln Lys Ile Trp Tyr Glu His Arg Leu Ile Asp Asp Met Val Ala
            245                 250                 255

Gln Ala Met Lys Ser Glu Gly Gly Phe Ile Trp Ala Cys Lys Asn Tyr
        260                 265                 270

Asp Gly Asp Val Gln Ser Asp Ser Val Ala Gln Gly Tyr Gly Ser Leu
    275                 280                 285

Gly Met Met Thr Ser Val Leu Val Cys Pro Asp Gly Lys Thr Val Glu
290                 295                 300

Ala Glu Ala Ala His Gly Thr Val Thr Arg His Tyr Arg Met Tyr Gln
305                 310                 315                 320

Lys Gly Gln Glu Thr Ser Thr Asn Pro Ile Ala Ser Ile Phe Ala Trp
            325                 330                 335

Thr Arg Gly Leu Ala His Arg Ala Lys Leu Asp Asn Asn Lys Glu Leu
        340                 345                 350

Ala Phe Phe Ala Asn Ala Leu Glu Glu Val Ser Ile Glu Thr Ile Glu
    355                 360                 365

Ala Gly Phe Met Thr Lys Asp Leu Ala Ala Cys Ile Lys Gly Leu Pro
370                 375                 380

Asn Val Gln Arg Ser Asp Tyr Leu Asn Thr Phe Glu Phe Met Asp Lys
385                 390                 395                 400

Leu Gly Glu Asn Leu Lys Ile Lys Leu Ala Gln Ala Lys Leu
            405                 410

<210> SEQ ID NO 9
<211> LENGTH: 1245
<212> TYPE: DNA
<213> ORGANISM: Homo sapiens

<400> SEQUENCE: 9
atgtccaaaa aaatcagtgg cggttctgtg gtagagatgc aaggagatga atgacacga      60 atcatttggg aattgattaa agagaaactc attttccct acgtggaatt ggatctacat     120
agctatgatt taggcataga gaatcgtgat gccaccaacg accaagtcac caaggatgct     180
gcagaagcta taaagaagca taatgttggc gtcaaatgtg ccactatcac tcctgatgag     240
aagagggttg aggagttcaa gttgaaacaa atgtggaaat caccaaatgg caccatacga     300
aatattctgg gtggcacggt cttcagagaa gccattatct gcaaaaatat ccccggcttt     360
gtgagtggat gggtaaaacc tatcatcata ggtcgtcatg cttatgggga tcaatacaga     420
gcaactgatt tgttgttcc tgggcctgga aaagtagaga taacctacac accaagtgac     480
ggaacccaaa aggtgacata cctggtacat aactttgaag aaggtggtgg tgttgccatg     540
gggatgtata atcaagataa gtcaattgaa gattttgcac acagttcctt ccaaatggct     600
ctgtctaagg ttggcccttt gtatctgagc accaaaaaca ctattctgaa gaaatatgat     660
gggcgtttta agacatctt tcaggagata tatgacaagc agtacaagtc ccagtttgaa     720
gctcaaaaga tctggtatga gcataggctc atcgacgaca tggtggccca agctatgaaa     780
tcagagggag gcttcatctg ggcctgtaaa aactatgatg gtgacgtgca gtcggactct     840
gtggcccaag gtatggctc tcggcatg atgaccagcg tgctggtttg tccagatggc     900
aagacagtag aagcagaggc tgcccacggg actgtaaccc gtcactaccg catgtaccag     960
aaaggacagg agacgtccac caatcccatt gcttccattt ttgcctggac cagagggtta    1020
```

-continued

```
gcccacagag caaagcttga taacaataaa gagcttgcct tctttgcaaa tgctttggaa    1080
gaagtctcta ttgagacaat tgaggctggc ttcatgacca aggacttggc tgcttgcatt    1140
aaaggtttac ccaatgtgca acgttctgac tacttgaata catttgagtt catggataaa    1200
cttggagaaa acttgaagat caaactagct caggccaaac tttaa                    1245
```

<210> SEQ ID NO 10
<211> LENGTH: 2339
<212> TYPE: DNA
<213> ORGANISM: Homo sapiens

<400> SEQUENCE: 10

```
cctgtggtcc cgggtttctg cagagtctac ttcagaagcg gaggcactgg gagtccggtt      60
tgggattgcc aggctgtggt tgtgagtctg agcttgtgag cggctgtggc gccccaactc     120
ttcgccagca tatcatcccg gcaggcgata aactacattc agttgagtct gcaagactgg     180
gaggaactgg ggtgataaga aatctattca ctgtcaaggt ttattgaagt caaaatgtcc     240
aaaaaaatca gtggcggttc tgtggtagag atgcaaggag atgaaatgac acgaatcatt     300
tgggaattga ttaaagagaa actcattttt ccctacgtgg aattggatct acatagctat     360
gatttaggca tagagaatcg tgatgccacc aacgaccaag tcaccaagga tgctgcagaa     420
gctataaaga agcataatgt tggcgtcaaa tgtgccacta tcactcctga tgagaagagg     480
gttgaggagt tcaagttgaa acaaatgtgg aaatcaccaa atggcaccat acgaaatatt     540
ctgggtggca cggtcttcag agaagccatt atctgcaaaa atatccccg gcttgtgagt     600 ggatgggtaa aacctatcat cataggtcgt catgcttatg gggatcaata cagagcaact     660
gattttgttg ttcctgggcc tggaaaagta gagataacct acacaccaag tgacggaacc     720
caaaaggtga catacctggt acataacttt gaagaaggtg gtggtgttgc catggggatg     780
tataatcaag ataagtcaat tgaagatttt gcacacagtt ccttccaaat ggctctgtct     840
aagggttggc ctttgtatct gagcaccaaa aacactattc tgaagaaata tgatgggcgt     900
tttaaagaca tctttcagga gatatatgac aagcagtaca agtcccagtt tgaagctcaa     960
aagatctggt atgagcatag gctcatcgac gacatggtgg cccaagctat gaaatcagag    1020
ggaggcttca tctgggcctg taaaaactat gatggtgacg tgcagtcgga ctctgtggcc    1080
caagggtatg gctctctcgg catgatgacc agcgtgctgg tttgtccaga tggcaagaca    1140
gtagaagcag aggctgccca cgggactgta acccgtcact accgcatgta ccagaaagga    1200
caggagacgt ccaccaatcc cattgcttcc attttgcct ggaccagagg gttagcccac    1260
agagcaaagc ttgataacaa taagagctt gccttctttg caaatgcttt ggaagaagtc    1320
tctattgaga caattgaggc tggcttcatg accaaggact tggctgcttg cattaaaggt    1380
ttacccaatg tgcaacgttc tgactacttg aatacatttg agttcatgga taaacttgga    1440
gaaaacttga agatcaaact agctcaggcc aaactttaag ttcatacctg agctaagaag    1500
gataattgtc ttttggtaac taggtctaca ggtttacatt tttctgtgtt acactcaagg    1560
ataaaggcaa atcaatttt gtaatttgtt tagaagccag agtttatctt ttctataagt    1620
ttacagcctt tttcttatat atacagttat tgccacctt gtgaacatgg caagggactt    1680
ttttacaatt tttattttat tttctagtac cagcctagga attcggttag tactcatttg    1740
tattcactgt cacttttct catgttctaa ttataaatga ccaaaatcaa gattgctcaa    1800
aagggtaaat gatagccaca gtattgctcc ctaaaatatg cataaagtag aaattcactg    1860
ccttcccctc ctgtccatga ccttgggcac agggaagttc tggtgtcata gatatcccgt    1920
```

```
tttgtgaggt agagctgtgc attaaacttg cacatgactg gaacgaagta tgagtgcaac    1980
tcaaatgtgt tgaagatact gcagtcattt ttgtaaagac cttgctgaat gtttccaata    2040
gactaaatac tgtttaggcc gcaggagagt ttggaatccg gaataaatac tacctggagg    2100
tttgtcctct ccattttct ctttctcctc ctggcctggc ctgaatatta tactactcta    2160
aatagcatat ttcatccaag tgcaataatg taagctgaat cttttttgga cttctgctgg    2220
cctgttttat ttcttttata taaatgtgat ttctcagaaa ttgatattaa acactatctt    2280
atcttctcct gaactgttga ttttaattaa aattaagtgc taattaccaa aaaaaaaa      2339

<210> SEQ ID NO 11
<211> LENGTH: 44
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 11
caaatgtgga aatcaccaaa tgacaccata cgaaatattc tggg                     44

<210> SEQ ID NO 12
<211> LENGTH: 44
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 12
cccagaatat ttcgtatggt gtcatttggt gatttccaca tttg                     44

<210> SEQ ID NO 13
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 13
guggaaauca ccaaauggc                                                 19

<210> SEQ ID NO 14
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 14
gccauuuggu gauuuccac                                                 19

<210> SEQ ID NO 15
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 15
uggaaaucac caaauggca                                                 19
```

<210> SEQ ID NO 16
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 16
ugccauuugg ugauuucca                                                    19

<210> SEQ ID NO 17
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 17
ggaaaucacc aaauggcac                                                    19

<210> SEQ ID NO 18
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 18
gugccauuug gugauuucc                                                    19

<210> SEQ ID NO 19
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 19
gaaaucacca aauggcacc                                                    19

<210> SEQ ID NO 20
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 20
ggugccauuu ggugauuuc                                                    19

<210> SEQ ID NO 21
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 21
aaaucaccaa auggcacca                                                    19

```
<210> SEQ ID NO 22
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 22
uggugccauu uggugauuu                                                    19

<210> SEQ ID NO 23
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 23
aaucaccaaa uggcaccau                                                    19

<210> SEQ ID NO 24
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 24
auggugccau uuggugauu                                                    19

<210> SEQ ID NO 25
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 25
aucaccaaau ggcaccaua                                                    19

<210> SEQ ID NO 26
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 26
uauggugcca uuuggugau                                                    19

<210> SEQ ID NO 27
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 27
ucaccaaaug gcaccauac                                                    19
```

-continued

```
<210> SEQ ID NO 28
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 28
guauggugcc auuugguga                                                       19

<210> SEQ ID NO 29
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 29
caccaaaugg caccauacg                                                       19

<210> SEQ ID NO 30
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 30
cguauggugc cauuuggug                                                       19

<210> SEQ ID NO 31
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 31
accaaauggc accauacga                                                       19

<210> SEQ ID NO 32
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 32
ucguauggug ccauuuggu                                                       19

<210> SEQ ID NO 33
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 33
ccaaauggca ccauacgaa                                                       19

<210> SEQ ID NO 34
```

```
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 34
uucguauggu gccauuugg                                                  19

<210> SEQ ID NO 35
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 35
caaauggcac cauacgaaa                                                  19

<210> SEQ ID NO 36
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 36
uuucguaugg ugccauuug                                                  19

<210> SEQ ID NO 37
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 37
aaauggcacc auacgaaau                                                  19

<210> SEQ ID NO 38
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 38
auuucguaug gugccauuu                                                  19

<210> SEQ ID NO 39
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 39
aauggcacca uacgaaaua                                                  19

<210> SEQ ID NO 40
<211> LENGTH: 19
```

```
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 40
uauuucguau ggugccauu                                                    19

<210> SEQ ID NO 41
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 41
auggcaccau acgaaauau                                                    19

<210> SEQ ID NO 42
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 42
auauuucgua uggugccau                                                    19

<210> SEQ ID NO 43
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 43
uggcaccaua cgaaauauu                                                    19

<210> SEQ ID NO 44
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 44
aauauuucgu auggugcca                                                    19

<210> SEQ ID NO 45
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 45
ggcaccauac gaaauauuc                                                    19

<210> SEQ ID NO 46
<211> LENGTH: 19
<212> TYPE: RNA
```

-continued

<213> ORGANISM: Artificial Sequence
<220> FEATURE:
<223> OTHER INFORMATION: Description of Artificial Sequence: Synthetic
      oligonucleotide

<400> SEQUENCE: 46
gaauauuucg uauggugcc                                                19

<210> SEQ ID NO 47
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 47
guggaaauca ccaaauagc                                                19

<210> SEQ ID NO 48
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 48
gcuauuuggu gauuccac                                                 19

<210> SEQ ID NO 49
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 49 uggaaucac caaauagca                                                 19

<210> SEQ ID NO 50
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 50
ugcuauuugg ugauuucca                                                19

<210> SEQ ID NO 51
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 51 ggaaucacc aaauagcac                                                 19

<210> SEQ ID NO 52
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 52
gugcuauuug gugauuucc                                                19

<210> SEQ ID NO 53
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 53
gaaaucacca aauagcacc                                                19

<210> SEQ ID NO 54
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 54
ggugcuauuu ggugauuuc                                                19

<210> SEQ ID NO 55
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 55
aaaucaccaa auagcacca                                                19

<210> SEQ ID NO 56
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 56
uggugcuauu uggugauuu                                                19

<210> SEQ ID NO 57
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 57
aaucaccaaa uagccaccau                                               19

<210> SEQ ID NO 58
<211> LENGTH: 19
<212> TYPE: RNA
<213> ORGANISM: Artificial Sequence
<220> FEATURE:

```
<223> OTHER INFORMATION: Description of Artificial Sequence: Synthetic
      oligonucleotide

<400> SEQUENCE: 58
auggugcuau uuggugauu                                                    19

<210> SEQ ID NO 59
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 59
aucaccaaau agcaccaua                                                    19

<210> SEQ ID NO 60
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 60
uauggugcua uuuggugau                                                    19

<210> SEQ ID NO 61
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 61
ucaccaaaua gcaccauac                                                    19

<210> SEQ ID NO 62
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 62
guauggugcu auuugguga                                                    19

<210> SEQ ID NO 63
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 63
caccaaauag caccauacg                                                    19

<210> SEQ ID NO 64
<211> LENGTH: 19
<212> TYPE: RNA
<213> ORGANISM: Artificial Sequence
<220> FEATURE:
<223> OTHER INFORMATION: Description of Artificial Sequence: Synthetic
```

```
oligonucleotide

<400> SEQUENCE: 64
cguauggugc uauuuggug                                                  19

<210> SEQ ID NO 65
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 65
accaaauagc accauacga                                                  19

<210> SEQ ID NO 66
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 66
ucguauggug cuauuuggu                                                  19

<210> SEQ ID NO 67
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 67
ccaaauagca ccauacgaa                                                  19

<210> SEQ ID NO 68
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 68
uucguauggu gcuauuugg                                                  19

<210> SEQ ID NO 69
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 69
caaauagcac cauacgaaa                                                  19

<210> SEQ ID NO 70
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide
```

```
<400> SEQUENCE: 70
uuucguaugg ugcuauuug                                                    19

<210> SEQ ID NO 71
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 71
aaauagcacc auacgaaau                                                    19

<210> SEQ ID NO 72
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 72
auuucguaug gugcuauuu                                                    19

<210> SEQ ID NO 73
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 73
aauagcacca uacgaaaua                                                    19

<210> SEQ ID NO 74
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 74
uauuucguau ggugcuauu                                                    19

<210> SEQ ID NO 75
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 75
auagcaccau acgaaauau                                                    19

<210> SEQ ID NO 76
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide
```

-continued

<400> SEQUENCE: 76
auauuucgua uggugcuau                                          19

<210> SEQ ID NO 77
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 77
uagcaccaua cgaaauauu                                          19

<210> SEQ ID NO 78
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 78
aauauuucgu auggugcua                                          19

<210> SEQ ID NO 79
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 79
agcaccauac gaaauauuc                                          19

<210> SEQ ID NO 80
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 80
gaauauuucg uauggugcu                                          19

<210> SEQ ID NO 81
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 81
guggaaauca ccaaaucgc                                          19

<210> SEQ ID NO 82
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 82

-continued gcgauuuggu gauuuccac                                          19

<210> SEQ ID NO 83
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 83
uggaaaucac caaaucgca                                          19

<210> SEQ ID NO 84
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 84
ugcgauuugg ugauuucca                                          19

<210> SEQ ID NO 85
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 85
ggaaaucacc aaaucgcac                                          19

<210> SEQ ID NO 86
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 86
gugcgauuug gugauuucc                                          19

<210> SEQ ID NO 87
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 87
gaaaucacca aaucgcacc                                          19

<210> SEQ ID NO 88
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 88
ggugcgauuu ggugauuuc                                              19

<210> SEQ ID NO 89
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 89
aaaucaccaa aucgcacca                                              19

<210> SEQ ID NO 90
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 90
uggugcgauu uggugauuu                                              19

<210> SEQ ID NO 91
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 91
aaucaccaaa ucgcaccau                                              19

<210> SEQ ID NO 92
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 92
auggugcgau uuggugauu                                              19

<210> SEQ ID NO 93
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 93
aucaccaaau cgcaccaua                                              19

<210> SEQ ID NO 94
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 94
uauggugcga uuuggugau                                              19

```
<210> SEQ ID NO 95
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 95
ucaccaaauc gcaccauac                                                19

<210> SEQ ID NO 96
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 96
guauggugcg auuugguga                                                19

<210> SEQ ID NO 97
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 97
caccaaaucg caccauacg                                                19

<210> SEQ ID NO 98
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 98
cguauggugc gauuuggug                                                19

<210> SEQ ID NO 99
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 99
accaaaucgc accauacga                                                19

<210> SEQ ID NO 100
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 100
ucguauggug cgauuuggu                                                19
```

```
<210> SEQ ID NO 101
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 101
ccaaaucgca ccauacgaa                                               19

<210> SEQ ID NO 102
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 102
uucguauggu gcgauuugg                                               19

<210> SEQ ID NO 103
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 103
caaaucgcac cauacgaaa                                               19

<210> SEQ ID NO 104
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 104
uuucguaugg ugcgauuug                                               19

<210> SEQ ID NO 105
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 105
aaaucgcacc auacgaaau                                               19

<210> SEQ ID NO 106
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 106
auuucguaug gugcgauuu                                               19
```

```
<210> SEQ ID NO 107
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 107
aaucgcacca uacgaaaua                                                    19

<210> SEQ ID NO 108
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 108
uauuucguau ggugcgauu                                                    19

<210> SEQ ID NO 109
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 109
aucgcaccau acgaaauau                                                    19

<210> SEQ ID NO 110
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 110
auauuucgua uggugcgau                                                    19

<210> SEQ ID NO 111
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 111
ucgcaccaua cgaaauauu                                                    19

<210> SEQ ID NO 112
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 112
aauauuucgu auggugcga                                                    19

<210> SEQ ID NO 113
```

```
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 113
cgcaccauac gaaauauuc                                               19

<210> SEQ ID NO 114
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 114
gaauauuucg uauggugcg                                               19

<210> SEQ ID NO 115
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 115
guggaaauca ccaaauugc                                               19

<210> SEQ ID NO 116
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 116
gcaauuuggu gauuccac                                                19

<210> SEQ ID NO 117
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 117
uggaaaucac caaauugca                                               19

<210> SEQ ID NO 118
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 118
ugcaauuugg ugauuucca                                               19

<210> SEQ ID NO 119
<211> LENGTH: 19
```

<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 119
ggaaaucacc aaauugcac                                                19

<210> SEQ ID NO 120
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 120
gugcaauuug gugauuucc                                                19

<210> SEQ ID NO 121
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 121
gaaaucacca aauugcacc                                                19

<210> SEQ ID NO 122
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 122
ggugcaauuu ggugauuuc                                                19

<210> SEQ ID NO 123
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 123
aaaucaccaa auugcacca                                                19

<210> SEQ ID NO 124
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 124
uggugcaauu uggugauuu                                                19

<210> SEQ ID NO 125
<211> LENGTH: 19
<212> TYPE: RNA

```
<213> ORGANISM: Artificial Sequence
<220> FEATURE:
<223> OTHER INFORMATION: Description of Artificial Sequence: Synthetic
      oligonucleotide

<400> SEQUENCE: 125
aaucaccaaa uugcaccau                                              19

<210> SEQ ID NO 126
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 126
auggugcaau uuggugauu                                              19

<210> SEQ ID NO 127
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 127
aucaccaaau ugcaccaua                                              19

<210> SEQ ID NO 128
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 128
uauggugcaa uuuggugau                                              19

<210> SEQ ID NO 129
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 129
ucaccaaauu gcaccauac                                              19

<210> SEQ ID NO 130
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 130
guauggugca auuugguga                                              19

<210> SEQ ID NO 131
<211> LENGTH: 19
<212> TYPE: RNA
<213> ORGANISM: Artificial Sequence
```

-continued

```
<220> FEATURE:
<223> OTHER INFORMATION: Description of Artificial Sequence: Synthetic
      oligonucleotide

<400> SEQUENCE: 131
caccaaauug caccauacg                                                   19

<210> SEQ ID NO 132
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 132
cguauggugc aauuuggug                                                   19

<210> SEQ ID NO 133
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 133
accaaauugc accauacga                                                   19

<210> SEQ ID NO 134
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 134
ucguauggug caauuuggu                                                   19

<210> SEQ ID NO 135
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 135
ccaaauugca ccauacgaa                                                   19

<210> SEQ ID NO 136
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 136
uucguauggu gcaauuugg                                                   19

<210> SEQ ID NO 137
<211> LENGTH: 19
<212> TYPE: RNA
<213> ORGANISM: Artificial Sequence
<220> FEATURE:
```

```
<223> OTHER INFORMATION: Description of Artificial Sequence: Synthetic
      oligonucleotide

<400> SEQUENCE: 137
caaauugcac cauacgaaa                                                        19

<210> SEQ ID NO 138
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 138
uuucguaugg ugcaauuug                                                        19

<210> SEQ ID NO 139
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 139
aaauugcacc auacgaaau                                                        19

<210> SEQ ID NO 140
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 140
auuucguaug gugcaauuu                                                        19

<210> SEQ ID NO 141
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 141
aauugcacca uacgaaaua                                                        19

<210> SEQ ID NO 142
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 142
uauuucguau ggugcaauu                                                        19

<210> SEQ ID NO 143
<211> LENGTH: 19
<212> TYPE: RNA
<213> ORGANISM: Artificial Sequence
<220> FEATURE:
<223> OTHER INFORMATION: Description of Artificial Sequence: Synthetic
``` oligonucleotide

<400> SEQUENCE: 143
auugcaccau acgaaauau                                                19

<210> SEQ ID NO 144
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 144
auauuucgua uggugcaau                                                19

<210> SEQ ID NO 145
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 145
uugcaccaua cgaaauauu                                                19

<210> SEQ ID NO 146
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 146
aauauuucgu auggugcaa                                                19

<210> SEQ ID NO 147
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 147
ugcaccauac gaaauauuc                                                19

<210> SEQ ID NO 148
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 148
gaauauuucg uauggugca                                                19

<210> SEQ ID NO 149
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 149
guggaaauca ccaaaugac                                                19

<210> SEQ ID NO 150
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 150
gucauuuggu gauuuccac                                                19

<210> SEQ ID NO 151
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 151
uggaaaucac caaaugaca                                                19

<210> SEQ ID NO 152
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 152
ugucauuugg ugauuucca                                                19

<210> SEQ ID NO 153
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 153 ggaaacacc aaaugacac                                                 19

<210> SEQ ID NO 154
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 154
gugucauuug gugauuucc                                                19

<210> SEQ ID NO 155
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

```
<400> SEQUENCE: 155
gaaaucacca aaugacacc                                                19

<210> SEQ ID NO 156
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 156
ggugucauuu ggugauuuc                                                19

<210> SEQ ID NO 157
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 157
aaaucaccaa augacacca                                                19

<210> SEQ ID NO 158
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 158
uggugucauu uggugauuu                                                19

<210> SEQ ID NO 159
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 159
aaucaccaaa ugacaccau                                                19

<210> SEQ ID NO 160
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 160
auggugucau uuggugauu                                                19

<210> SEQ ID NO 161
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 161
```

-continued aucaccaaau gacaccaua					19

<210> SEQ ID NO 162
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 162
uaugguguca uuuggugau					19

<210> SEQ ID NO 163
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 163
ucaccaaaug acaccauac					19

<210> SEQ ID NO 164
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 164
guaugguguc auuugguga					19

<210> SEQ ID NO 165
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 165
caccaaauga caccauacg					19

<210> SEQ ID NO 166
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 166
cguauggugu cauuuggug					19

<210> SEQ ID NO 167
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 167

-continued accaaaugac accauacga 19

<210> SEQ ID NO 168
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 168
ucguauggug ucauuuggu 19

<210> SEQ ID NO 169
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 169
ccaaaugaca ccauacgaa 19

<210> SEQ ID NO 170
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 170
uucguauggu gucauuugg 19

<210> SEQ ID NO 171
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 171
caaaugacac cauacgaaa 19

<210> SEQ ID NO 172
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 172
uuucguaugg ugucauuug 19

<210> SEQ ID NO 173
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 173
aaaugacacc auacgaaau 19

<210> SEQ ID NO 174
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 174
auuucguaug gugucauuu                                                19

<210> SEQ ID NO 175
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 175
aaugacacca uacgaaaua                                                19

<210> SEQ ID NO 176
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 176
uauuucguau ggugucauu                                                19

<210> SEQ ID NO 177
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 177
augacaccau acgaaauau                                                19

<210> SEQ ID NO 178
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 178
auauuucgua uggugucau                                                19

<210> SEQ ID NO 179
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 179
ugacaccaua cgaaauauu                                                19

```
<210> SEQ ID NO 180
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 180
aauauuucgu augguguca                                                    19

<210> SEQ ID NO 181
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 181
gacaccauac gaaauauuc                                                    19

<210> SEQ ID NO 182
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 182
gaauauuucg uaugguguc                                                    19

<210> SEQ ID NO 183
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 183
guggaaauca ccaaaugcc                                                    19

<210> SEQ ID NO 184
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 184
ggcauuuggu gauuuccac                                                    19

<210> SEQ ID NO 185
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 185
uggaaaucac caaaugcca                                                    19
```

```
<210> SEQ ID NO 186
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 186
uggcauuugg ugauuucca                                                19

<210> SEQ ID NO 187
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 187
ggaaaucacc aaaugccac                                                19

<210> SEQ ID NO 188
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 188
guggcauuug gugauuucc                                                19

<210> SEQ ID NO 189
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 189
gaaaucacca aaugccacc                                                19

<210> SEQ ID NO 190
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 190
gguggcauuu ggugauuuc                                                19

<210> SEQ ID NO 191
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 191
aaaucaccaa augccacca                                                19

<210> SEQ ID NO 192
```

```
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 192
ugguggcauu uggugauuu                                                       19

<210> SEQ ID NO 193
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 193
aaucaccaaa ugccaccau                                                       19

<210> SEQ ID NO 194
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 194
augguggcau uuggugauu                                                       19

<210> SEQ ID NO 195
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 195
aucaccaaau gccaccaua                                                       19

<210> SEQ ID NO 196
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 196
uaugguggca uuuggugau                                                       19

<210> SEQ ID NO 197
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 197
ucaccaaaug ccaccauac                                                       19

<210> SEQ ID NO 198
<211> LENGTH: 19
```

```
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 198 guauggugge auuugguga                                                    19

<210> SEQ ID NO 199
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 199
caccaaaugc caccauacg                                                    19

<210> SEQ ID NO 200
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 200
cguauggugg cauuuggug                                                    19

<210> SEQ ID NO 201
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 201
accaaaugcc accauacga                                                    19

<210> SEQ ID NO 202
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 202
uucguauggu ggcauuugg                                                    19

<210> SEQ ID NO 203
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 203
ccaaaugcca ccauacgaa                                                    19

<210> SEQ ID NO 204
<211> LENGTH: 19
<212> TYPE: RNA
```

```
<213> ORGANISM: Artificial Sequence
<220> FEATURE:
<223> OTHER INFORMATION: Description of Artificial Sequence: Synthetic
      oligonucleotide

<400> SEQUENCE: 204
uuucguaugg uggcauuug                                                   19

<210> SEQ ID NO 205
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 205
caaaugccac cauacgaaa                                                   19

<210> SEQ ID NO 206
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 206
auuucguaug guggcauuu                                                   19

<210> SEQ ID NO 207
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 207
aaaugccacc auacgaaau                                                   19

<210> SEQ ID NO 208
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 208
uauuucguau gguggcauu                                                   19

<210> SEQ ID NO 209
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 209
aaugccacca uacgaaaua                                                   19

<210> SEQ ID NO 210
<211> LENGTH: 19
<212> TYPE: RNA
<213> ORGANISM: Artificial Sequence
```

```
<220> FEATURE:
<223> OTHER INFORMATION: Description of Artificial Sequence: Synthetic
      oligonucleotide

<400> SEQUENCE: 210
auauuucgua ugguggcau                                                    19

<210> SEQ ID NO 211
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 211
augccaccau acgaaauau                                                    19

<210> SEQ ID NO 212
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 212
aauauuucgu augguggca                                                    19

<210> SEQ ID NO 213
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 213
ugccaccaua cgaaauauu                                                    19

<210> SEQ ID NO 214
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 214
gaauauuucg uaugguggc                                                    19

<210> SEQ ID NO 215
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 215
gccaccauac gaaauauuc                                                    19

<210> SEQ ID NO 216
<211> LENGTH: 19
<212> TYPE: RNA
<213> ORGANISM: Artificial Sequence
<220> FEATURE:
```

```
<223> OTHER INFORMATION: Description of Artificial Sequence: Synthetic
      oligonucleotide

<400> SEQUENCE: 216
gacauuuggu gauuuccac                                                      19

<210> SEQ ID NO 217
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 217
uggaaaucac caaauguca                                                      19

<210> SEQ ID NO 218
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 218
ugacauuugg ugauuucca                                                      19

<210> SEQ ID NO 219
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 219
ggaaaucacc aaaugcac                                                       19

<210> SEQ ID NO 220
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 220
gugacauuug gugauuucc                                                      19

<210> SEQ ID NO 221
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 221
gaaaucacca aaugucacc                                                      19

<210> SEQ ID NO 222
<211> LENGTH: 19
<212> TYPE: RNA
<213> ORGANISM: Artificial Sequence
<220> FEATURE:
<223> OTHER INFORMATION: Description of Artificial Sequence: Synthetic
``` oligonucleotide

<400> SEQUENCE: 222
ggugacauuu ggugauuuc                                                    19

<210> SEQ ID NO 223
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 223
aaaucaccaa augucacca                                                    19

<210> SEQ ID NO 224
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 224
uggugacauu uggugauuu                                                    19

<210> SEQ ID NO 225
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 225
aaucaccaaa ugucaccau                                                    19

<210> SEQ ID NO 226
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 226
auggugacau uuggugauu                                                    19

<210> SEQ ID NO 227
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 227
aucaccaaau gucaccaua                                                    19

<210> SEQ ID NO 228
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 228
uauggugaca uuuggugau                                                    19

<210> SEQ ID NO 229
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 229
ucaccaaaug ucaccauac                                                    19

<210> SEQ ID NO 230
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 230
guauggugac auuggguga                                                    19

<210> SEQ ID NO 231
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 231
caccaaaugu caccauacg                                                    19

<210> SEQ ID NO 232
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 232
cguaggguga cauuggug                                                     19

<210> SEQ ID NO 233
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 233
accaaauguc accauacga                                                    19

<210> SEQ ID NO 234
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

```
<400> SEQUENCE: 234
ucguauggug acauuuggu                                                    19

<210> SEQ ID NO 235
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 235
ccaaauguca ccauacgaa                                                    19

<210> SEQ ID NO 236
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 236
uucguauggu gacauuugg                                                    19

<210> SEQ ID NO 237
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 237
caaaugucac cauacgaaa                                                    19

<210> SEQ ID NO 238
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 238
uuucguaugg ugacauuug                                                    19

<210> SEQ ID NO 239
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 239
aaaugucacc auacgaaau                                                    19

<210> SEQ ID NO 240
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 240
```
auuucguaug gugacauuu                                              19

<210> SEQ ID NO 241
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 241 aaugcacca uacgaaaua                                               19

<210> SEQ ID NO 242
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 242
uauuucguau ggugacauu                                              19

<210> SEQ ID NO 243
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 243
augucaccau acgaaauau                                              19

<210> SEQ ID NO 244
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 244
auauuucgua uggugacau                                              19

<210> SEQ ID NO 245
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 245
ugucaccaua cgaaauauu                                              19

<210> SEQ ID NO 246
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 246

```
aauauuucgu auggugaca                                                       19

<210> SEQ ID NO 247
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 247
gucaccauac gaaauauuc                                                       19

<210> SEQ ID NO 248
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 248
gaauauuucg uauggugac                                                       19

<210> SEQ ID NO 249
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 249
ucguauggug gcauuuggu                                                       19

<210> SEQ ID NO 250
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 250
guggaaauca ccaaauguc                                                       19
```